United States Patent
Yang et al.

(10) Patent No.: US 9,651,528 B2
(45) Date of Patent: May 16, 2017

(54) DIARYLAMINE-BASED FLUOROGENIC PROBES FOR DETECTION OF PEROXYNITRITE

(71) Applicant: The University of Hong Kong, Hong Kong (CN)

(72) Inventors: Dan Yang, Hong Kong (CN); Tao Peng, Hunan Province (CN); Jiangang Shen, Hong Kong (CN); Xingmiao Chen, Hong Kong (CN)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 0 days.

(21) Appl. No.: 13/754,499

(22) Filed: Jan. 30, 2013

(65) Prior Publication Data

US 2013/0196362 A1 Aug. 1, 2013

Related U.S. Application Data

(60) Provisional application No. 61/592,122, filed on Jan. 30, 2012.

(51) Int. Cl.
| | | |
|---|---|---|
| *C07D 311/82* | (2006.01) | |
| *C07D 311/90* | (2006.01) | |
| *C07D 491/052* | (2006.01) | |
| *C07D 493/10* | (2006.01) | |
| *C07D 493/20* | (2006.01) | |
| *C07F 9/6561* | (2006.01) | |
| *C09B 11/08* | (2006.01) | |
| *G01N 33/84* | (2006.01) | |
| *G01N 31/22* | (2006.01) | |
| *G01N 33/58* | (2006.01) | |
| *C07F 7/08* | (2006.01) | |
| *C09B 11/24* | (2006.01) | |
| *C09B 69/00* | (2006.01) | |

(52) U.S. Cl.
CPC ......... *G01N 31/227* (2013.01); *C07D 311/82* (2013.01); *C07D 311/90* (2013.01); *C07D 491/052* (2013.01); *C07D 493/10* (2013.01); *C07D 493/20* (2013.01); *C07F 7/0816* (2013.01); *C07F 9/6561* (2013.01); *C09B 11/08* (2013.01); *C09B 11/24* (2013.01); *C09B 11/245* (2013.01); *C09B 69/008* (2013.01); *G01N 33/582* (2013.01); *G01N 33/84* (2013.01); *Y10T 436/170769* (2015.01)

(58) Field of Classification Search
CPC C07D 311/82; C07D 311/90; C07D 491/052; C07D 493/10; C07D 493/20; C07F 7/0816; C07F 9/6561; C09B 11/08; C09B 11/24; C09B 11/245; C09B 69/008; G01N 31/227; G01N 33/582; G01N 33/84

See application file for complete search history.

(56) References Cited

U.S. PATENT DOCUMENTS

| | | | | |
|---|---|---|---|---|
| 3,022,316 | A * | 2/1962 | Bestian et al. | 549/394 |
| 3,772,335 | A * | 11/1973 | Meininger | C09B 62/443 544/150 |
| 2004/0171817 | A1* | 9/2004 | Allen | B41M 5/1455 534/653 |
| 2006/0293523 | A1* | 12/2006 | Filosa | B41M 5/3275 546/16 |
| 2009/0253118 | A1* | 10/2009 | Yang | C07D 307/94 435/4 |

FOREIGN PATENT DOCUMENTS

JP 09241558 * 9/1997

OTHER PUBLICATIONS

Lee et al. (ACS Chemical Biology (2010), 5(11): p. 1065-1074).*
Yang (Organic Letters 2010 vol. 12 (21) 4932-4935).*

* cited by examiner

*Primary Examiner* — Valerie Rodriguez-Garcia
(74) *Attorney, Agent, or Firm* — Saliwanchik, Lloyd & Eisenschenk

(57) ABSTRACT

Provided herein are improved fluorogenic compounds and probes that can be used as reagents for measuring, detecting and/or screening peroxynitrite. The fluorogenic compounds of the invention can produce fluorescence colors, such as green, yellow, red, or far-red. Also provided herein are fluorogenic compounds for selectively staining peroxynitrite in the mitochondria of living cells. Provided also herein are methods that can be used to measure, directly or indirectly, the presence and/or amount of peroxynitrite in chemical samples and biological samples such as cells and tissues in living organisms. Also provided are high-throughput screening methods for detecting or screening peroxynitrite or compounds that can increase or decrease the level of peroxynitrite in chemical and biological samples.

6 Claims, 19 Drawing Sheets

DIARYLAMINE-BASED FLUOROGENIC PROBES FOR DETECTION OF PEROXYNITRITE

CROSS-REFERENCE TO RELATED APPLICATION

This application claims the benefit of U.S. Provisional Application Ser. No. 61/592,122, filed Jan. 30, 2012, which is hereby incorporated by reference in its entirety.

BACKGROUND

Fluorescence technology is enjoying ever-increasing interest from chemistry to many areas of biology. In certain instances, fluorescent molecules are used to detect the presence of analytes in food and environmental samples. Some sensitive and quantitative fluorescence detection devices are ideal for in vitro biochemical assays such as DNA sequencing and blood glucose quantification. Moreover, certain fluorescent probes are indispensable for tracing molecular and physiological events in living cells. Finally, fluorescence measurements are often used in many high-throughput screenings.

The primary advantages of fluorescence technology over other types of optical measurements include sensitivity, simplicity, and a wealth of molecular information. Fluorescence measurements are highly sensitive because of the generally low level of fluorescence background in most chemical and biological samples. Along with the advances in fluorescence instrumentation such as confocal and multi-photo fluorescence microscopies, three-dimensional imagings of cellular events and biological species dynamics have become possible in real-time.

Particularly, fluorescence in biological sciences is generally used as a non-destructive way for tracking or analyzing biological molecules, such as proteins, metal ions, reactive oxygen species (ROS)/reactive nitrogen species (RNS), and so on, by recording or imaging the fluorescence emission of certain fluorescent probes for corresponding biological molecules at specific wavelengths where there is no cellular intrinsic fluorescence induced by the excitation light.

Among these intriguing biological molecules in living systems, reactive oxygen species (ROS) and reactive nitrogen species (RNS) have been receiving much attention from the scientific community in the development of fluorescent probes for their detection in biological samples. Reactive oxygen species (ROS) and reactive nitrogen species (RNS) are generally known to scientists as very small inorganic or organic molecules with high reactivity in living systems. There are various forms of ROS and RNS, including free radicals such as superoxide radical, hydroxyl radical, nitric oxide, nitrogen dioxide, and organic peroxyl radical; as well as non-radical species such as hydrogen peroxide, singlet oxygen, ozone, nitrous acid, peroxynitrite, and hypochlorite. ROS and RNS are by-products of cellular respiration. Under normal conditions, ROS and RNS are present in very low levels and play important roles in cell signaling; while during oxidative stresses, ROS and RNS levels increase dramatically, which can cause serious damages to various biological molecules such as protein, lipids and DNA. The excessive generation of ROS and RNS has been implicated in a lot of human diseases, such as cardiovascular diseases, inflammatory diseases, metabolic diseases, cancer and central nervous system diseases. Therefore, there is a strong need for chemicals that can sensitively and selectively measure, detect or screen certain ROS and RNS to address their physiological roles both in vitro and in vivo.

Peroxynitrite has the strongest oxidizing power among the various forms of ROS and RNS, and their selective detections are highly desirable to clearly explain their critical roles in living organisms. Peroxynitrite (ONOO$^-$) is a short-lived oxidant species that is formed in vivo by the diffusion-controlled reaction (k=0.4-1.9×10$^{10}$ M$^{-1}$s$^{-1}$) of nitric oxide (NO) and superoxide (O$_2$.$^-$) in one to one stoichiometry. The oxidant reactivity of peroxynitrite is highly pH-dependent and both peroxynitrite anion and its protonated form peroxynitrous acid can participate directly in one- and two-electron oxidation reactions with biomolecules. The pathological activity of ONOO$^-$ is also related to its reaction with the biologically ubiquitous CO$_2$, thereby producing the highly reactive radicals CO$_3^-$. and NO$_2$. in about 35% yield. As a result of this, peroxynitrite can nitrate tyrosine and oxidize proteins, lipids and iron and sulfur clusters of biological molecules. Like other oxidizing agents in living organisms, peroxynitrite and its protonated form have been associated with both beneficial and harmful effects. However, several studies have implicated that peroxynitrite contributes to tissue injury in a number of human diseases such as ischemic reperfusion injury, rheumatoid arthritis, septic shock, multiple sclerosis, atherosclerosis, stroke, inflammatory bowl disease, cancer, and several neurodegenerative diseases (MacMillan-Crow, L. A. et al., *Proc. Natl. Acad. Sci. USA* 1996, 93, 11853-11858; Rodenas, J. et al., *Free Radical. Biol. & Med.* 2000, 28, 374; Cuzzocrea, S. et al., *Pharmacol Rev.* 2001, 53, 135-159; Szabo, C. *Toxicol. Lett.* 2003, 140, 105-112; White, C. R. et al., *Proc. Natl. Acad. Sci. USA* 1994, 91, 1044-1048; Lipton, S. A. et al., *Nature* 1993, 364, 626-632; Pappolla, M. A. et al., *J. Neural Transm.* 2000, 107, 203-231; Beal, M. F., *Free Radical Biol. & Med.* 2002, 32, 797-803).

At present, peroxynitrite probes with green fluorescent color are available (U.S. patent application Ser. No. 12/417,672); however, the existing green fluorescent probes exhibit limited intracellular retention in cell assays. In addition, peroxynitrite probes with other fluorescent colors or with the ability to localize in the desired intracellular compartment are rare. Long-wavelength fluorogenic probes, such as yellow, red, far-red, and near-infrared (NIR) fluorogenic probes, are more attractive and advantageous than green probes for providing reliable imaging in biological samples, since they effectively avoid the interference from the autofluorescence of cells in the green region and possess longer excitation/emission wavelengths with deeper penetration into cells and tissues. Therefore, new generations of fluorescent probes with much more desirable and reliable detection and imaging of peroxynitrite are needed.

BRIEF SUMMARY

The subject invention provides improved fluorogenic or fluorescent compounds and probes for sensitive and specific detection of peroxynitrite. In one embodiment, provided herein are fluorogenic or fluorescent compounds that produce fluorescence colors such as green, yellow, red, or far-red. Also provided herein are fluorogenic or fluorescent compounds for selectively staining peroxynitrite in mitochondria of living cells.

In one aspect, the subject invention provides fluorogenic or fluorescent compounds represented by formula (I) or (II):

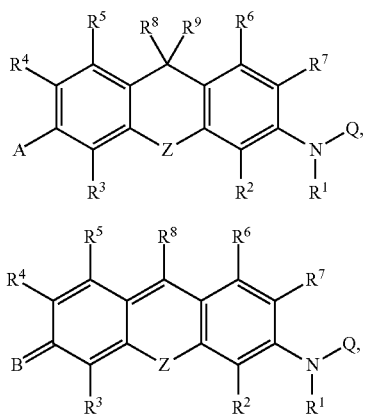

or a tautomer thereof;

wherein N is a nitrogen atom, and is linked to Q and $R^1$ through single covalent bonds;

$R^1$ is H, alkyl, halogenated alkyl, alkenyl, alkynyl, alkoxyalkyl, heteroalkyl, cycloalkyl, cycloalkenyl, cycloalkynyl, heterocyclyl, aminoalkyl, arylalkyl, alkyloxy, carboxyalkyl, alkylamino, alkoxyamino, alkylamido, alkoxyamido, or acyl;

each of $R^2$, $R^3$, $R^4$, $R^5$, $R^6$ and $R^7$ is independently H, F, Cl, Br, I, CN, alkyl, halogenated alkyl, heteroalkyl, alkenyl, alkynyl, aralkyl, aryl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thiol, thioalkyl, alkoxy, alkylthio, alkoxyalkyl, aryloxy, arylalkoxy, acyloxy, nitro, carbamoyl, trifluoromethyl, phenoxy, benzyloxy, phosphonic acid, phosphate ester, sulfonic acid (—$SO_3H$), sulfonate ester, sulfonamide, —C(=O)—$P^1$ or —C(=O)-M-$P^2$;

each of $P^1$ and $P^2$ is independently hydrogen, halo, alkoxy, hydroxy, thiol, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, alkyltriphenylphosphonium, or heterocyclyl having from 3 to 7 ring atoms;

M is alkylene, alkenylene, alkynylene, arylene, aralkylene or alkarylene;

A is $OR^{10}$ or $NR^{11}R^{12}$;

wherein $R^{10}$ is H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, carboxyalkyl, alkoxycarbonyl, acyl or aminocarbonyl;

wherein each of $R^{11}$ and $R^{12}$ is independently H, alkyl, halogenated alkyl, alkenyl, alkynyl, alkoxyalkyl, heteroalkyl, cycloalkyl, cycloalkenyl, cycloalkynyl, heterocyclyl, aminoalkyl, arylalkyl, alkyloxy, acyl, carboxyalkyl, sulfoalkyl, a salt of carboxyalkyl, a salt of sulfoalkyl, or an ester or amide of carboxyalkyl or sulfoalkyl; or $R^{11}$ in combination with $R^{12}$ forms a saturated 5- or 6-membered heterocycle that is a piperidine, a morpholine, a pyrrolidine or a piperazine, each of which is optionally substituted by alkyl, carboxylic acid, a salt of carboxylic acid, or a carboxylic acid ester of an alcohol; or $R^{11}$ in combination with $R^4$, or $R^{12}$ in combination with $R^3$, or both, form a 5- or 6-membered ring that is saturated or unsaturated, or further fused with an aryl or heteroaryl ring, and is optionally substituted by one or more alkyls, carboxylic acids, sulfonic acids (—$SO_3H$), or their salts, ester or amide derivatives;

B is O or $N^+R^{11}R^{12}$;

Z is O, S, $NR^{13}$, $CR^{13}R^{14}$, $SiR^{13}R^{14}$, $GeR^{13}R^{14}$, or $SnR^{13}R^{14}$;

wherein each of $R^{13}$ and $R^{14}$ is independently H, alkyl, halogenated alkyl, heteroalkyl, alkenyl, alkynyl, aralkyl, aryl, alkaryl, heterocyclyl, cycloalkyl, cycloalkenyl, cycloalkynyl, hydroxyalkyl, aminoalkyl, hydroxy, thiol, thioalkyl, alkoxy, alkylthio, alkoxyalkyl, aryloxy, arylalkoxy, acyloxy, carbamoyl, trifluoromethyl, phenoxy, benzyloxy, phosphonic acid, phosphate ester, sulfonic acid (—$SO_3H$), sulfonate ester, sulfonamide, carboxylic acid, carboxylic ester, or carboxylic amide; or $R^{13}$ in combination with $R^{14}$ forms a saturated 5- or 6-membered heterocycle that is optionally substituted by alkyl, carboxylic acid, a salt of carboxylic acid, or a carboxylic acid ester of an alcohol;

$R^8$ is H, $CF_3$, CN, a carboxylic acid, a salt of carboxylic acid, or a carboxylic acid ester of an alcohol; or $R^8$ is a saturated or unsaturated alkyl that is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—$SO_3H$), sulfonate ester (—$SO_3R^{15}$), or sulfonamide (—$SO_2NR^{15}R^{16}$), wherein each of $R^{15}$ and $R^{16}$ represents a saturated or unsaturated, cyclic or acyclic alkyl that is optionally substituted by one or more F, Cl, Br, I, a carboxylic acid, a salt of carboxylic acid, a carboxylic acid ester of an alcohol, amino, alkylamino, dialkylamino, alkoxy, or alkyltriphenylphosphonium; or $R^8$ has the formula

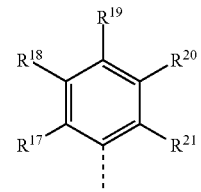

wherein each of $R^{17}$, $R^{18}$, $R^{19}$, $R^{20}$ and $R^{21}$ is independently H, F, Cl, Br, I, CN, nitro, a carboxylic acid, a salt of carboxylic acid, sulfonic acid (—$SO_3H$), sulfonate ester (—$SO_3R^{15}$), sulfonamide (—$SO_2NR^{15}R^{16}$), hydroxy, azide, alkyl, alkenyl, alkynyl, heteroalkyl, cycloalkyl, cycloalkenyl, cycloalkynyl, aryl, alkylaryl, arylalkyl, heterocyclyl, alkoxy, alkoxyalkyl, alkoxyalkoxy, acyl, alkylcarbonylalkyl, halogenated alkylcarbonylalkyl such as trifluoromethylcarbonylalkyl, aminoalkyl, carboxyalkyl, thiol, alkylthio, amino, alkylamino, dialkylamino, alkoxycarbonyl, alkoxycarbonylalkyl, aminocarbonyl, alkylaminocarbonyl, dialkylaminocarbonyl, or arylcarboxamido, the alkyl or aryl of which is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—$SO_3H$), sulfonate ester (—$SO_3R^{15}$), or sulfonamide (—$SO_2NR^{15}R^{16}$); or $R^{17}$ and $R^{18}$ together, $R^{18}$ and $R^{19}$ together, $R^{19}$ and $R^{20}$ together, or $R^{20}$ and $R^{21}$ together form a part of a 5- or 6-membered cycloalkyl, heterocyclyl, aryl or heteroaryl ring fused with the phenyl ring of formula (III) that is optionally further substituted by one or more F, Cl, Br, I, a carboxylic acid, a salt of carboxylic acid, a carboxylic acid ester of an alcohol, amino, alkylamino, dialkylamino, alkoxy, thiol, alkylthio, alkyltriphenylphosphonium, sulfonic acid (—$SO_3H$), sulfonate ester (—$SO_3R^{15}$), or sulfonamide (—$SO_2NR^{15}R^{16}$);

$R^9$ is H, hydroxy, CN or alkoxy; or $R^9$ in combination with $R^8$ forms a 5-membered spirolactone or spirolactam ring or a 5-membered spirosultam ring; or $R^9$ in combination with $R^{17}$ or $R^{21}$ forms a 5- or 6-membered spirolactone or spirolactam ring or a 5- or 6-membered spirosultone or spirosultam ring that is optionally and independently substituted by H, F or $CH_3$; specifically, $R^9$, when taken in combination with $R^8$ forming a 5-membered spirolactone or spirolactam ring or a 5-membered spirosultam ring, is oxygen or substituted nitrogen; and Q is substituted phenyl having formula (IV):

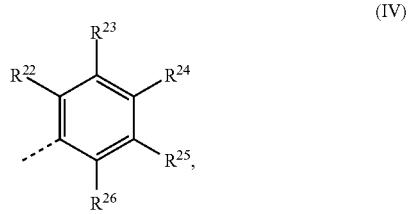

(IV)

wherein each of $R^{22}$, $R^{23}$, $R^{24}$, $R^{25}$, and $R^{26}$ is independently H, hydroxy, alkyl, alkenyl, alkynyl, heteroalkyl, cycloalkyl, cycloalkenyl, cycloalkynyl, aryl, alkylaryl, arylalkyl, heterocyclyl, alkoxy, alkoxyalkyl, alkoxyalkoxy, acyl, alkylcarbonylalkyl, halogenated alkylcarbonylalkyl such as trifluoromethylcarbonylalkyl, aminoalkyl, carboxyalkyl, thiol, alkylthio, amino, alkylamino, dialkylamino, alkoxycarbonyl, alkoxycarbonylalkyl, aminocarbonyl, alkylaminocarbonyl, dialkylaminocarbonyl, or arylcarboxamido, the alkyl or aryl of which is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—$SO_3H$), sulfonate ester (—$SO_3R^{15}$), or sulfonamide (—$SO_2NR^{15}R^{16}$); or $R^{22}$ and $R^{23}$ together, $R^{23}$ and $R^{24}$ together, $R^{24}$ and $R^{25}$ together, or $R^{25}$ and $R^{26}$ together form a part of a 5- or 6-membered cycloalkyl, heterocyclyl, aryl or heteroaryl ring fused with the phenyl ring of formula (IV) that is optionally further substituted by one or more F, Cl, Br, I, a carboxylic acid, a salt of carboxylic acid, a carboxylic acid ester of an alcohol, amino, alkylamino, dialkylamino, alkoxy, thiol, alkylthio, alkyltriphenylphosphonium, sulfonic acid (—$SO_3H$), sulfonate ester (—$SO_3R^{15}$), or sulfonamide (—$SO_2NR^{15}R^{16}$).

The subject invention also provides fluorogenic or fluorescent probe compositions, comprising a fluorogenic or fluorescent compound of the invention, and optionally, a carrier, solvent, an acid, a base, a buffer solution, or a combination thereof.

Also provided herein are methods for detecting the presence of, or measuring the level of, peroxynitrite in samples. In some embodiments, the methods comprise the steps of (a) contacting a fluorogenic compound or probe disclosed herein with a sample to form a fluorescent compound; and (b) determining or measuring fluorescent property of the fluorescent compound.

Also provided herein are high-throughput screening methods for detecting peroxynitrite in samples. In some embodiments, the high-throughput screening fluorogenic methods comprise the steps of (a) contacting a fluorogenic compound or probe disclosed herein with sample(s) to form a fluorescent compound; and (b) measuring fluorescence property of the fluorescent compound.

Also provided herein are high-throughput methods for screening one or more target compounds that can increase or decrease the level of peroxynitrite. In some embodiments, the high-throughput screening method for detecting peroxynitrite comprises the steps of: (a) contacting a fluorogenic compound or probe disclosed herein with samples to form one or more fluorescent compounds; and (b) measuring fluorescence property of the fluorescent compounds to determine the amount of peroxynitrite in the samples.

DEFINITIONS

Figure 1A:
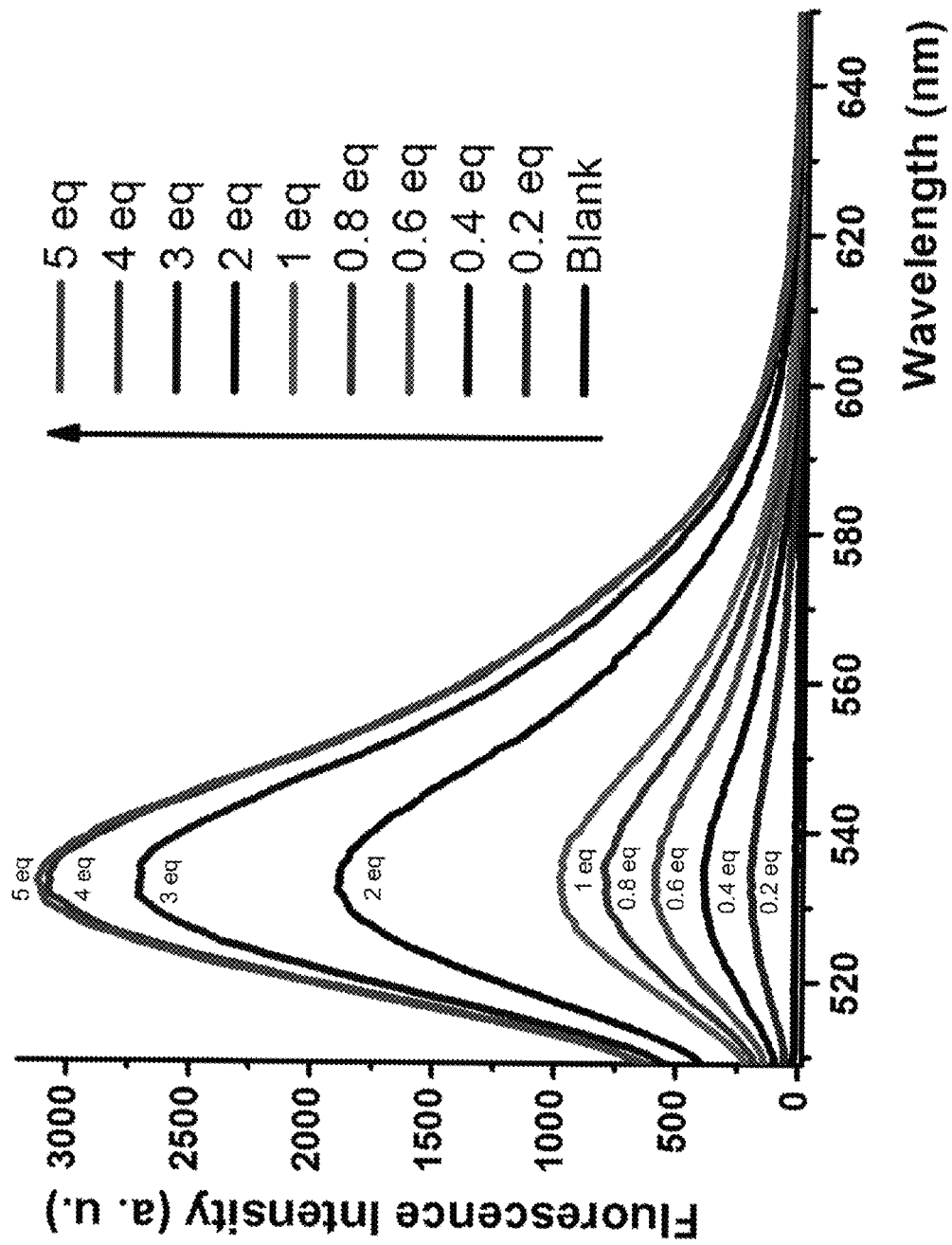
FIG. 1A depicts fluorescence spectra showing fluorescence intensities of compound 2 after treatment with different amounts of peroxynitrite.

To facilitate the understanding of the subject matter disclosed herein, a number of terms, abbreviations or other shorthand as used herein are defined below. Any term, abbreviation or shorthand not defined is understood to have the ordinary meaning used by a skilled artisan contemporaneous with the submission of this application.

"Amino" refers to a primary, secondary, or tertiary amine which may be optionally substituted. Specifically included are secondary or tertiary amine nitrogen atoms which are members of a heterocyclic ring. Also specifically included, for example, are secondary or tertiary amino groups substituted by an acyl moiety. Some non-limiting examples of an amino group include —NR'R" wherein each of R' and R" is independently H, alkyl, aryl, aralkyl, alkaryl, cycloalkyl, acyl, heteroalkyl, heteroaryl or heterocycyl.

"Alkyl" refers to a fully saturated acyclic monovalent radical containing carbon and hydrogen, and which may be branched or a straight chain. In some embodiments, alkyl contains from about 1 to about 25 carbon atoms. Examples of alkyl groups include, but are not limited to, methyl, ethyl, n-propyl, isopropyl, n-butyl, t-butyl, n-heptyl, n-hexyl, n-octyl, and n-decyl. "Lower alkyl" refers to an alkyl radical of one to six carbon atoms, as exemplified by methyl, ethyl, n-butyl, i-butyl, t-butyl, isoamyl, n-pentyl, and isopentyl.

"Heteroalkyl" refers to an alkyl group having one or more of the carbon atoms within the alkyl group substituted by a heteroatom such as O, S and N. In some embodiments, the heteroalkyl group comprises one or more O atoms. In other embodiments, the heteroalkyl group comprises one or more S atoms. In further embodiments, the heteroalkyl group comprises one or more aminylene groups. In certain embodiments, the heteroalkyl group comprises two or more O, S, aminylene, or a combination thereof.

"Alkenyl" or "alkenylene," respectively, refers to a monovalent or divalent hydrocarbyl radical which has at least one double bond. The alkenyl or alkenylene group may be branched acyclic or straight acyclic. In some embodiments, the alkenyl or alkenylene group contains only one double bond. In other embodiments, the alkenyl or alkenylene group contains two or more double bonds. In further embodiments, the alkenyl or alkenylene group can be a lower alkenyl or alkenylene containing from two to eight carbon atoms in the principal chain. In further embodiments, the alkenyl or alkenylene group can have one double bond and up to 25 carbon atoms, as exemplified by ethenyl, propenyl, isopropenyl, butenyl, isobutenyl, hexenyl, and the like.

"Alkynyl" or "alkynylene," respectively, refers to a monovalent or divalent hydrocarbyl radical which has at least a triple bond. In some embodiments, the alkynyl or alkynylene group contains only one triple bond. In other embodiments, the alkynyl or alkynylene group contains two or more triple bonds. In further embodiments, the alkynyl or alkynylene group can be a lower alkynyl or alkynylene containing from two to eight carbon atoms in the principal chain. In further embodiments, the alkynyl or alkynylene group can have one triple bond and up to 20 carbon atoms, as exemplified by ethynyl, propynyl, isopropynyl, butynyl, isobutynyl, hexynyl, and the like.

"Aromatic" or "aromatic group" refers to aryl or heteroaryl.

"Aryl" refers to optionally substituted carbocyclic aromatic groups. In some embodiments, the aryl group includes a monocyclic or bicyclic group containing from 6 to 12 carbon atoms in the ring portion, such as phenyl, biphenyl, naphthyl, substituted phenyl, substituted biphenyl or substituted naphthyl. In other embodiments, the aryl group is phenyl or substituted phenyl.

"Aralkyl" refers to an alkyl group which is substituted with an aryl group. Some non-limiting examples of aralkyl include benzyl and phenethyl.

"Alkaryl" refers to an aryl group which is substituted with an alkyl group. Some non-limiting examples of alkaryl include methylphenyl and methylnaphthyl.

"Acyl" refers to a monovalent group of the formula —C(=O)H, —C(=O)-alkyl, —C(=O)-aryl, —C(=O)-aralkyl, or —C(=O)-alkaryl.

"Halogen" refers to fluorine, chlorine, bromine and iodine.

"Halo" refers to fluoro, chloro, bromo and iodo.

"Heteroatom" refers to atoms other than carbon and hydrogen.

"Heterocyclo" or "heterocyclyl" refers to optionally substituted, fully saturated or unsaturated, monocyclic or bicyclic, aromatic or nonaromatic groups having at least one heteroatom, such as O, S, N, B and P, in at least one ring. The aromatic heterocyclyl (i.e., heteroaryl) group can have 1 or 2 oxygen atoms, 1 or 2 sulfur atoms, and/or 1 to 4 nitrogen atoms in the ring, and may be bonded to the remainder of the molecule through a carbon or heteroatom. Some non-limiting examples of heteroaryl include furyl, thienyl, thiazolyl, pyridyl, oxazolyl, pyrrolyl, indolyl, quinolinyl, or isoquinolinyl and the like.

"Hydrocarbon" or "hydrocarbyl" refers to organic compounds or radicals consisting exclusively of the elements carbon and hydrogen. Hydrocarbyl includes alkyl, alkenyl, alkynyl, and aryl moieties. Hydrocarbyl also includes alkyl, alkenyl, alkynyl, and aryl moieties substituted with other aliphatic, cyclic or aryl hydrocarbon groups, such as alkaryl, alkenaryl and alkynaryl. In some embodiments, "hydrocarbon" or "hydrocarbyl" comprises 1 to 30 carbon atoms.

"Hydrocarbylene" refers to a divalent group formed by removing two hydrogen atoms from a hydrocarbon, the free valencies of which are not engaged in a double bond, e.g. arylene, alkylene, alkenylene, alkynylene, aralkylene or alkarylene.

"Substituted" as used herein to describe a compound or chemical moiety refers to that at least one hydrogen atom of that compound or chemical moiety is replaced with a second chemical moiety. Non-limiting examples of substituents are those found in the exemplary compounds and embodiments disclosed herein, as well as halogen; alkyl; heteroalkyl; alkenyl; alkynyl; aryl, heteroaryl, hydroxy; alkoxyl; amino; nitro; thiol; thioether; imine; cyano; amido; phosphonato; phosphine; carboxyl; thiocarbonyl; sulfonyl; sulfonamide; ketone; aldehyde; ester; oxo; haloalkyl (e.g., trifluoromethyl); carbocyclic cycloalkyl, which can be monocyclic or fused or non-fused polycyclic (e.g., cyclopropyl, cyclobutyl, cyclopentyl or cyclohexyl) or a heterocycloalkyl, which can be monocyclic or fused or non-fused polycyclic (e.g., pyrrolidinyl, piperidinyl, piperazinyl, morpholinyl or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl or benzofuranyl); amino (primary, secondary or tertiary); o-lower alkyl; o-aryl, aryl; aryl-lower alkyl; —$CO_2CH_3$; —$CONH_2$; —$OCH_2CONH_2$; —$NH_2$; —$SO_2NH_2$; —$OCHF_2$; —$CF_3$; —$OCF_3$; —NH(alkyl); —N(alkyl)$_2$; —NH(aryl); —N(alkyl)(aryl); —N(aryl)$_2$; —CHO; —CO(alkyl); —CO(aryl); —$CO_2$(alkyl); and —$CO_2$(aryl); and such moieties can also be optionally substituted by a fused-ring structure or bridge, for example —$OCH_2O$—. These substituents can optionally be further substituted with a substituent selected from such groups. All chemical groups disclosed herein can be substituted, unless it is specified otherwise. For example, "substituted" alkyl, alkenyl, alkynyl, aryl, hydrocarbyl or heterocyclo moieties described herein are moieties which are substituted with a hydrocarbyl moiety, a substituted hydrocarbyl moiety, a heteroatom, or a heterocyclo. Further, substituents may include moieties in which a carbon atom is substituted with a heteroatom such as nitrogen, oxygen, silicon, phosphorus, boron, sulfur, or a halogen atom. These substituents may include halogen, heterocyclo, alkoxy, alkenoxy, alkynoxy, aryloxy, hydroxy, protected hydroxy, keto, acyl, acyloxy, nitro, amino, amido, cyano, thiol, ketals, acetals, esters and ethers.

"Fluorescence" refers to a luminescence where the molecular absorption of a photon triggers the emission of another photon with a longer wavelength. In some embodiments, the absorbed photon is in the ultraviolet range, and the emitted light is in the visible range.

"Green fluorescence" refers to a luminescence where the molecular absorption of a photon triggers the emission of another photon with a longer wavelength that is within the range of about 520 nm to about 570 nm.

"Yellow fluorescence" refers to a luminescence where the molecular absorption of a photon triggers the emission of another photon with a longer wavelength that is within the range of about 570 nm to about 590 nm.

"Orange fluorescence" refers to a luminescence where the molecular absorption of a photon triggers the emission of another photon with a longer wavelength that is within the range of about 585 nm to about 620 nm.

"Red fluorescence" refers to a luminescence where the molecular absorption of a photon triggers the emission of another photon with a longer wavelength that is within the range of about 620 nm to about 740 nm.

"Far-red fluorescence" refers to a luminescence where the molecular absorption of a photon triggers the emission of another photon with a longer wavelength that is within the range of about 650 nm to about 740 nm.

"Fluorophore" refers to a small molecule or a part of a large molecule that can be excited by light to emit fluorescence. In some embodiments, fluorophores efficiently produce fluorescence upon excitation with light which has a wavelength from about 200 nanometers to about 1000 nanometers, or from about 500 nanometers to about 800 nanometers. The intensity and wavelength of the emitted radiation generally depend on both the fluorophore and the chemical environment of the fluorophore. A fluorophore may be selected from acridine orange, anthracene ring, allophycocyanin, BODIPY, cyanines, coumarin, Edans, Eosin, Erythrosin, fluorescamine, fluorescein, FAM (carboxyfluorescein), HEX (hexachlorofluorescein), JOE (6-carboxy-4',5'-dichloro-2',7'-dimethoxy-fluorescein), Oregon Green, phycocyanin, phycoerythrin, rhodamine, ROX (Carboxy-X-rhodamine), TAMRA (carboxytetramethylrhodamine), TET (tetrachloro-fluorescein), Texas red, tetramethylrhodamine, and xanthines. Other non-limiting examples can be found in *The Handbook: a Guide to Fluorogenic Probes and Labeling Technologies* (10th Edition, Molecular Probes, Eugene, Orgeon, 2006), which are incorporated herein by reference.

"Reactive group" or "Rg" refers to a group that is highly reactive toward an amine, a thio, an alcohol, an aldehyde or a ketone. Some non-limiting examples of a reactive group include phosphoramidite, succinimidyl ester of a carboxylic acid, haloacetamide, hydrazine, isothiocyanate, maleimide, perfluorobenzamido, and azidoperfluorobenzamido.

"Conjugated substance" or "Cg" refers to a desired substance which needs to be conjugated and generally possess a suitable functional group for covalent reaction with a respective reactive group, Rg. Some non-limiting examples of conjugated substances include conjugates of antigens, steroids, vitamins, drugs, haptens, metabolites, toxins, amino acids, peptides, nucleotides, oligonucleotides, nucleic acid, carbohydrates, lipids, and the like.

"Reactive oxygen species" or ROS refer to oxygen-containing ions, free radicals as well as non-radical species. Some non-limiting examples of reactive oxygen species include $^1O_2$, $O_2.^-$, ROO., .OH, OCl$^-$, and $H_2O_2$.

"Reactive nitrogen species" or RNS refer to nitrogen-containing ions, free radicals as well as non-radical species. Some non-limiting examples of reactive nitrogen species include nitric oxide (NO.), nitrogen dioxide ($NO_2$.), nitrite ($NO_2^-$), and peroxynitrite ($ONOO^-$).

"Fluorogenic probe" refers to a latent fluorogenic molecule, whose fluorescence stays in "off" state before reacting with the target and may switch to "on" state after reacting with the target.

"Peroxynitrite fluorogenic compound" refers to a compound that can react with peroxynitrite to produce a fluorescence signal. In certain embodiments, the peroxynitrite fluorogenic compounds of the invention substantially react with peroxynitrite.

"Peroxynitrite-specific fluorogenic compound" or "fluorogenic compound that specifically detects peroxynitrite" refers to a fluorogenic compound that reacts with peroxynitrite in a yield of about 10% higher than, about 15% higher than, about 20% higher than, about 25% higher than, about 30% higher than, about 35% higher than, about 40% higher than, about 45% higher than, about 50% higher than, about 55% higher than, about 60% higher than, about 65% higher than, about 70% higher than, about 75% higher than, about 80% higher than, about 85% higher than, about 90% higher than, about 95% higher than, about 100% higher than, about 200% higher than, about 300% higher than, or about 500% higher than that of any other ROS and RNS.

"Reacting", "adding" or the like refers to contacting one reactant, reagent, solvent, catalyst, reactive group or the like with another reactant, reagent, solvent, catalyst, reactive group or the like. Reactants, reagents, solvents, catalysts, reactive group or the like can be added individually, simultaneously or separately and can be added in any order. They can be added in the presence or absence of heat and can optionally be added under an inert atmosphere. In some embodiments, "reacting" refers to in situ formation or intramolecular reaction where the reactive groups are in the same molecule.

"Substantially react" refers to that at least a reactant of a reaction is consumed by an amount of more than about 75% by mole, by more than about 80% by mole, by more than about 85% by mole, or by more than about 90% by mole. In some embodiments, "substantially react" refers to that the reactant is consumed by more than about 95% by mole. In other embodiments, "substantially react" refers to that the reactant is consumed by more than about 97% by mole. In further embodiments, "substantially react" refers to that the reactant is consumed by more than about 99% by mole.

"High-throughput method" refers to a method that can autonomously process or evaluate a large number of samples. In some embodiments, informatics systems can be used and implemented in the high-throughput method. The informatics systems can provide the software control of the physical devices used in the high-throughput method, as well as organize and store electronic data generated by the high-throughput method.

DETAILED DESCRIPTION

The subject invention provides a class of fluorogenic or fluorescent compounds and probes for sensitive and specific detection of peroxynitrite. Exemplary fluorogenic compounds and probes of the invention utilize an N-dearylation reaction between the diarylamine-caged fluorogenic compounds with peroxynitrite to achieve high sensitivity and selectivity for detecting peroxynitrite in aqueous solution over other reactive oxygen and nitrogen species (ROS/RNS). Exemplary fluorogenic compounds include compounds that produce fluorescence colors such as green, yellow, red, or far-red. Also provided herein are fluorogenic compounds for selectively staining peroxynitrite in mitochondria of living cells.

The fluorogenic compounds of the subject invention can be used to measure, directly or indirectly, the amount of peroxynitrite in both chemical and biological samples such as cells and tissues in living organisms, and therefore serve as powerful tools for interrogating the physiological and pathological roles of cellular peroxynitrite.

Compounds
General Aspects

In one aspect, the subject invention provides fluorogenic or fluorescent compounds. In one embodiment, the fluorogenic or fluorescent compounds of the invention are represented by formula (I) or (II):

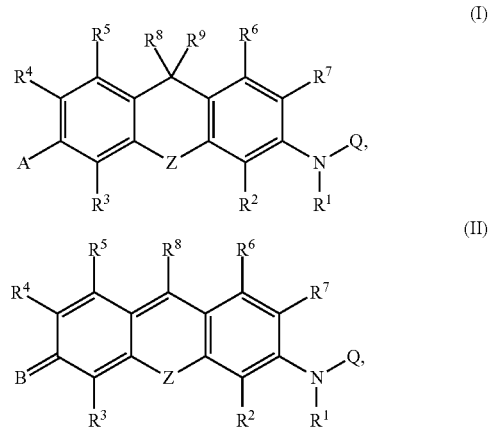

or a tautomer thereof;

wherein N is a nitrogen atom, and is linked to Q and $R^1$ through single covalent bonds;

$R^1$ is H, alkyl, halogenated alkyl, alkenyl, alkynyl, alkoxyalkyl, heteroalkyl, cycloalkyl, cycloalkenyl, cycloalkynyl, heterocyclyl, aminoalkyl, arylalkyl, alkyloxy, carboxyalkyl, alkylamino, alkoxyamino, alkylamido, alkoxyamido, or acyl;

each of $R^2$, $R^3$, $R^4$, $R^5$, $R^6$ and $R^7$ is independently H, F, Cl, Br, I, CN, alkyl, halogenated alkyl, heteroalkyl, alkenyl, alkynyl, aralkyl, aryl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thiol, thioalkyl, alkoxy, alkylthio, alkoxyalkyl, aryloxy, arylalkoxy, acyloxy, nitro, carbamoyl, trifluoromethyl, phenoxy, benzyloxy, phosphonic acid, phosphate ester, sulfonic acid (—SO₃H), sulfonate ester, sulfonamide, —C(=O)—P¹ or —C(=O)-M-P²;

each of P¹ and P² is independently hydrogen, halo, alkoxy, hydroxy, thiol, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, alkyltriphenylphosphonium, or heterocyclyl having from 3 to 7 ring atoms; M is alkylene, alkenylene, alkynylene, arylene, aralkylene or alkarylene;

A is OR¹⁰ or NR¹¹R¹²;

wherein R¹⁰ is H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, carboxyalkyl, alkoxycarbonyl, acyl or aminocarbonyl;

wherein each of R¹¹ and R¹² is independently H, alkyl, halogenated alkyl, alkenyl, alkynyl, alkoxyalkyl, heteroalkyl, cycloalkyl, cycloalkenyl, cycloalkynyl, heterocyclyl, aminoalkyl, arylalkyl, alkyloxy, acyl, carboxyalkyl, sulfoalkyl, a salt of carboxyalkyl, a salt of sulfoalkyl, or an ester or amide of carboxyalkyl or sulfoalkyl; or R¹¹ in combination with R¹² forms a saturated 5- or 6-membered heterocycle that is a piperidine, a morpholine, a pyrrolidine or a piperazine, each of which is optionally substituted by alkyl, carboxylic acid, a salt of carboxylic acid, or a carboxylic acid ester of an alcohol; or R¹¹ in combination with R⁴, or R¹² in combination with R³, or both, form a 5- or 6-membered ring that is saturated or unsaturated, or further fused with an aryl or heteroaryl ring, and is optionally substituted by one or more alkyls, carboxylic acids, sulfonic acids (—SO₃H), or their salts, ester or amide derivatives;

B is O or N⁺R¹¹R¹²;

Z is O, S, NR¹³, CR¹³R¹⁴, SiR¹³R¹⁴, GeR¹³R¹⁴, or SnR¹³R¹⁴;

wherein each of R¹³ and R¹⁴ is independently H, alkyl, halogenated alkyl, heteroalkyl, alkenyl, alkynyl, aralkyl, aryl, alkaryl, heterocyclyl, cycloalkyl, cycloalkenyl, cycloalkynyl, hydroxyalkyl, aminoalkyl, hydroxy, thiol, thioalkyl, alkoxy, alkylthio, alkoxyalkyl, aryloxy, arylalkoxy, acyloxy, carbamoyl, trifluoromethyl, phenoxy, benzyloxy, phosphonic acid, phosphate ester, sulfonic acid (—SO₃H), sulfonate ester, sulfonamide, carboxylic acid, carboxylic ester, or carboxylic amide; or R¹³ in combination with R¹⁴ forms a saturated 5- or 6-membered heterocycle that is optionally substituted by alkyl, carboxylic acid, a salt of carboxylic acid, or a carboxylic acid ester of an alcohol;

R⁸ is H, CF₃, CN, a carboxylic acid, a salt of carboxylic acid, or a carboxylic acid ester of an alcohol; or R⁸ is a saturated or unsaturated alkyl that is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—SO₃H), sulfonate ester (—SO₃R¹⁵), or sulfonamide (—SO₂NR¹⁵R¹⁶), wherein each of R¹⁵ and R¹⁶ represents a saturated or unsaturated, cyclic or acyclic alkyl that is optionally substituted by one or more F, Cl, Br, I, a carboxylic acid, a salt of carboxylic acid, a carboxylic acid ester of an alcohol, amino, alkylamino, dialkylamino, alkoxy, or alkyltriphenylphosphonium; or R⁸ has the formula

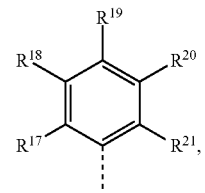

(III)

wherein each of R¹⁷, R¹⁸, R¹⁹, R²⁰ and R²¹ is independently H, F, Cl, Br, I, CN, nitro, a carboxylic acid, a salt of carboxylic acid, sulfonic acid (—SO₃H), sulfonate ester (—SO₃R¹⁵), sulfonamide (—SO₂NR¹⁵R¹⁶), hydroxy, azide, alkyl, alkenyl, alkynyl, heteroalkyl, cycloalkyl, cycloalkenyl, cycloalkynyl, aryl, alkylaryl, arylalkyl, heterocyclyl, alkoxy, alkoxyalkyl, alkoxyalkoxy, acyl, alkylcarbonylalkyl, halogenated alkylcarbonylalkyl such as trifluoromethylcarbonylalkyl, aminoalkyl, carboxyalkyl, thiol, alkylthio, amino, alkylamino, dialkylamino, alkoxycarbonyl, alkoxycarbonylalkyl, aminocarbonyl, alkylaminocarbonyl, dialkylaminocarbonyl, or arylcarboxamido, the alkyl or aryl of which is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—SO₃H), sulfonate ester (—SO₃R¹⁵), or sulfonamide (—SO₂NR¹⁵R¹⁶); or R¹⁷ and R¹⁸ together, R¹⁸ and R¹⁹ together, R¹⁹ and R²⁰ together, or R²⁰ and R²¹ together form a part of a 5- or 6-membered cycloalkyl, heterocyclyl, aryl or heteroaryl ring fused with the phenyl ring of formula (III) that is optionally further substituted by one or more F, Cl, Br, I, a carboxylic acid, a salt of carboxylic acid, a carboxylic acid ester of an alcohol, amino, alkylamino, dialkylamino, alkoxy, thiol, alkylthio, alkyltriphenylphosphonium, sulfonic acid (—SO₃H), sulfonate ester (—SO₃R¹⁵), or sulfonamide (—SO₂NR¹⁵R¹⁶);

R⁹ is H, hydroxy, CN or alkoxy; or R⁸ in combination with R⁹ forms a 5-membered spirolactone or spirolactam ring or a 5-membered spirosultam ring; or R⁹ in combination with R¹⁷ or R²¹ forms a 5- or 6-membered spirolactone or spirolactam ring or a 5- or 6-membered spirosultone or spirosultam ring that is optionally and independently substituted by H, F or CH₃; specifically, R⁹, when taken in combination with R⁸ forming a 5-membered spirolactone or spirolactam ring or a 5-membered spirosultam ring, is oxygen or substituted nitrogen; and Q is substituted phenyl having formula (IV):

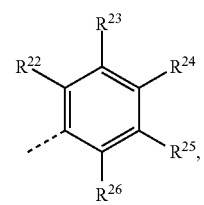

(IV)

wherein each of R²², R²³, R²⁴, R²⁵, and R²⁶ is independently H, hydroxy, alkyl, alkenyl, alkynyl, heteroalkyl, cycloalkyl, cycloalkenyl, cycloalkynyl, aryl, alkylaryl, arylalkyl, heterocyclyl, alkoxy, alkoxyalkyl, alkoxyalkoxy, acyl, alkylcarbonylalkyl, halogenated alkylcarbonylalkyl such as trifluoromethylcarbonylalkyl, aminoalkyl, carboxyalkyl, thiol, alkylthio, amino, alkylamino, dialkylamino, alkoxycarbonyl, alkoxycarbonylalkyl, aminocarbonyl, alkylaminocarbonyl, dialkylaminocarbonyl, or arylcarboxamido, the alkyl or aryl of which is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—$SO_3H$), sulfonate ester (—$SO_3R^{15}$), or sulfonamide (—$SO_2NR^{15}R^{16}$); or $R^{22}$ and $R^{23}$ together, $R^{23}$ and $R^{24}$ together, $R^{24}$ and $R^{25}$ together, or $R^{25}$ and $R^{26}$ together form a part of a 5- or 6-membered cycloalkyl, heterocyclyl, aryl or heteroaryl ring fused with the phenyl ring of formula (IV) that is optionally further substituted by one or more F, Cl, Br, I, a carboxylic acid, a salt of carboxylic acid, a carboxylic acid ester of an alcohol, amino, alkylamino, dialkylamino, alkoxy, thiol, alkylthio, alkyltriphenylphosphonium, sulfonic acid (—$SO_3H$), sulfonate ester (—$SO_3R^{15}$), or sulfonamide (—$SO_2NR^{15}R^{16}$).

In certain embodiments, Q is substituted phenyl, which can be oxidized by certain reactive oxygen or nitrogen species, such as peroxynitrite and hypochlorous acid, to release highly fluorescent fluorophores. In one embodiment, one of $R^{22}$, $R^{24}$, or $R^{26}$ is such a group that can react with peroxynitrite effectively and selectively. In certain specific embodiments, one of $R^{22}$, $R^{24}$, or $R^{26}$ is $OR^{27}$, $CH_2CH_2COR^{28}$, or $NR^{29}R^{30}$; wherein $R^{27}$ is hydrogen or a group selected from alkyl, alkoxyalkyl, alkanoyl, and polyether; $R^{28}$ is an electron-withdrawing group selected from $CF_3$, halogen-substituted lower alkyl (e.g., $CF_nH_{3-n}$, wherein n is 1, 2, or 3), or (C=O)—O—$W_1$, wherein $W_1$ is a group selected from alkyl, alkenyl, alkynyl, cycloalkyl, cycloalkenyl, cycloalkynyl, aryl, alkaryl or arylalkyl; $R^{29}$ and $R^{30}$ are independently hydrogen or a group selected from hydrogen or a group selected from alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether. Preferably, $R^{24}$ is a group that can react with peroxynitrite effectively and selectively, such as $OR^{27}$, $CH_2CH_2COR^{28}$, or $NR^{29}R^{30}$. In a preferred embodiment, $R^{24}$ is $CH_2CH_2CF_3$, $CH_2CH_2COCOOMe$, or OH.

In a preferred embodiment, $R^1$ of formula (I) or (II) is $CH_3$.

In one embodiment, the fluorogenic or fluorescent compounds of the invention substantially react with peroxynitrite to generate highly fluorescent N-dearylated product (I') or (II') shown as follows, along with increase of fluorescence.

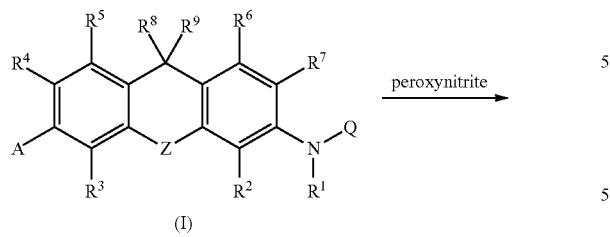

(I)

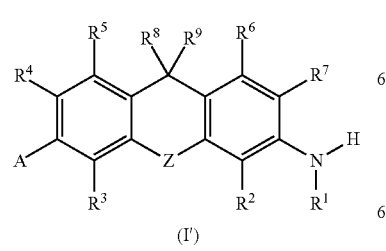

(I')

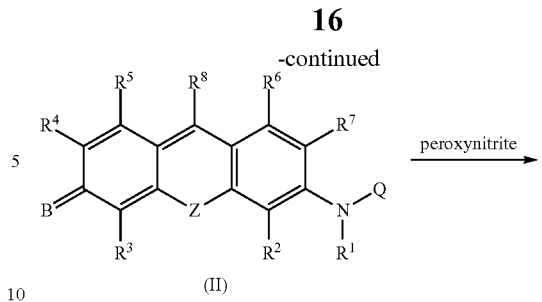

(II)

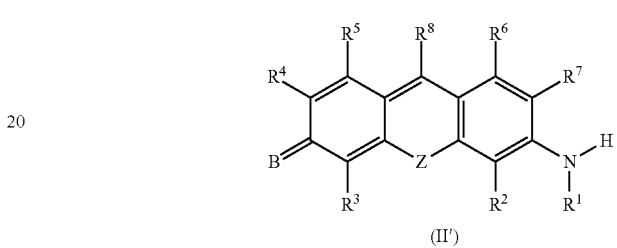

(II')

Green Fluorescent Probes with Improved Intracellular Retention

In certain embodiments, the subject invention provides green fluorogenic or fluorescent compounds with improved intracellular retention, retained sensitivity and selectivity for peroxynitrite detection. In specific embodiments, the green fluorogenic or fluorescent probes with improved intracellular retention provided by the subject invention have the following formula (V)

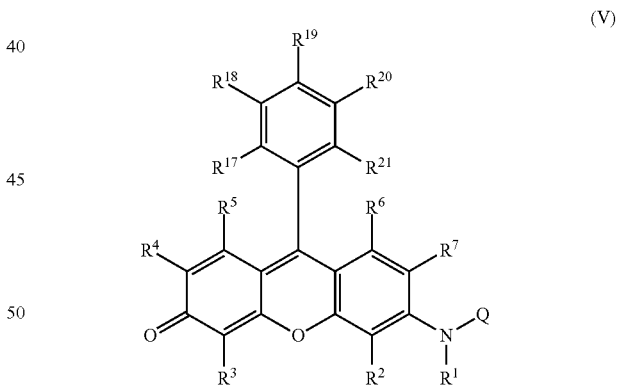

(V)

wherein $R^1$-$R^7$, $R^{17}$-$R^{21}$, and Q are defined as in the formula of (I) or (II). In certain embodiments, at least one of $R^{17}$, $R^{18}$, $R^{19}$, and $R^{20}$ is a carboxyl group. In certain embodiments, $R^{21}$ is H, $CH_3$, OMe, or COOH. In certain embodiments, the carboxyl group(s) on the top phenyl ring of formula (V) is further conjugated with iminodialkylcarboxylic acid(s) ($HN((CH_2)_nCOOH)_2$, n=1, 2, or 3) through amide bond(s).

In certain embodiments, when $R^{21}$ of formula (V) is COOH, the compound has a formula of (V'), and a tautomerization exists between formula (V') and formula (VI) as shown below.

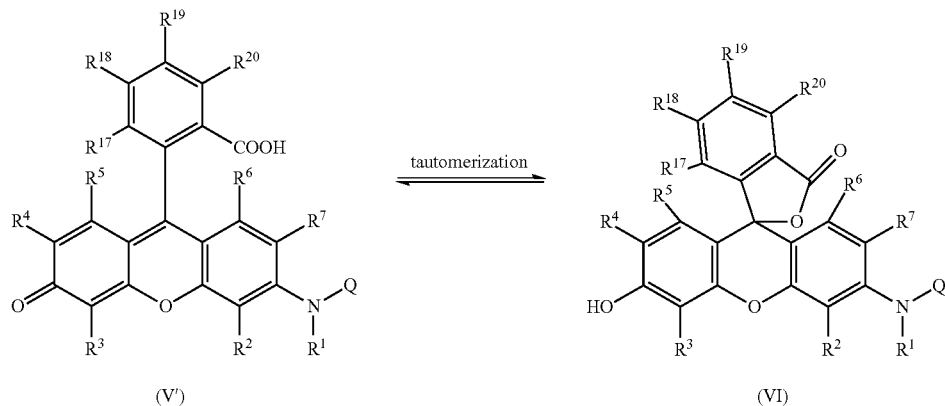

The definitions of substituents ($R^1$-$R^7$, $R^{17}$-$R^{20}$, and Q) in formula (V') and (VI) are the same as those of formula (V).

In certain embodiments, the free carboxyl groups in formula (V), (V') and (VI) are optionally esterified with methyl, ethyl, or acetoxymethyl (AM) groups to render the negatively charged fluorescent probes with cell membrane permeability. In certain embodiments, the free phenolic groups in formula (V), (V') and (VI) are optionally acylated with acetyl, propionyl, or butyryl groups, or protected with acetoxymethyl (AM) groups to render the negatively charged fluorescent probes with cell membrane permeability.

In certain embodiments, $R^2$-$R^7$ of formula (V), (V'), and (VI) are independently H. In certain embodiments, $R^4$ and $R^7$ of formula (V), (V'), and (VI) are F or Cl.

In certain embodiments, $R^{19}$ of formula (V), (V'), and (VI) is a carboxyl or a carboxylic methyl or ethyl ester. In certain embodiments, $R^{19}$ of formula (V), (V'), and (VI) is a carboxyl further conjugated with an iminodialkylcarboxylic acid ($HN((CH_2)_nCOOH)_2$, n=1, 2, or 3) or a dimethyl or diethyl iminodialkylcarboxylate through amide bond.

In specific embodiments, exemplified species of green fluorogenic compounds 1-10 are shown in Scheme 1.

Scheme 1-Green Fluorogenic Compounds for Peroxynitrite Detection

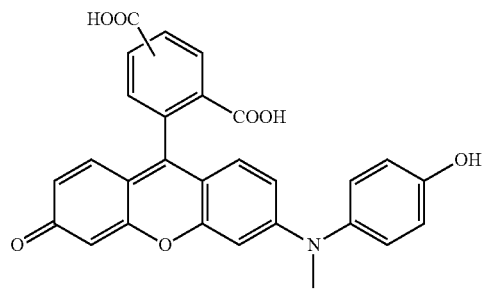

1

-continued

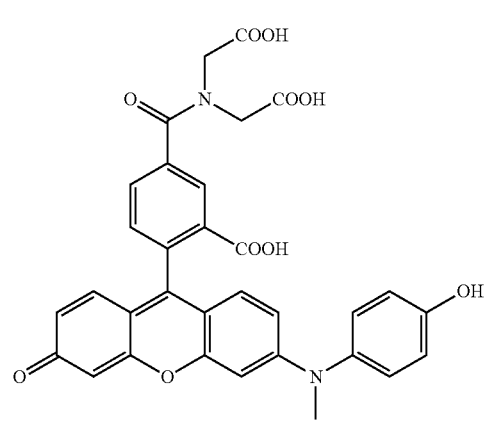

2

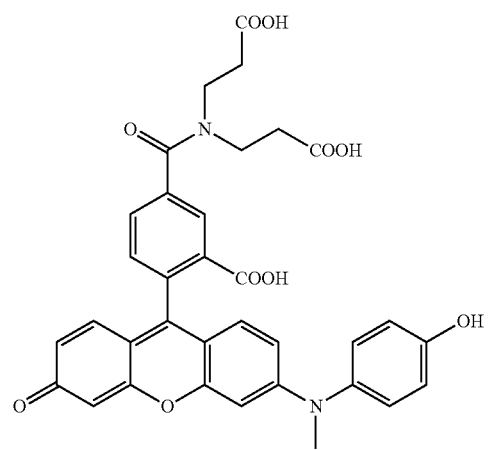

3

-continued

4

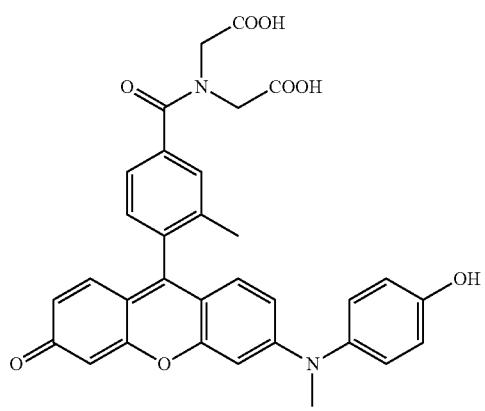

5

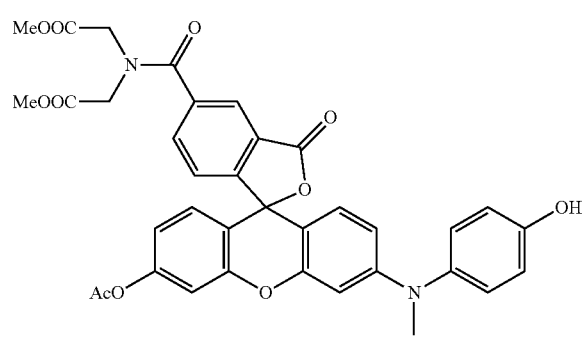

6

7

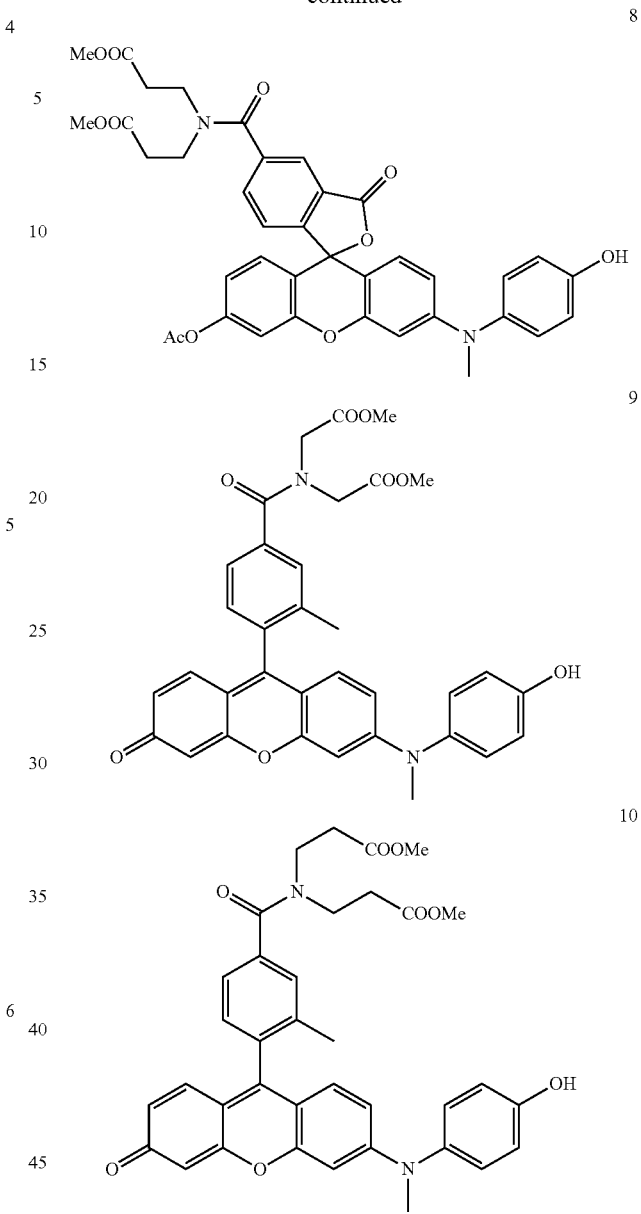

-continued

8

9

10

In one specific embodiment, the subject invention provides green fluorogenic compounds for detection of peroxynitrite in chemical (non-biological) systems, wherein the compounds comprise one or more free carboxylic acid groups. In another specific embodiment, the subject invention provides green fluorogenic compounds for detection of peroxynitrite in in vitro or in vivo biological assays, wherein the compounds comprise one or more ester derivatives of carboxylic acid groups.

For instance, Compounds 1-5, which comprise free carboxylic acids, are preferably used in chemical, non-biological systems, while their corresponding ester derivatives 6-10 are preferably used for biological assays.

Yellow Fluorescent Probes and its Mitochondrial-Targeting Analogs

In certain embodiments, the subject invention provides yellow fluorogenic compounds for peroxynitrite detection.

In specific embodiments, the fluorogenic or fluorescent probes with yellow fluorescence color provided by the subject invention have the following formula (VII)

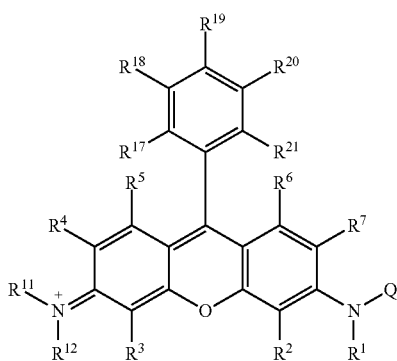

(VII)

wherein $R^1$-$R^7$, $R^{11}$-$R^{12}$, $R^{17}$-$R^{21}$, and Q are defined as in formula (I) or (II).

In certain embodiments, $R^{21}$ is H, CH$_3$, OMe, or COOH.

In certain embodiments, when $R^{21}$ of formula (VII) is COOH, the compound has a formula of (VII'), and a tautomerization exists between formula (VII') and formula (VIII) as shown below.

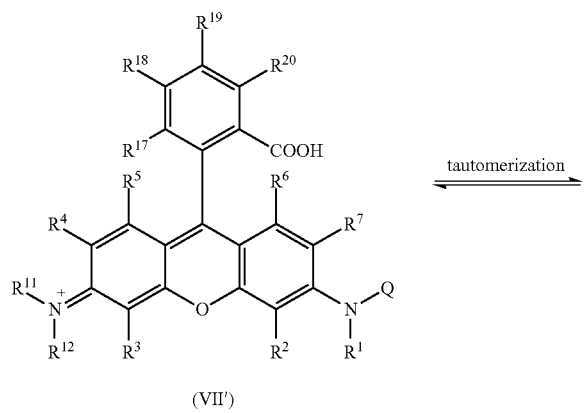

(VII')

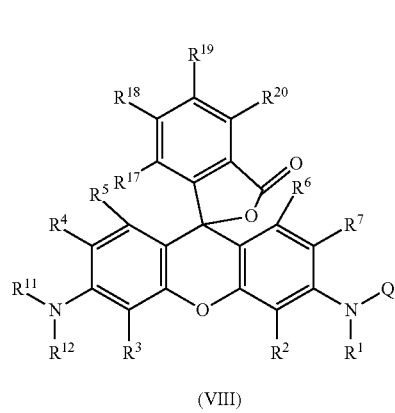

(VIII)

The definitions of substituents ($R^1$-$R^7$, $R^{11}$-$R^{12}$, $R^{17}$-$R^{20}$, and Q) in formula (VII') and (VIII) are the same as those of formula (VII).

In certain embodiments, $R^{11}$ in combination with $R^4$, or $R^{12}$ in combination with $R^3$, or both, form a 5- or 6-membered ring that is saturated or unsaturated, or can be further fused with an aryl or heteroaryl ring, and can be optionally substituted by one or more alkyls, carboxylic acids, sulfonic acids (—SO$_3$H), or their salts, ester or amide derivatives.

In certain embodiments, the free carboxyl groups in formula (VII), (VII') and (VIII) are optionally esterified with methyl, ethyl, or acetoxymethyl (AM) groups to render the negatively charged fluorescent probes with cell membrane permeability.

In certain embodiments, the fluorogenic or fluorescent probes with yellow fluorescence color provided by the subject invention having the formula (VII) can selectively localize to mitochondria of living cells wherein the net charges of the probes having formula (VII) are positive. In these embodiments, $R^{21}$ of formula (VII) is preferably H, CH$_3$, or OMe.

In certain embodiments, when the net charges of the probes having formula (VII) are positive, the positive charges of the probes are balanced by the presence of biologically compatible counterions presented by the symbol Ω. Biologically compatible counterions are well-known in the art, and are herein referred to anions not toxic and deleterious on biomolecules. Non-limiting examples of Ω include chloride, bromide, iodide, sulfate, alkanesulfonate, arylsulfonate, phosphate, perchlorate, tetrafluoroborate, tetraphenylboride, nitrate and anions of aromatic or aliphatic carboxylic acids. Preferred counterions Ω used herein are chloride, iodide, and perchlorate.

In certain embodiments, the mitochondrial-localizing probes having formula (VII) can irreversibly stain mitochondria of living cells wherein at least one of $R^{17}$-$R^{20}$ is an alkylating group (AG). AG is such a reactive site which can react, either directly or through the catalysis of an enzyme, with intracellular nucleophiles, such as glutathione or a cysteine-containing protein to form macromolecular conjugates. Preferably, AG has the formula of CR$^{31}$R$^{32}$X, wherein $R^{31}$ and $R^{32}$ are independently H and CH$_3$, and X is Cl, Br, or I.

In certain embodiments, the fluorogenic or fluorescent probes with yellow fluorescence color provided by the subject invention have the following formula (IX) or (X)

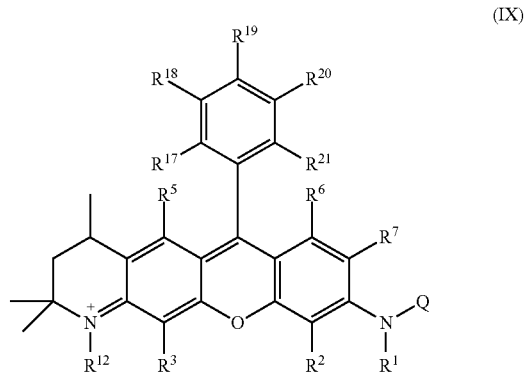

(IX)

-continued

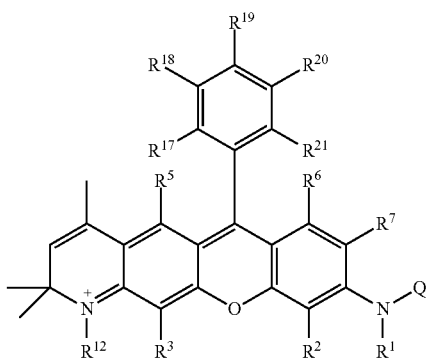

(X)

wherein $R^1$-$R^3$, $R^5$-$R^7$, $R^{11}$-$R^{12}$, $R^{17}$-$R^{21}$, and Q are defined as in formula (I) or (II).

In certain embodiments, $R^{12}$ in formula (IX) and (X) is a $C_{1-10}$ alkyl or alkene. In certain embodiments, $R^{12}$ in formula (IX) and (X) is a $C_{1-10}$ alkyl or alkene substituted with a carboxyl group at the terminal position. In preferred embodiments, $R^{12}$ is ethyl, carboxylmethyl, carboxylethyl, or carboxylpropyl. In certain embodiments, the terminal carboxyl groups in $R^{12}$ of formula (IX) and (X) are esterified with methyl, ethyl, or acetoxymethyl (AM) groups to render the negatively charged fluorescent probes with cell membrane permeability.

In certain embodiments, $R^2$, $R^3$, $R^5$, $R^6$, and $R^7$ in formula (IX) and (X) are independently H. In certain embodiments, $R^7$ in formula (IX) and (X) is F or Cl.

In certain embodiments, $R^{21}$ in formula (IX) and (X) is COOH, H, $CH_3$, or OMe.

In certain embodiments, $R^{17}$, $R^{18}$, $R^{19}$, and $R^{20}$ in formula (IX) and (X) are independently H. In certain embodiments, at least one of $R^{17}$, $R^{18}$, $R^{19}$, and $R^{20}$ in formula (IX) and (X) is an alkylating group, preferably, chloromethyl ($CH_2Cl$).

In specific embodiments, exemplified species of yellow fluorogenic compounds 11-21 are shown in Scheme 2.

Scheme 2-Yellow Fluorogenic Compounds for Peroxynitrite Detection

11

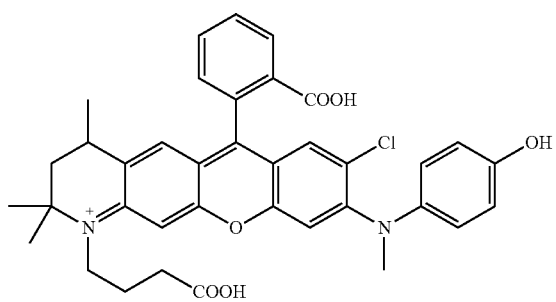

12

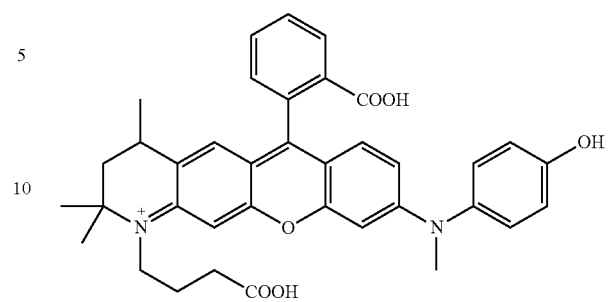

13

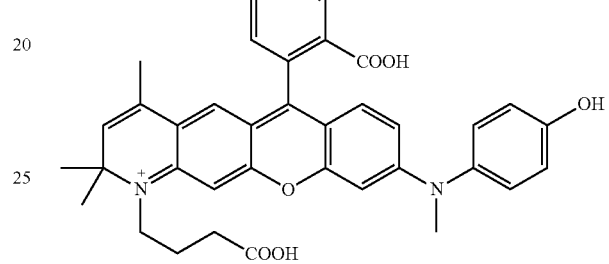

14

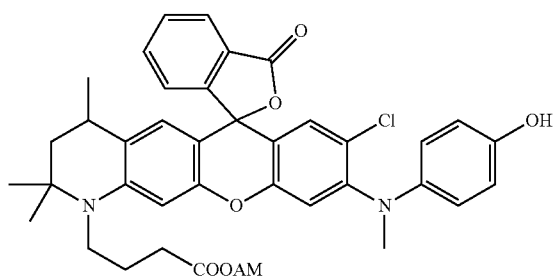

15

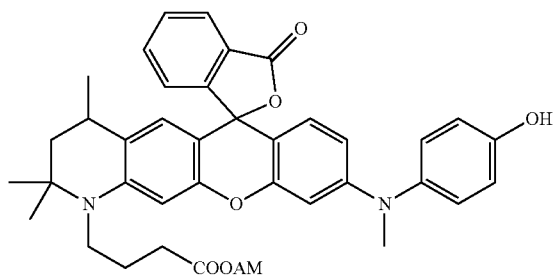

16

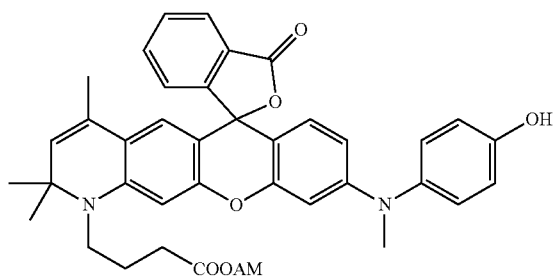

-continued

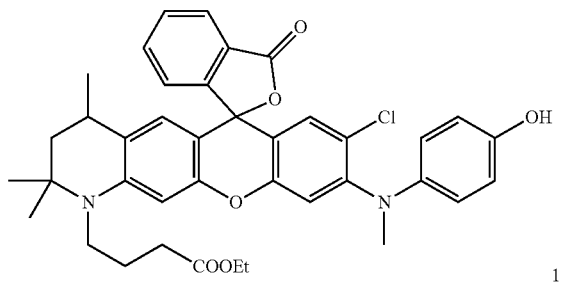

17

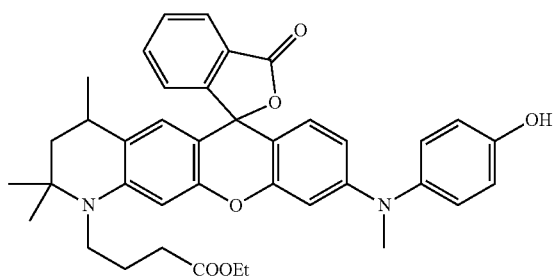

18

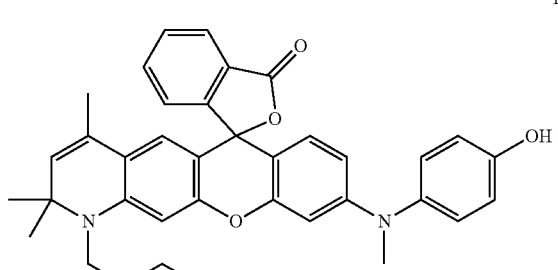

19

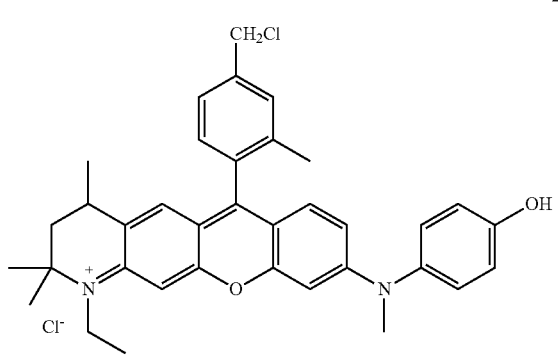

20

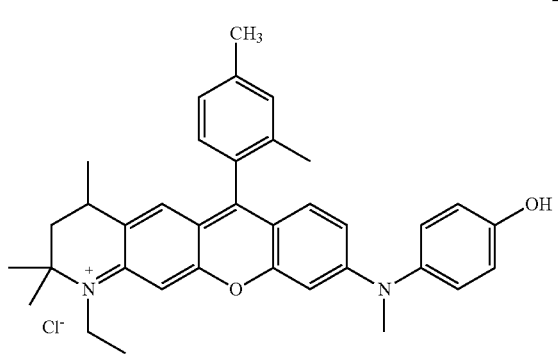

21

AM = CH₂OCOCH₃

The Compounds 11-13 react with peroxynitrite to give strong yellow fluorescence signals with emission maxima at about 570 nm, and exhibit high selectivity towards peroxynitrite over other ROS and RNS in chemical (non-biological) systems.

In one specific embodiment, the subject invention provides yellow fluorogenic compounds for detection of peroxynitrite in chemical (non-biological) systems, wherein the compounds comprise one or more free carboxylic acid groups. In another specific embodiment, the subject invention provides yellow fluorogenic compounds for detection of peroxynitrite in in vitro or in vivo biological assays, wherein the compounds comprise one or more lactone and ester derivatives of carboxylic acid groups.

In still another specific embodiment, the subject invention provides yellow fluorogenic compounds with selective localization in mitochondria of living cells for detection of peroxynitrite in in vitro or in vivo biological assays, wherein the compounds comprise at least one positive net charge.

For instance, Compounds 11-13 are preferably used for detection of peroxynitrite in chemical, non-biological systems; while the corresponding lactone and ester derivatives 14-19 are preferably used for biological assays. The positively charged fluorogenic probes 20-21 are used for detection of peroxynitrite in both non-biological and biological systems. When applied to biological systems for detecting peroxynitrite, the positively charged fluorogenic probes 20-21 are selectively localized to mitochondria of living cells.

Red Fluorescent Probes

In certain embodiments, the subject invention provides red fluorogenic compounds for peroxynitrite detection. The red florescent compounds, which are based on Si-fluorescein scaffold, react with peroxynitrite effectively to provide strong red fluorescence signals with emission maxima at about 620 nm. The red fluorogenic compounds also exhibit high selectivity towards peroxynitrite over other ROS and RNS.

In specific embodiments, the fluorogenic or fluorescent probes with red fluorescence color provided by the subject invention have the following formula (XI)

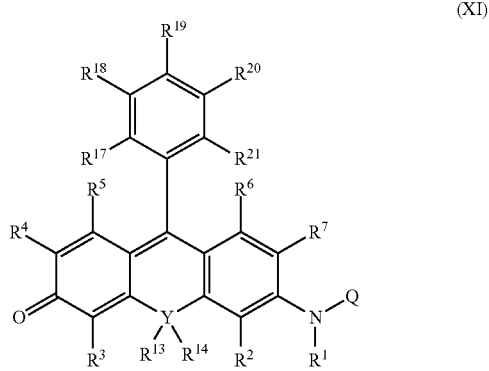

(XI)

wherein $R^1$-$R^7$, $R^{13}$-$R^{14}$, $R^{17}$-$R^{21}$, and Q are defined as in formula (I) or (II); and wherein in certain embodiments, Y is Si, Ge, or Sn. Preferably, $R^{13}$ and $R^{14}$ are independently $CH_3$, or phenyl.

In certain embodiments, at least one of $R^{17}$, $R^{18}$, $R^{19}$, and $R^{20}$ is a carboxyl group. In certain embodiments, $R^{21}$ is H, $CH_3$, OMe, or COOH. In certain embodiments, the carboxyl group(s) on the top phenyl ring of formula (XI) is further conjugated with iminodialkylcarboxylic acid(s) $(HN((CH_2)_nCOOH)_2$, n=1, 2, or 3) through amide bond(s).

In certain embodiments, when $R^{21}$ of formula (XI) is COOH, the compound has a formula of (XI'), and a tautomerization exists between formula (XI') and formula (XII) as shown below.

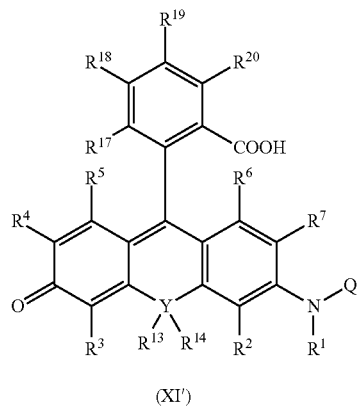

(XI')

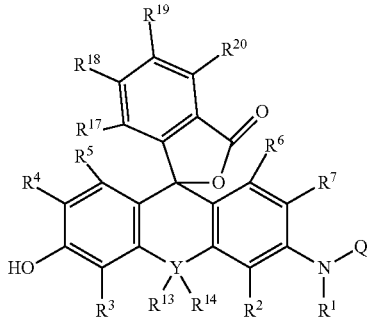

(XII)

The definitions of substituents ($R^1$-$R^7$, $R^{13}$-$R^{14}$, $R^{17}$-$R^{20}$, Y, and Q) in formula (XI') and (XII) are the same as those of formula (XI).

In certain embodiments, the free carboxyl groups in formula (XI), (XI') and (XII) are optionally esterified with methyl, ethyl, or acetoxymethyl (AM) groups to render the negatively charged fluorescent probes with cell membrane permeability. In certain embodiments, the free phenolic groups in formula (XI), (XI') and (XII) are optionally acylated with acetyl, propionyl, or butyryl groups, or protected with acetoxymethyl (AM) groups to render the negatively charged fluorescent probes with cell membrane permeability.

In certain embodiments, $R^2$-$R^7$ of formula (XI), (XI'), and (XII) are independently H. In certain embodiments, $R^4$ and $R^7$ of formula (XI), (XI'), and (XII) are F or Cl.

In certain embodiments, $R^{19}$ of formula (XI), (XI'), and (XII) is a carboxyl or a carboxylic methyl or ethyl ester. In certain embodiments, $R^{19}$ of formula (XI), (XI'), and (XII) is a carboxyl further conjugated with an iminodialkylcarboxylic acid ($HN((CH_2)_nCOOH)_2$, n=1, 2, or 3) or a dimethyl or diethyl iminodialkylcarboxylate through amide bond.

In specific embodiments, exemplified species of red fluorogenic compounds 22-24 are shown in Scheme 3.

Scheme 3-Red Fluorogenic Compounds for Peroxynitrite Detection

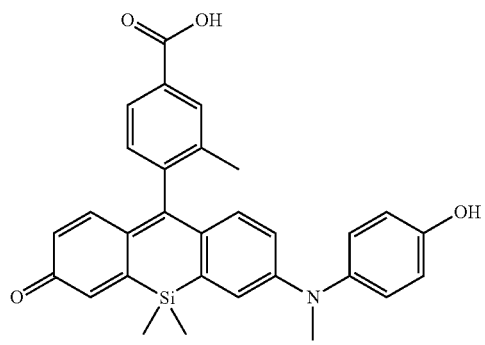

22

-continued

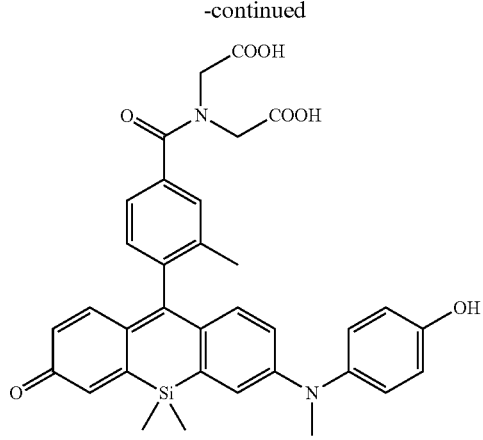

23

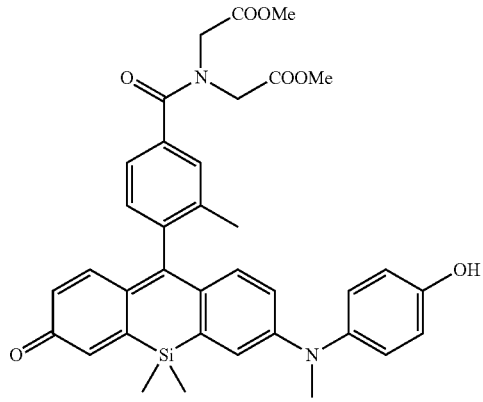

24

In one specific embodiment, the subject invention provides red fluorogenic compounds for detection of peroxynitrite in chemical (non-biological) systems, wherein the compounds comprise one or more free carboxylic acid groups. In another specific embodiment, the subject invention provides red fluorogenic compounds for detection of peroxynitrite in in vitro or in vivo biological assays, wherein the compounds comprise one or more ester derivatives of carboxylic acid groups.

For instance, Compounds 22-23, which comprise free carboxylic acids, are preferably used in chemical, non-biological systems, while their corresponding ester derivatives 24 are preferably used for biological assays.

Far-Red Fluorescent Probes and its Mitochondrial-Targeting Analogs

In certain embodiments, the subject invention provides far-red fluorogenic compounds for peroxynitrite detection.

In specific embodiments, the fluorogenic or fluorescent probes with far-red fluorescence color provided by the subject invention have the following formula (XIII)

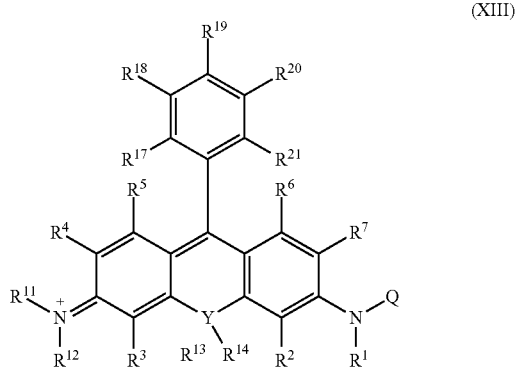

(XIII)

wherein $R^1$-$R^7$, $R^{11}$-$R^{14}$, $R^{17}$-$R^{21}$, and Q are defined as in formula (I) or (II); and wherein in certain embodiments, Y is Si, Ge, or Sn. Preferably, $R^{13}$ and $R^{14}$ are independently $CH_3$, or phenyl.

In certain embodiments, $R^{21}$ is H, $CH_3$, OMe, or COOH.

In certain embodiments, when $R^{21}$ of formula (XIII) is COOH, the compound has a formula of (XIII'), and a tautomerization exists between formula (XIII') and formula (XIV) as shown below.

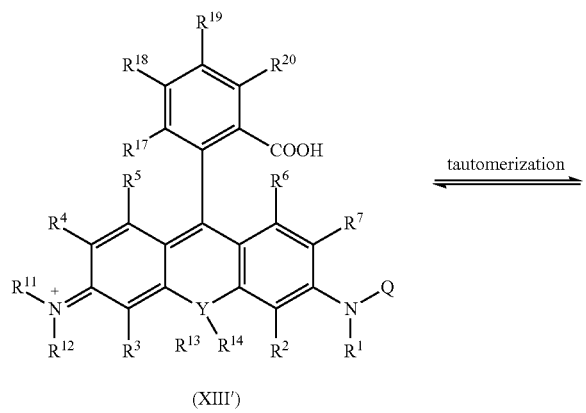

(XIII')

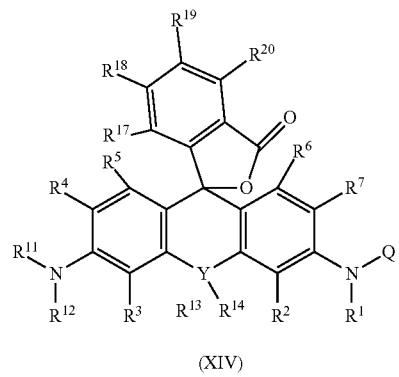

(XIV)

The definitions of substituents ($R^1$-$R^7$, $R^{11}$-$R^{14}$, $R^{17}$-$R^{20}$, Y, and Q) in formula (XIII') and (XIV) are the same as those of formula (XIII).

In certain embodiments, $R^{11}$ in combination with $R^4$, or $R^{12}$ in combination with $R^3$, or both, form a 5- or 6-membered ring that is saturated or unsaturated, or can be further fused with an aryl or heteroaryl ring, and can be optionally substituted by one or more alkyls, carboxylic acids, sulfonic acids (—$SO_3H$), or their salts, ester or amide derivatives.

In certain embodiments, the free carboxyl groups in formula (XIII), (XIII') and (XIV) are optionally esterified with methyl, ethyl, or acetoxymethyl (AM) groups to render the negatively charged fluorescent probes with cell membrane permeability.

In certain embodiments, the fluorogenic or fluorescent probes with far-red fluorescence color provided by the subject invention having the formula (XIII) can selectively localize to mitochondria of living cells when the net charges of the probes having formula (XIII) are positive. In further embodiments, $R^{21}$ of formula (XIII) is preferably H, $CH_3$, or OMe. In certain embodiments, when the net charges of the probes having formula (XII) are positive, the positive charges of the probes are balanced by the presence of biologically compatible counterions presented by the symbol Ω. Biologically compatible counterions are well-known in the art, and are herein referred to anions not toxic and deleterious on biomolecules. Non-limiting examples of Ω include chloride, bromide, iodide, sulfate, alkanesulfonate, arylsulfonate, phosphate, perchlorate, tetrafluoroborate, tetraphenylboride, nitrate and anions of aromatic or aliphatic carboxylic acids. Preferred counterions Ω used herein are chloride, iodide, and perchlorate.

In certain embodiments, the mitochondrial-localizing probes having formula (XIII) can irreversibly stain mitochondria of living cells wherein at least one of $R^{17}$-$R^{20}$ is an alkylating group (AG). AG is such a reactive site which can react, either directly or through the catalysis of an enzyme, with intracellular nucleophiles, such as glutathione or a cysteine-containing protein to form macromolecular conjugates. Preferably, AG has the formula $CR^{31}R^{32}X$, wherein $R^{31}$ and $R^{32}$ are independently H and $CH_3$, and X is Cl, Br, or I.

In certain embodiments, the fluorogenic or fluorescent probes with far-red fluorescence color provided by the subject invention have the following formula (XV) or (XVI)

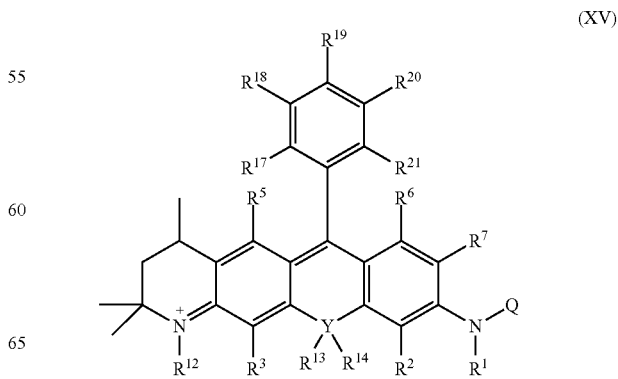

(XV)

-continued

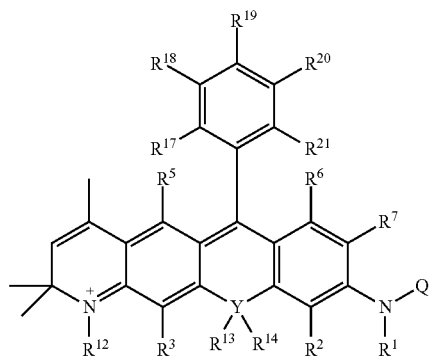

(XVI)

wherein $R^1$-$R^3$, $R^5$-$R^7$, $R^{13}$-$R^{14}$, $R^{17}$-$R^{21}$, and Q are defined as in formula (I) or (II), and wherein in certain embodiments, Y is Si, Ge, or Sn.

In certain embodiments, $R^{12}$ in formula (XV) and (XVI) is a $C_{1-10}$ alkyl or alkene. In certain embodiments, $R^{12}$ in formula (XV) and (XVI) is a $C_{1-10}$ alkyl or alkene substituted with a carboxyl group at the terminal position. In preferred embodiments, $R^{12}$ is ethyl, carboxylmethyl, carboxylethyl, or carboxylpropyl. In certain embodiments, the terminal carboxyl groups in $R^{12}$ of formula (XV) and (XVI) are esterified with methyl, ethyl, or acetoxymethyl (AM) groups to render the negatively charged fluorescent probes with cell membrane permeability.

In certain embodiments, $R^2$, $R^3$, $R^5$, $R^6$, and $R^7$ in formula (XV) and (XVI) are independently H. In certain embodiments, $R^7$ in formula (XV) and (XVI) is F or Cl.

In certain embodiments, $R^{21}$ in formula (XV) and (XVI) is COOH, H, $CH_3$, or OMe.

In certain embodiments, $R^{17}$, $R^{18}$, $R^{19}$, and $R^{20}$ in formula (XV) and (XVI) are independently H. In certain embodiments, at least one of $R^{17}$, $R^{18}$, $R^{19}$, and $R^{20}$ in formula (XV) and (XVI) is an alkylating group, preferably, chloromethyl ($CH_2Cl$).

In specific embodiments, exemplified species of far-red fluorogenic compounds 25-29 are shown in Scheme 4.

Scheme 4-Far-red Fluorogenic Compounds for Peroxynitrite Detection

25

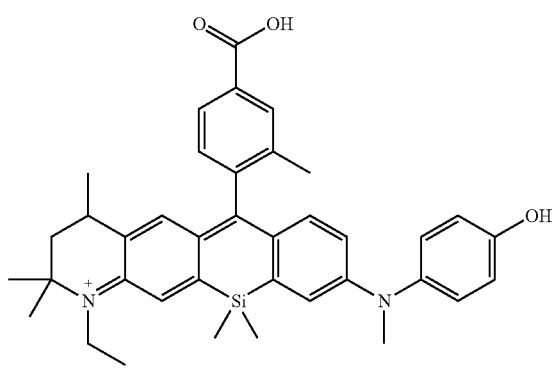

26

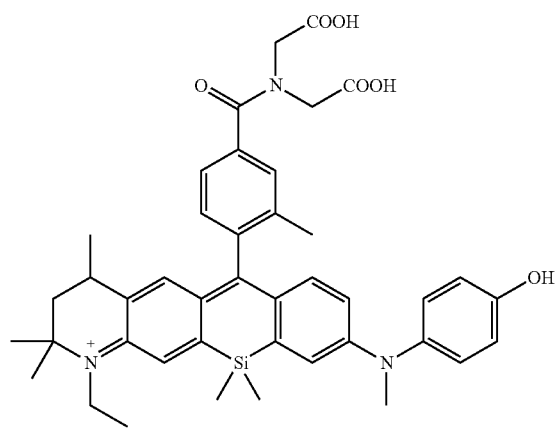

27

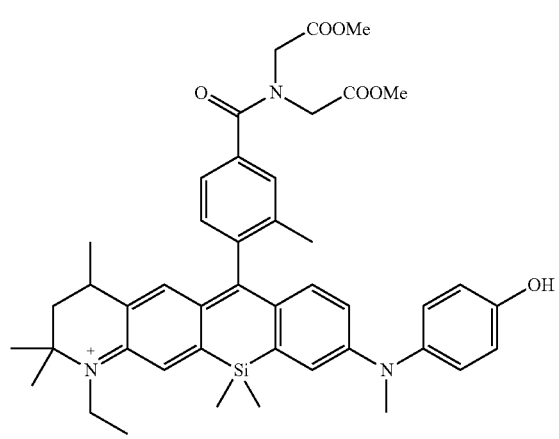

28

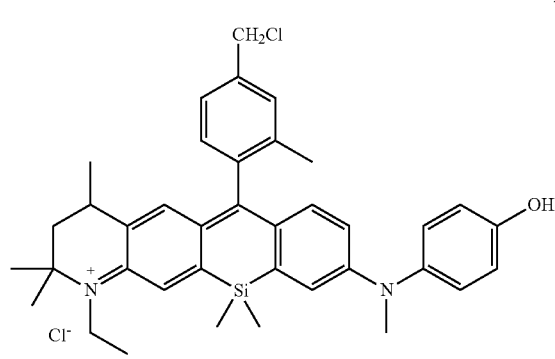

29

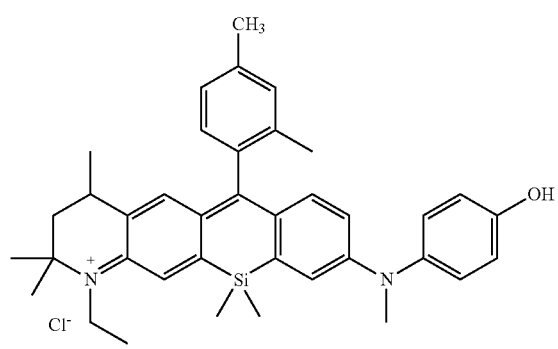

In one specific embodiment, the subject invention provides far-red fluorogenic compounds for detection of peroxynitrite in chemical (non-biological) systems, wherein the compounds comprise one or more free carboxylic acid groups. In another specific embodiment, the subject invention provides far-red fluorogenic compounds for detection of peroxynitrite in in vitro or in vivo biological assays, wherein the compounds comprise one or more lactone and ester derivatives of carboxylic acid groups.

In still another specific embodiment, the subject invention provides far-red fluorogenic compounds with selective localization in mitochondria of living cells for detection of peroxynitrite in in vitro or in vivo biological assays, wherein the compounds comprise at least one positive net charge.

For instance, the fluorogenic compounds 25-26 shown in Scheme 4 can be used in chemical (non-biological) systems for detection of peroxynitrite. In another specific embodiment, the positively charged fluorogenic compounds 27-29 can be used for detection of peroxynitrite in in vitro or in vivo biological assays. In still another specific embodiment, the subject invention provides far-red fluorogenic compounds 28-29 with selective localization in mitochondria of living cells for detection of peroxynitrite in in vitro or in vivo biological assays, wherein the compounds comprise at least one positive net charge after entering into the cells.

Mitochondrial-Targeting Fluorescent Probes

Mitochondria are the primary generators and targets of reactive oxygen species (ROS) including peroxynitrite. Development of mitochondrial-targeting fluorogenic probes for peroxynitrite detection is therefore important for elucidating and understanding the generation, metabolism, and biological effects of peroxynitrite. In addition, mitochondrial-targeting probes facilitate the accumulation of probes in mitochondria, and therefore efficiently avoid the probe leakage problem.

One method for targeting molecules to mitochondria of living cells is to conjugate the molecules with triphenylphosphonium (TPP) head groups, which possess one positive charge and large hydrophobic surface area. The resulting conjugates can be attracted by the negative potential across the inner mitochondrial membrane, and therefore be accumulated several-hundred folds into mitochondria.

In certain embodiments, the subject invention provides fluorogenic compounds for targeting mitochondria and simultaneously detecting peroxynitrite. The mitochondrial-targeted compounds exhibit retained sensitivity and selectivity for peroxynitrite detection, and selectively stain peroxynitrite in mitochondria of living cells.

In certain embodiments, the above stated fluorogenic probes for detection of peroxynitrite can be made to selectively target mitochondria of living cells by conjugating the probes with positively charged triphenylphosphonium moieties at the free carboxyl groups of the probes through simple amide bond linkage. In certain embodiments, the linkages between the probes and the triphenylphosphonium moieties have the following formula (XVII) or (XVIII)

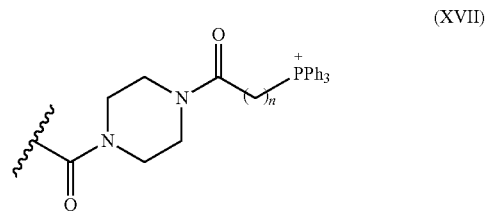

(XVII)

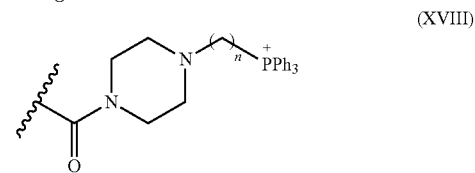

(XVIII)

wherein n=1, 2, 3, 4, 5, 6, 7, 8, 9, or 10.

In certain embodiments, the triphenylphosphonium moieties can be conjugated to the fluorogenic probes at any free carboxyl group of the probes. In specific embodiments, some non-limiting examples of mitochondrial-targeting fluorogenic compounds 30-33 for detection of peroxynitrite are shown in Scheme 5.

Scheme 5-Mitochondrial-Targeting Fluorogenic Compounds for Peroxynitrite Detection

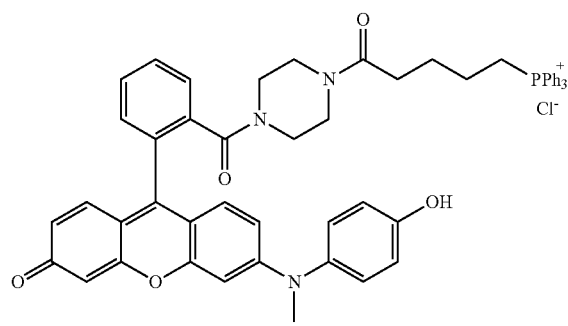

30

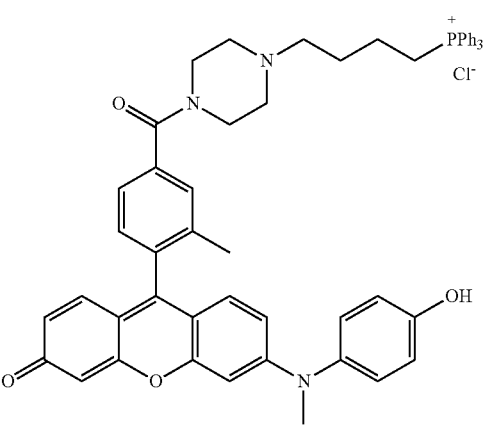

31

-continued

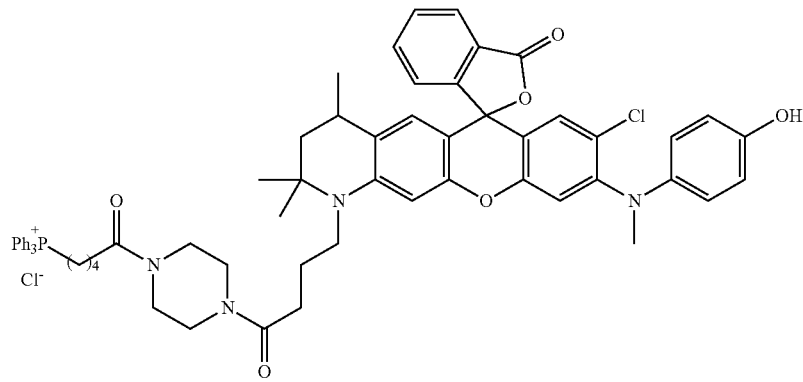

32

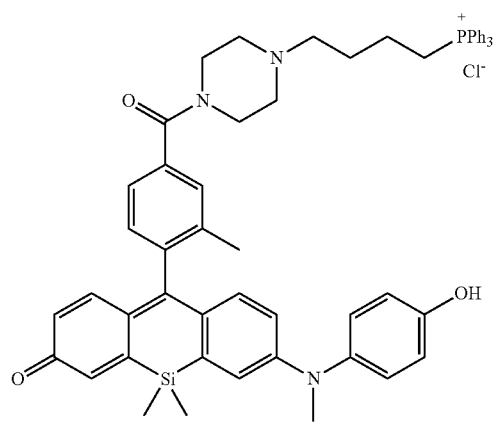

33

In one embodiment, the subject invention does not encompass compounds or fluorogenic compounds and probes that are described in U.S. patent application Ser. No. 12/417,672.

Probe Conjugates

In some embodiments, at least one of the groups of the compounds of formula (I) or (II) is substituted by a reactive group (Rg) or a conjugated group (Cg), wherein Rg or Cg is optionally attached to the aromatic amine compounds disclosed herein through a linkage group, -L-. In other embodiments, at least one of the groups of the compounds disclosed herein is substituted by an -L-Rg or -L-Cg group.

In some embodiments, L is or comprises a bond or a linking group such as O, S, an aminylene group (e.g., an NR group where R is H, an alkyl group, an alkenyl group, an alkynyl group, a carboxyl group, an acyl group, an aromatic group, or a heterocyclic group), a sulfonyl group, an organic linking group, or a combination thereof. The organic linking group disclosed herein may be a divalent linking organic group connecting any of two fragments.

Some non-limiting examples of the divalent organic linking group include a carbonyl group, an alkylene group, an arylene group, a divalent heterocyclic group, and combinations thereof. Another non-limiting example of the divalent organic linking group includes a —$(CH_2)_m$— group, where m is an integer between 1 and 50, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, a $SiR_eR_f$ group, a $BR_g$ group, or a P(=O)$R_h$ group, where $R_a$, $R_b$, $R_c$, $R_d$, $R_e$, $R_f$, $R_g$, and $R_h$ are, each independently, a bond, H, a hydroxyl group, a thiol group, a carboxyl group, an amino group, a halogen, an acyl group, an alkoxy group, an alkylsulfanyl group, an alkenyl group, such as a vinyl group, an allyl group, and a 2-phenylethenyl group, an alkynyl group, a heterocyclic group, an aromatic group, a part of a ring group, such as cycloalkyl groups, heterocyclic groups, and a benzo group, or an alkyl group where one or more of the hydrogens of the alkyl group is optionally replaced by an aromatic group, a hydroxyl group, a thiol group, a carboxyl group, an amino group, or a halogen. A non-limiting example of the aminylene group includes an NR group where R is H, an alkyl group, an alkenyl group, an alkynyl group, an acyl group, an aromatic group, and a heterocyclic group.

In certain embodiments, the organic linking group may have a valence of 3 or more and, therefore, may link any of 3 or more fragments. A non-limiting example of an organic linking group having a valence of 3 is a trivalent organic linking group created by replacing a methylene group in the —$(CH_2)_m$— group with a $CR_b$ group. Another non-limiting example of an organic linking group having a valence of 4 is a tetravalent organic linking group created by replacing a methylene group in the —$(CH_2)_m$— group with a carbon atom.

Another non-limiting example of an organic linking group having a valence of 3 is a trivalent organic linking group created by replacing a methylene group in the —$(CH_2)_m$— group with N, P, or B. A further non-limiting example of an organic linking group having a valence of 4 is a tetravalent organic linking group created by replacing two methylene groups in the —$(CH_2)_m$— group with two $CR_b$ groups. Based on the disclosure herein, a person skill in the art may create an organic linking group having a valence greater than 2 by replacing at least one methylene group in the —$(CH_2)_m$— group with at least an atom or a group having a valence of 3 or more, such as N, P, B, C, Si, a $CR_b$ group, an aromatic group having a valence greater than 2, and a heterocyclic group having a valence greater than 2.

In other embodiments of interest, the organic linking group may comprise at least an unsaturated bond, such as a —$CR_b$=N— bond, a double bond or a triple bond. A non-limiting example of an organic linking group having a double bond is an unsaturated organic linking group created by replacing two adjacent methylene groups in the —$(CH_2)_m$— group with two $CR_b$ groups. The double bond is located between the two adjacent $CR_b$ groups. Another non-limiting example of an organic linking group having a triple bond is an unsaturated organic linking group created by replacing two adjacent methylene groups in the —$(CH_2)_m$— group with two carbon atoms respectively. The triple bond is located between the two adjacent carbon atoms. Another non-limiting example of an organic linking group having a —$CR_b$=N— bond is an unsaturated organic linking group created by replacing two adjacent methylene groups in the —$(CH_2)_m$— group with one $CR_b$ group and an N atom. Based on the disclosure herein, a person skilled in the art may create an organic linking group having at least an unsaturated bond by replacing at least one pair of adjacent methylene groups in the —$(CH_2)_m$— group, each independently, with an atom or a group selected from the group consisting of N, P, B, C, Si, a $CR_b$ group, an aromatic group having a valence greater than 2, and a heterocyclic group having a valence greater than 2.

The compounds having a reactive group (Rg) may comprise a wide variety of organic or inorganic substances that contain or are modified to contain at least one functional group with suitable reactivity toward the Rg group which result in chemical attachment of the reactive group (Rg), represented by -Cv-Rg. In some embodiments, the reactive group (Rg) and functional group are respectively an electrophile and a nucleophile that can react to generate a covalent linkage. The conjugation reaction between the reactive group (Rg) and functional group at the conjugated substance (Cg) results in one or more atoms of the reactive group (Rg) to be incorporated into the linkage, Cv, which attaches the compound with reactive group (Rg) to the conjugated substance (Cg). Some non-limiting examples of the reactive group (Rg) and the respective functional group are listed in Table 1. The tabulation is not meant to be inclusive of chemical reactivity since with the appropriate choice of solvent, co-solvent, stoichiometric ratio, temperature, pressure, reaction time, pH, catalyst and the like, other functional groups can be made to react with the reactive sites disclosed herein whereas the functional groups disclosed herein can be made to react with other reactive sites. Some non-limiting examples of suitable reactive groups (Rg) include acrylamide, acyl azide, acyl halide, nitrile, aldehyde, ketone, alkyl halide, alkyl sulfonate, anhydride, aryl halide, alkyne, alcohol, amine, carboxylic acid, carbodiimide, diazoalkane, epoxide, haloacetamide, hydroxylamine, hydrazine, imido ester, isothiocyanate, maleimide, sulfonate ester or sulfonyl halide.

TABLE 1

| Reactive group (Electrophile) | Functional Group (Nucleophile) | Resulting Linkage |
| --- | --- | --- |
| activated esters (succinimidyl esters) | amines/anilines | amides |
| acrylamides | thiols | thioethers |
| acyl azides | amines/anilines | amides |
| acyl halides | amines/anilines | amides |
| acyl halides | alcohols/phenols | esters |
| acyl nitriles | alcohols/phenols | esters |
| acyl nitriles | amines/anilines | amides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | amides |
| aryl halides | thiols | thiophenols |
| aryl halides | amines | aryl amines |
| alkynes | azides | triazoles |
| alcohols | acid derivatives | esters |
| amines | carboxylic acids | amides |
| amines | halides | alkyl amines |
| amines | aldehydes/ketones | imines |
| carboxylic acids | amines/anilines | amides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioesters |
| haloacetamides | thiols | thioethers |
| hydroxylamines | aldehydes/ketones | oximes |
| hydrazines | aldehydes/ketones | hydrazones |
| imido esters | amines/anilines | amidines |
| isothiocyanates | amines/anilines | thioureas |
| isothiocyanates | alcohols/phenols | isourethanes |
| maleimides | thiols | thioethers |
| maleimides | amines | amines |
| sulfonate esters | amines/anilines | alkyl amines |
| sulfonate esters | thiols | thioesters |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

The reactive group in the compounds disclosed herein is useful for the preparation of any conjugated substance that bears a suitable functional group for covalent linkage of the two. Some non-limiting examples of suitable conjugates include conjugates of antigens, steroids, vitamins, drugs, haptens, metabolites, toxins, amino acids, peptides, nucleotides, oligonucleotides, nucleic acid, carbohydrates, lipids, and so on. Choice of the reactive group used to attach the compounds disclosed herein to the substance to be conjugated typically depends on the functional group on the substance to be conjugated and the type or length of covalent linkage desired. The types of functional groups typically present on the substances include, but are not limited to, amines, thiols, alcohols, phenols, aldehydes, ketones, phosphates, imidazoles, hydrazines, hydroxylamines or a combination of these groups.

Synthesis of Compounds

The fluorogenic or fluorescent compounds of the invention may be made by one skilled in the art with known organic syntheses as well as various general or specific synthetic procedures disclosed herein and in U.S. Pat. Nos. 8,148,423 and 8,114,904, which are herein incorporated by reference in their entireties.

In one embodiment, important steps for the synthesis of the subject compounds (I) and (II) include activation of phenol, typically via triflation, and subsequent amination as shown in Scheme 6 below.

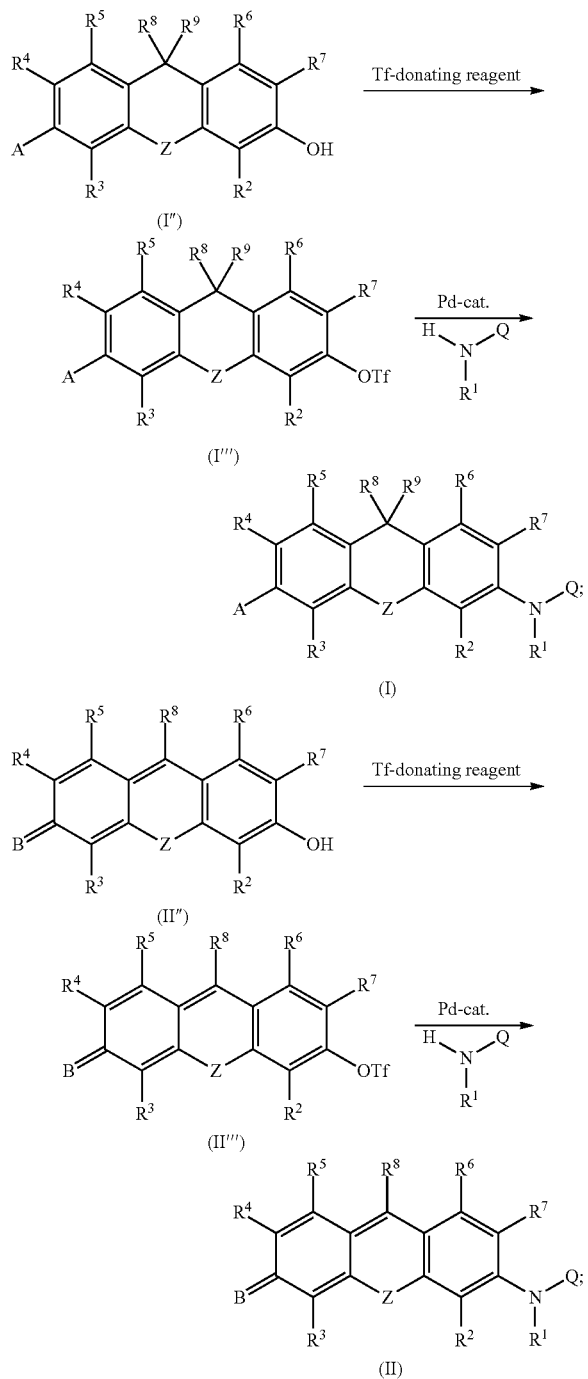

wherein $R^1$-$R^9$, A, B, Z, and Q are defined as in the Compounds (I) and (II); Tf is triflyl; Pd-cat. is palladium-ligand catalysis system for C—N bond formation. Firstly, the phenolic OH group of (I″) or (II″) can be activated by reacting with triflyl-donating reagent, typically triflic anhydride, to form a triflate group. Then the triflate group subsequently undergoes a cross-coupling reaction with an amine having the formula $HNR^1Q$ in the presence of a catalyst, such as a Pd catalyst, to form the subject compound having formula (I) or (II).

Uses of the Probes for Sensitive and Specific Detection of Peroxynitrite

The subject invention also provides use of the compounds as fluorogenic probes for detecting, measuring, and screening peroxynitrite in vitro and/or in vivo. In one embodiment, the subject invention specifically detects peroxynitrite with respect to any other reactive oxygen species and reactive nitrogen species.

In one embodiment, the fluorogenic or fluorescent compounds of the invention sensitively detect peroxynitrite present in aqueous samples at a concentration of lower than 10 μM, or any concentration lower than 10 μM, such as, lower than 8 μM, lower than 6 μM, lower than 4 μM, lower than 2 μM, lower than 1.6 μM, lower than 1.2 μM, lower than 0.8 μM, lower than 0.4 μM, lower than 0.2 μM, lower than 0.1 μM, lower than 0.05 μM, or lower than 0.01 μM, In certain embodiments, the subject invention provides fluorogenic probe compositions, comprising a fluorogenic or fluorescent compound of the invention, and optionally, a carrier, solvent, an acid, a base, a buffer solution, or a combination thereof.

The fluorogenic or fluorescent compounds and probe compositions can be formulated into reagent compositions for measuring, directly or indirectly, peroxynitrite in chemical or biological samples. In a specific embodiment, the fluorogenic or fluorescent compounds and probes are formulated into a fluorogenic cell assay kit.

Also provided herein are methods for detecting the presence of, or measuring the level of, peroxynitrite in a sample. In some embodiments, the methods comprise the steps of (a) contacting a fluorogenic compound or probe disclosed herein with a sample to form a fluorescent compound; and (b) measuring fluorescence property of the fluorescent compound. In some embodiments, the fluorescence properties are measured with methods disclosed herein or any method known to a person skilled in the art.

Also provided herein are high-throughput screening fluorogenic methods for detecting peroxynitrite in samples. In some embodiments, the high-throughput screening fluorogenic methods comprise the steps of (a) contacting a fluorogenic compound or probe disclosed herein with samples to form one or more fluorescent compounds; and (b) measuring fluorescence property of the fluorescent compounds.

Also provided herein are high-throughput methods for screening one or more target compounds that can increase or decrease the level of peroxynitrite. In some embodiments, the high-throughput screening method for detecting peroxynitrite comprises the steps of: (a) contacting a fluorogenic compound or probe disclosed herein with the samples to form one or more fluorescent compounds; and (b) measuring fluorescence property of the fluorescent compounds to determine the amount of peroxynitrite in the samples.

Suitable samples include, but are not limited to, chemical (non-biological) samples and biological samples. Suitable biological samples include, but are not limited to, samples containing unicellular or unicellular organisms, microorganisms, cells, tissues, and organs of living organisms, preferably, of animals including humans.

In some embodiments, the high-throughput methods comprise the steps of (a) contacting a fluorogenic compound or probe disclosed herein with one or more target compounds to form one or more fluorescent compounds; and (b) measuring fluorescence properties of the fluorescent compounds to determine the target compounds quantitatively or qualitatively. In other embodiments, the fluorescence properties are measured with methods disclosed herein or any method known to a person skilled in the art.

In some embodiments, informatics systems can be used and implemented in the high-throughput methods disclosed herein. In other embodiments, the informatics systems provide the software control of the physical devices used in the high-throughput method. In other embodiments, the informatics systems organize electronic data generated by the high-throughput methods. In further embodiments, the informatics systems store electronic data generated by the high-throughput methods.

In certain embodiments, mitochondrial-targeting fluorogenic compounds are utilized for selectively staining peroxynitrite in the mitochondria of cells. In addition, the methods for detecting, measuring, and/or screening peroxynitrite can be performed in vitro or in vivo for studying physiological effects of peroxynitrite.

The applications of fluorogenic compounds also include various well-documented uses such as calorimetric labels for a conjugated substance, or in Fluorescence Resonance Energy Transfer (FRET) technology. Some non-limiting examples of such applications are described in U.S. Pat. No. 6,399,392; and *The Handbook: a Guide to Fluorescent Probes and Labeling Technologies,* 10th Edition, Molecular Probes, 2006, both of which are incorporated herein by reference.

EXAMPLES

Following are examples that illustrate embodiments for practicing the invention. The detailed disclosure falls within the scope of, and serve to exemplify, the synthetic schemes or procedures disclosed herein which form part of this disclosure. These examples, figures and schemes are presented for illustrative purposes only and are not intended to limit the scope of this disclosure. All percentages are by weight and all solvent mixture proportions are by volume unless otherwise noted.

Example 1

Synthesis of Green Fluorogenic Compounds 1, 2, and 10

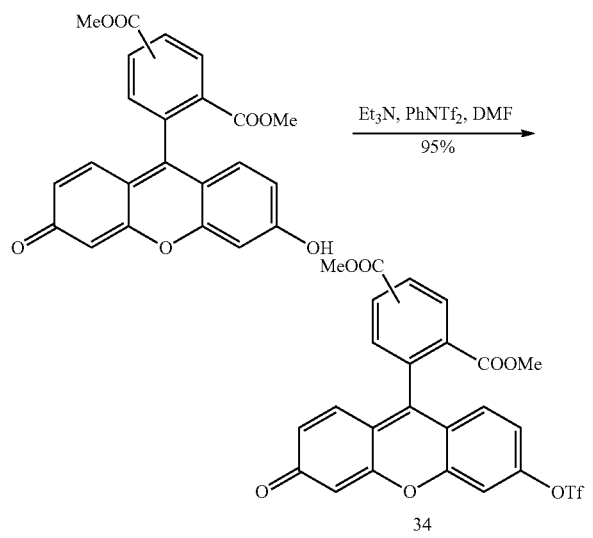

To a solution of the starting phenol (4.3 g, 10.6 mmol) in DMF (30 mL) were added $Et_3N$ (7.5 mL, 53.1 mmol) and N-phenyl-bis(trifluoromethanesulfonimide) (4 g, 11.7 mmol) under Ar at room temperature. The mixture was stirred overnight and then diluted with ethyl acetate (300 mL). The organic solution was washed with HCl solution, water, and dried over anhydrous sodium sulfate, and then concentrated in vacuo. The residue was purified by silica gel column chromatography to give 34 (5.4 g, 95% yield). $^1$H NMR (400 MHz, $CDCl_3$) δ 8.94 (d, J=1.5 Hz, 1H), 8.45 (dd, J=7.9, 1.5 Hz, 1H), 8.41-8.34 (m, 2H), 8.03 (d, J=0.7 Hz, 1H), 7.50 (d, J=7.9 Hz, 1H), 7.44 (d, J=1.8 Hz, 1H), 7.43 (d, J=1.8 Hz, 1H), 7.10 (dd, J=8.8, 1.8 Hz, 1H), 7.08 (dd, J=8.8, 1.8 Hz, 1H), 7.03 (d, J=8.8 Hz, 1H), 7.00 (d, J=8.8 Hz, 1H), 6.85 (d, J=9.8 Hz, 1H), 6.82 (d, J=9.8 Hz, 1H), 6.54 (dd, J=9.8, 1.8 Hz, 1H), 6.52 (dd, J=9.8, 1.8 Hz, 1H), 6.42 (d, J=1.8 Hz, 1H), 6.41 (d, J=1.8 Hz, 1H), 4.05 (s, 3H), 3.98 (s, 2H), 3.76 (s, 3H), 3.74 (s, 2H); $^{13}$C NMR (101 MHz, $CDCl_3$) δ 185.66, 185.64, 165.16, 165.01, 164.67, 164.55, 157.81, 157.73, 152.36, 152.31, 151.18, 146.14, 146.06, 138.04, 134.27, 133.98, 133.75, 133.71, 132.38, 132.16, 131.59, 131.45, 131.08, 130.98, 130.64, 129.90, 129.82, 129.07, 128.95, 120.92, 120.73, 120.61, 118.57 (q, $J_{C-F}$=319.0 Hz), 117.41, 110.35, 110.32, 106.76, 106.73, 52.78, 52.77, 52.74, 52.70; $^{19}$F NMR (376 MHz, $CDCl_3$) δ -72.62, -72.63; LRMS (EI) m/z (%): 536 ($M^+$, 60), 404 (100); HRMS (EI): calcd for $C_{24}H_{15}F_3O_9S$ ($M^+$), 536.0389. found, 536.0385.

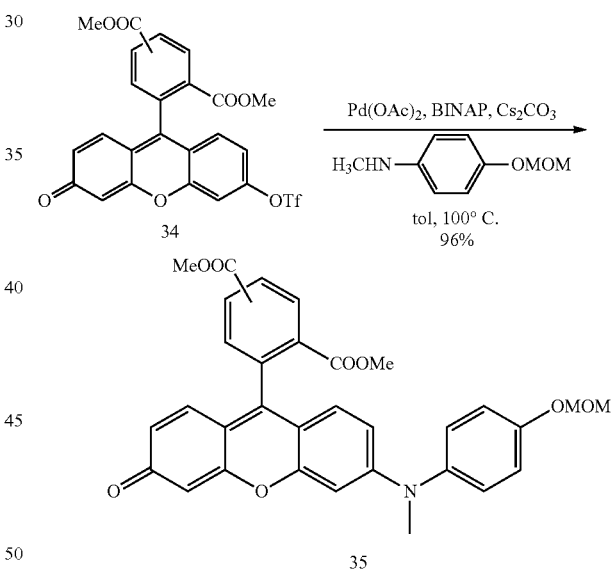

An oven-dried Schlenk tube was charged with $Pd(OAc)_2$ (135 mg, 0.60 mmol), BINAP (751 mg, 1.21 mmol) and $Cs_2CO_3$ (1.44 g, 4.42 mmol), and flushed with Ar gas for 5 min. A solution of 34 (2.16 g, 4.02 mmol) and 4-(methoxymethoxy)-N-methylaniline (705 mg, 4.22 momol) in toluene (20 mL) was added, and the resulting mixture was first stirred under Ar at room temperature for 30 min and then at 100° C. for 20 h. The reaction mixture was allowed to cool to room temperature, diluted with $CH_2Cl_2$ and filtered through a pad of Celite. The filter cake was washed with $CH_2Cl_2$ (3×30 mL). The filtrate was then concentrated and the residue was purified by silica gel column chromatography to give 35 (2.13 g, 96% yield). $^1$H NMR (400 MHz, $CDCl_3$ with 10% $CD_3OD$) δ 8.86 (d, J=1.4 Hz, 1H), 8.36 (dd, J=7.9, 1.4 Hz, 1H), 8.29 (s, 2H), 7.97 (s, 1H), 7.42 (d, J=7.9 Hz, 1H), 7.16 (d, J=8.9 Hz, 4H), 7.12 (d, J=8.9 Hz, 4H), 6.82-6.68 (m, 6H), 6.58-6.47 (m, 6H), 5.21 (s, 4H), 4.03 (s, 3H), 3.95 (s, 3H), 3.69 (s, 3H), 3.67 (s, 3H), 3.51 (s, 6H), 3.41 (s, 6H); $^{13}$C NMR (101 MHz, CDCl$_3$ with 10% CD$_3$OD) δ 184.99, 165.47, 165.33, 165.03, 164.83, 159.19, 159.13, 156.07, 155.11, 155.03, 154.39, 151.11, 151.05, 139.52, 139.16, 134.90, 133.98, 133.61, 133.12, 131.99, 131.50, 131.35, 131.10, 130.93, 130.73, 130.40, 130.03, 129.92, 128.61, 128.48, 128.04, 127.96, 117.71, 115.22, 114.92, 112.27, 112.24, 111.81, 111.56, 105.11, 105.08, 98.52, 98.48, 94.41, 56.06, 52.70, 52.66, 52.59, 40.67; LRMS (EI) m/z (%): 553 (M$^+$, 79), 508 (100); HRMS (EI): calcd for C$_{32}$H$_{27}$NO$_8$ (M$^+$), 553.1737. found, 553.1734.

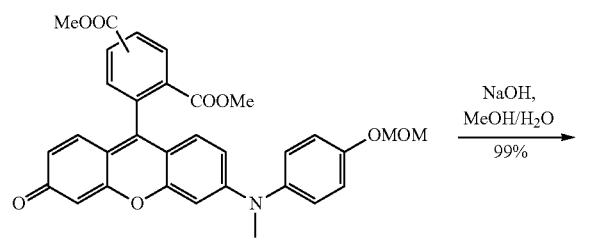

35

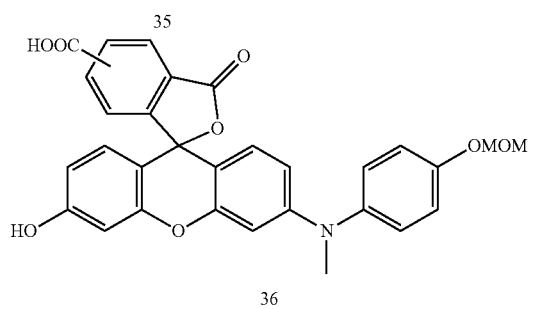

36

To a solution of 35 (2.13 g, 3.85 mmol) in MeOH (30 mL) was added a solution of NaOH (1.54 g, 38.5 mmol) in H$_2$O (15 mL) at room temperature. The resulting solution was stirred at room temperature for 2 hr, and then concentrated in vacuo. The residue was acidified with concentrated HCl. The precipitates were collected by filtration, and dried under reduced pressure to provide the product 36 as a red solid (2.0 g, 99% yield). The crude product was generally pure enough for the next step, and could also be purified by silica gel column chromatography. $^1$H NMR (400 MHz, CD$_3$OD) δ 8.62 (d, J=0.9 Hz, 1H), 8.33 (dd, J=8.0, 0.9 Hz, 1H), 8.29 (dd, J=8.0, 1.3 Hz, 1H), 8.11 (d, J=8.0 Hz, 1H), 7.76 (s, 1H), 7.28 (d, J=8.0 Hz, 1H), 7.14 (d, J=8.9 Hz, 4H), 7.08 (d, J=8.9 Hz, 4H), 6.76-6.67 (m, 4H), 6.67-6.55 (m, 6H), 6.51-6.44 (m, 2H), 5.18 (s, 4H), 3.45 (s, 6H), 3.33 (s, 3H), 3.32 (s, 3H); $^{13}$C NMR (101 MHz, CD$_3$OD) δ 168.81, 166.95, 166.85, 163.42, 162.87, 155.67, 155.58, 154.27, 153.98, 153.92, 153.54, 153.14, 152.35, 147.48, 140.89, 140.71, 136.83, 135.06, 133.16, 132.23, 130.72, 129.39, 129.24, 128.83, 128.69, 128.49, 127.96, 127.47, 127.09, 126.44, 126.22, 125.44, 117.31, 114.20, 113.84, 112.22, 111.85, 111.16, 110.66, 108.95, 108.27, 102.28, 99.29, 99.18, 94.21, 54.82, 39.72, 39.62; LRMS (FAB) m/z (%): 526 (M$^+$, 15).

To a suspension of 36 (2.0 g, 3.73 mmol) in CH$_2$Cl$_2$ (50 mL) were added Et$_3$N (2.6 mL, 18.7 mmol) and acetyl chloride (0.53 mL, 7.46 mmol) successively at 0° C. under Ar. The resulting solution was stirred at room temperature overnight. The reaction mixture was quenched with water and diluted with ethyl acetate. The organic solution was washed with diluted HCl solution and brine, dried over anhydrous sodium sulfate and concentrated. The residue was purified by silica gel column chromatography to give the product 37 (1.55 g, 72% yield). $^1$H NMR (400 MHz, CDCl$_3$) δ 10.27 (s, 2H), 8.74 (s, 1H), 8.36 (dd, J=8.1, 1.3 Hz, 1H), 8.32 (dd, J=8.0, 1.1 Hz, 1H), 8.10 (d, J=8.0 Hz, 1H), 7.91 (s, 1H), 7.28 (d, J=8.1 Hz, 1H), 7.13-7.09 (m, 4H), 7.08-7.02 (m, 6H), 6.77 (s, 4H), 6.56 (d, J=2.5 Hz, 1H), 6.55 (d, J=2.5 Hz, 1H), 6.52 (d, J=2.9 Hz, 1H), 6.50 (d, J=2.9 Hz, 1H), 6.41-6.36 (m, 2H), 5.17 (s, 4H), 3.49 (s, 6H), 3.26 (s, 6H), 2.29 (s, 6H); $^{13}$C NMR (101 MHz, CDCl$_3$) δ 169.85, 169.73, 169.21, 169.18, 168.67, 168.57, 157.76, 155.28, 155.25, 153.34, 152.38, 152.28, 152.22, 151.94, 141.71, 141.66, 136.65, 135.88, 131.67, 131.05, 129.12, 128.45, 128.03, 127.56, 126.21, 125.42, 124.73, 117.74, 117.48, 116.33, 116.26, 115.30, 111.47, 111.42, 110.61, 106.33, 106.22, 100.55, 94.77, 84.12, 83.81, 56.25, 40.60, 21.31.

-continued

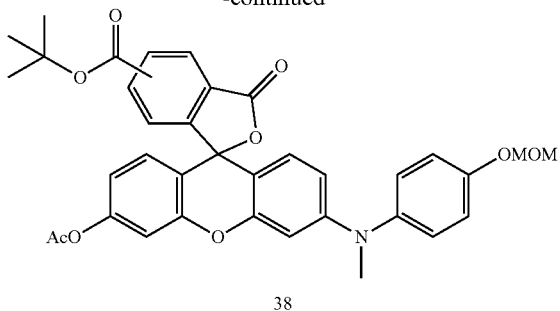

38

To a solution of 37 (170 mg, 0.3 mmol) in anhydrous THF (5 mL) and t-BuOH (1 mL) was added DMAP (96 mg, 0.45 mmol), followed by addition of Boc₂O (0.34 mL, 1.5 mmol) in a drop-wise manner at 0° C. under Ar. The resulting mixture was heated to reflux for 2 hr. After cooled to room temperature, the mixture was diluted with ethyl acetate (50 mL), washed with diluted HCl, H₂O, and brine. The organic solution was dried over anhydrous sodium sulfate and concentrated. The residue was purified by silica gel column chromatography to give the 1:1 ratio of 5'-isomer and 6'-isomer 38.

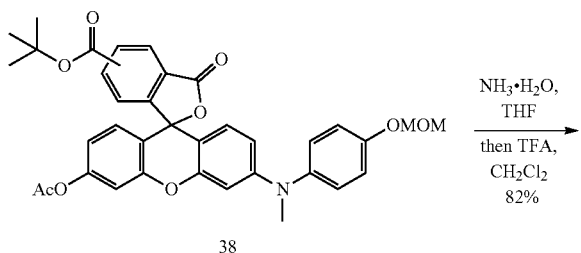

38

NH₃·H₂O, THF
then TFA, CH₂Cl₂
82%

-continued

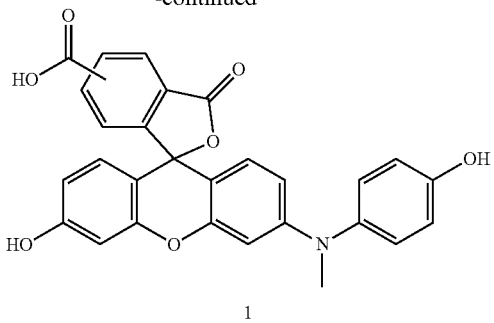

1

To a solution of 38 (50 mg, 0.08 mmol) in THF (2 mL) was added ammonia solution (28%, 5 drops) in a drop-wise manner. The reaction was stirred at room temperature for half an hour, and then acidified with diluted HCl. The reaction mixture was extracted with ethyl acetate. The organic solution was dried over anhydrous sodium sulfate, and concentrated. The resulting residue was re-dissolved in DCM (2 mL), and treated with TFA (2 mL) at room temperature for 2 hr. The mixture was concentrated, and then diluted with saturated NaHCO₃. The mixture was extracted with chloroform with 10% isopropanol three times. The organic solutions were combined, concentrated, and then purified by silica gel column chromatography to give the product 1 (1:1 ratio of 5'-isomer and 6'-isomer, 32 mg, 0.067 mmol, 82% yield).

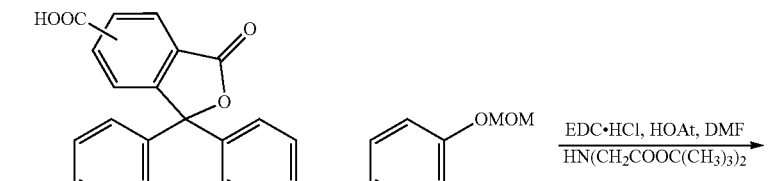

37

EDC·HCl, HOAt, DMF
HN(CH₂COOC(CH₃)₃)₂

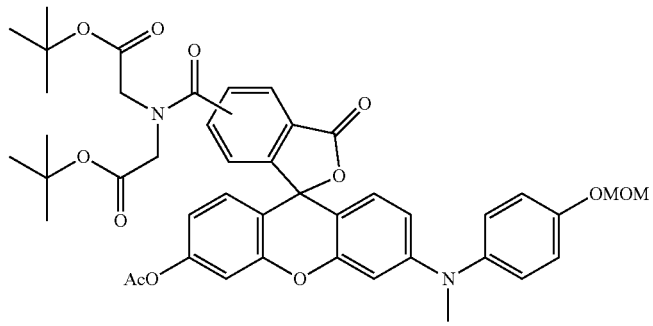

39 5'-isomer, 36%
6'-isomer, 33%

To a solution of 37 (405 mg, 0.71 mmol) in DMF were added di-t-butyl iminodiacetate (524 mg, 2.14 mmol), 1-hydroxy-7-azabenzotriazole (HOAt) (116 mg, 0.86 mmol), and N-(3-dimethylaminopropyl)-N'-ethylcarbodiimide hydrochloride (EDC.HCl) (164 mg, 0.86 mmol) successively under Ar. The reaction mixture was stirred overnight and then diluted with ethyl acetate. The organic layer was washed with saturated NaHCO$_3$ solution followed by 0.1 N HCl and brine. The extracts was dried over anhydrous sodium sulfate, concentrated and purified by silica gel column chromatography to give the 5'-isomer 39 (203 mg, 0.26 mmol, 36% yield) and 6'-isomer (186 mg, 0.23 mmol, 33% yield) separately.

mmol, 76% yield). $^1$H NMR (300 MHz, CD$_3$OD) δ 8.29 (s, 1H), 7.86 (d, J=7.8 Hz, 1H), 7.44 (d, J=7.8 Hz, 1H), 7.15-7.09 (m, 3H), 7.04 (d, J=9.4 Hz, 1H), 7.00 (d, J=2.2 Hz, 1H), 6.93-6.85 (m, 4H), 6.79 (dd, J=9.4, 2.2 Hz, 1H), 4.35 (s, 2H), 4.23 (s, 2H), 3.51 (s, 3H); $^{13}$C NMR (126 MHz, CD$_3$OD) δ 173.09, 172.99, 172.58, 168.33, 168.02, 158.91, 158.70, 158.63, 157.77, 142.16, 138.73, 138.33, 132.77, 132.22, 131.88, 130.38, 129.19, 128.99, 118.08, 117.86, 117.06, 115.28, 114.61, 103.65, 99.30, 53.74, 42.18; LRMS (FAB) m/z (%): 596 (M$^+$, 3); HRMS (FAB): calcd for C$_{32}$H$_{24}$N$_2$O$_{10}$ (M$^+$), 596.1431. found, 596.1433.

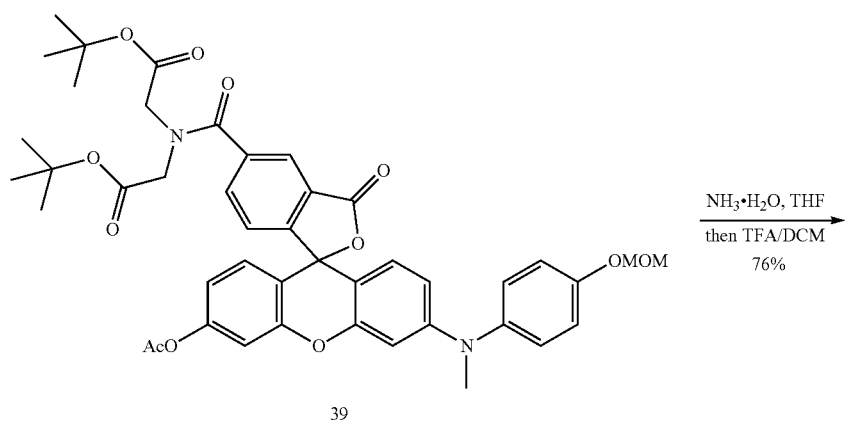

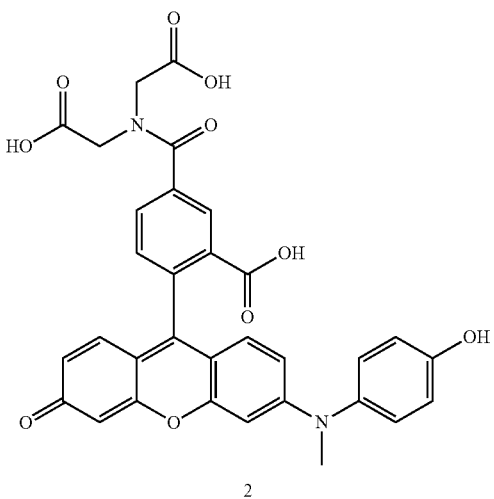

To a solution of 39 (25 mg, 0.031 mmol) in THF (2 mL) was added ammonia solution (28%, 5 drops). The reaction was stirred at room temperature for half an hour, and then acidified with diluted HCl. The reaction mixture was extracted with ethyl acetate. The organic solution was dried over anhydrous sodium sulfate, and concentrated. The resulting residue was re-dissolved in DCM (2 mL), and treated with TFA (2 mL) at room temperature for 2 hr. The solution was concentrated, and then diluted with saturated NaHCO$_3$. The mixture was extracted with chloroform with 10% isopropanol three times. The organic solutions were combined, concentrated, and then purified by silica gel column chromatography to give the product 2 (14 mg, 0.023

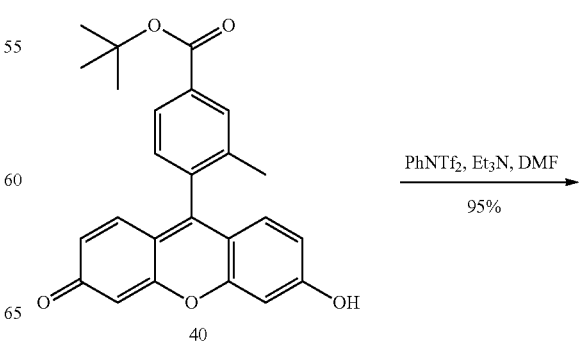

-continued

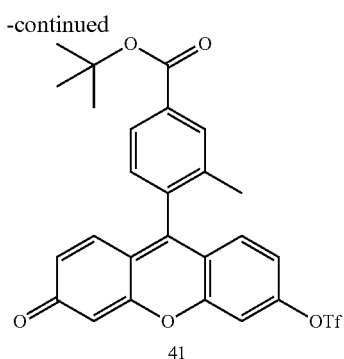

41

To a solution of 40 (500 mg, 1.24 mmol) in DMF (10 mL) were added Et₃N (0.52 mL, 3.72 mmol) and N-phenyl-bis(trifluoromethanesulfonimide) (487 mg, 1.36 mmol) under Ar at room temperature. The mixture was stirred overnight and then diluted with ethyl acetate (50 mL). The organic solution was washed with HCl solution, water, and dried over anhydrous sodium sulfate, and then concentrated in vacuo. The residue was purified by silica gel column chromatography to give the product 41 (630 mg, 95% yield). $^1$H NMR (400 MHz, CDCl₃) δ 8.08 (s, 1H), 8.04 (d, J=7.9 Hz, 1H), 7.45 (s, 1H), 7.31 (d, J=7.9 Hz, 1H), 7.12 (s, 2H), 6.94 (d, J=9.8 Hz, 1H), 6.57 (dd, J=9.8, 1.5 Hz, 1H), 6.43 (d, J=1.5 Hz, 1H), 2.19 (s, 3H), 1.66 (s, 9H); $^{13}$C NMR (101 MHz, CDCl₃) δ 185.72, 164.89, 157.69, 152.76, 151.50, 145.41, 136.63, 135.63, 133.61, 131.77, 131.69, 130.13, 129.50, 129.28, 127.43, 121.60, 120.20, 117.64, 116.87 (q, $J_{C-F}$=320.1 Hz), 110.46, 106.88, 81.68, 28.10, 19.60; $^{19}$F NMR (376 MHz, CDCl₃) δ -72.63; LRMS (EI) m/z (%): 534 (M⁺, 71), 478 (100), 345 (94); HRMS (EI): calcd for C₂₆H₂₁F₃O₇S (M⁺), 534.0960. found, 534.0965.

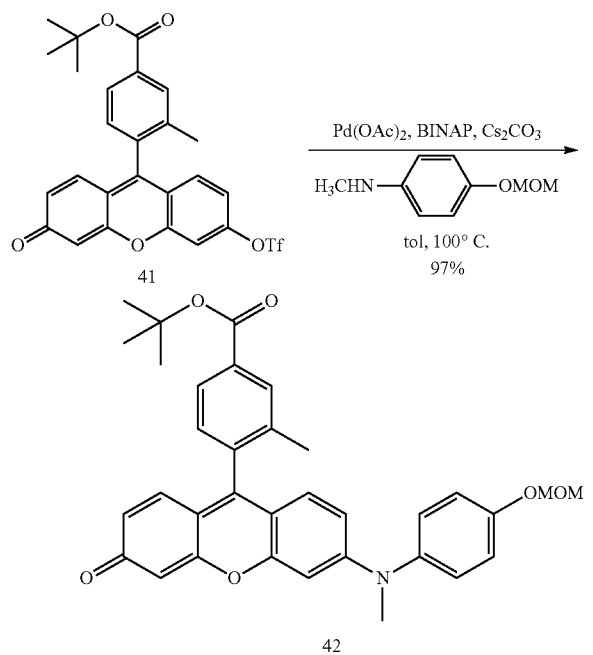

An oven-dried Schlenk tube was charged with Pd(OAc)₂ (24 mg, 0.11 mmol), BINAP (134 mg, 0.21 mmol) and Cs₂CO₃ (257 mg, 0.79 mmol), and flushed with Ar gas for 5 min. A solution of 41 (383 mg, 0.72 mmol) and 4-(methoxymethoxy)-N-methylaniline (126 mg, 0.75 momol) in toluene (10 mL) was added, and the resulting mixture was first stirred under Ar at room temperature for 30 min and then at 100° C. for 20 h. The reaction mixture was allowed to cool to room temperature, diluted with CH₂Cl₂ and filtered through a pad of Celite. The filter cake was washed with CH₂Cl₂ (3×20 mL). The filtrate was then concentrated and the residue was purified by silica gel column chromatography to give the product 42 (386 mg, 0.70 mmol, 97% yield). $^1$H NMR (400 MHz, CD₃OD) δ 7.98 (s, 1H), 7.90 (d, J=8.0 Hz, 1H), 7.18 (d, J=8.0 Hz, 1H), 7.14 (d, J=8.8 Hz, 2H), 7.09 (d, J=8.8 Hz, 2H), 6.85 (d, J=9.4 Hz, 1H), 6.75 (d, J=9.2 Hz, 1H), 6.67 (d, J=2.1 Hz, 1H), 6.57 (dd, J=9.2, 2.1 Hz, 1H), 6.50 (dd, J=9.4, 1.5 Hz, 1H), 6.36 (d, J=1.5 Hz, 1H), 5.17 (s, 2H), 3.43 (s, 3H), 3.39 (s, 3H), 2.00 (s, 3H), 1.60 (s, 9H); $^{13}$C NMR (101 MHz, CD₃OD) δ 185.82, 166.46, 160.83, 157.80, 157.20, 156.95, 154.25, 140.56, 138.12, 137.75, 134.39, 132.32, 131.90, 130.52, 130.35, 129.14, 128.02, 127.96, 118.93, 115.57, 114.57, 112.49, 105.51, 99.19, 95.55, 82.70, 56.36, 41.41, 28.45, 19.67.

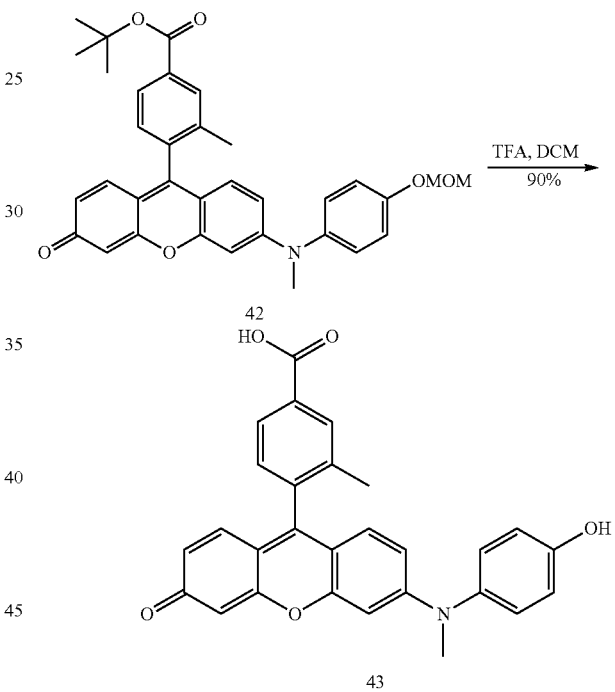

To a solution of 42 (320 mg, 0.58 mmol) in CH₂Cl₂ (3 mL) was added TFA (3 mL). The resulting solution was stirred at room temperature for 2 hr. The solution was concentrated, and then diluted with saturated NaHCO₃. The mixture was extracted with chloroform with 10% isopropanol three times. The organic solutions were combined, dried over anhydrous sodium sulfate, and then concentrated. The residue was purified by silica gel column chromatography to give the product 43 (236 mg, 0.52 mmol, 90% yield). $^1$H NMR (400 MHz, CD₃OD) δ 8.16 (s, 1H), 8.10 (d, J=7.9 Hz, 1H), 7.41 (d, J=7.9 Hz, 1H), 7.31 (d, J=9.1 Hz, 1H), 7.24 (d, J=9.1 Hz, 1H), 7.22-7.18 (m, 3H), 7.11-7.05 (m, 2H), 7.02 (d, J=10.0 Hz, 1H), 6.96 (d, J=8.7 Hz, 2H), 3.66 (s, 3H), 2.11 (s, 3H); $^{13}$C NMR (101 MHz, CD₃OD) δ 170.34, 168.94, 161.12, 161.06, 160.57, 159.31, 159.22, 137.94, 137.28, 136.96, 134.04, 133.00, 132.91, 132.71, 130.48, 128.60, 128.48, 119.64, 119.51, 118.13, 117.37, 116.17, 103.69, 98.81, 42.74, 19.63.

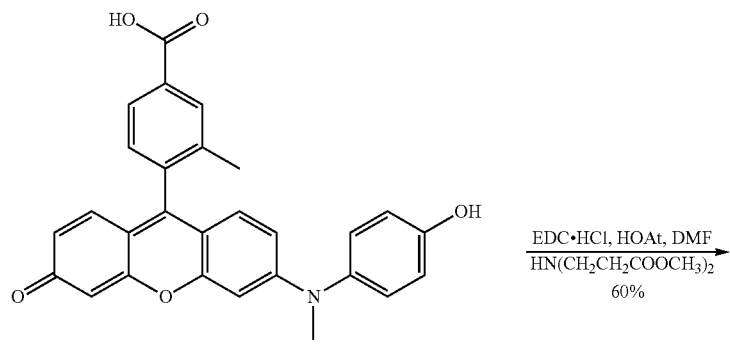

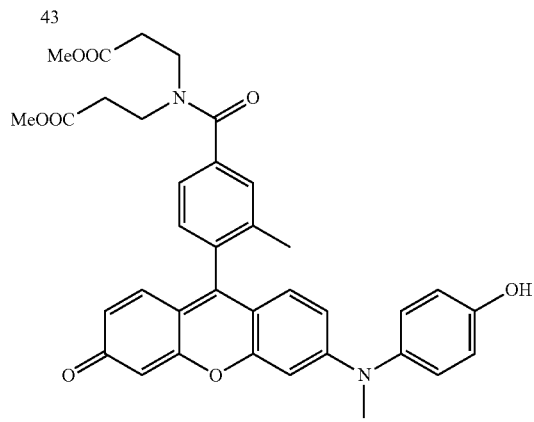

To a solution of 43 (140 mg, 0.31 mmol) in DMF (4 mL) were added dimethyl 3,3'-iminodipropanoate (176 mg, 0.93 mmol), 1-hydroxy-7-azabenzotriazole (HOAt) (70 mg, 0.47 mmol), and N-(3-dimethylaminopropyl)-N'-ethylcarbodiimide hydrochloride (EDC.HCl) (99 mg, 0.47 mmol) successively under Ar. The reaction mixture was stirred overnight and then diluted with ethyl acetate. The organic layer was washed with saturated NaHCO$_3$ solution followed by 0.1 N HCl and brine. The extracts was dried over anhydrous sodium sulfate, concentrated and purified by silica gel column chromatography to give the product 10 (116 mg, 0.19 mmol, 60% yield). $^1$H NMR (400 MHz, CDCl$_3$ with 10% CD$_3$OD) δ 7.40 (s, 1H), 7.36 (d, J=7.7 Hz, 1H), 7.22 (d, J=7.7 Hz, 1H), 7.04 (d, J=8.7 Hz, 2H), 6.99-6.91 (m, 3H), 6.87 (d, J=9.2 Hz, 1H), 6.66-6.57 (m, 3H), 6.55 (s, 1H), 3.74-3.68 (m, 10H), 3.41 (s, 3H), 2.79 (br, 2H), 2.63 (br, 2H), 2.10 (s, 3H); $^{13}$C NMR (101 MHz, CDCl$_3$ with 10% CD$_3$OD) δ 172.47, 171.73, 171.27, 159.54, 156.82, 155.69, 155.47, 151.62, 137.23, 137.12, 134.47, 130.70, 129.52, 129.40, 128.74, 128.07, 127.74, 124.14, 117.12, 115.12, 112.39, 111.38, 105.01, 98.58, 52.07, 45.80, 41.70, 40.91, 33.59, 32.45, 19.65.

Example 2

Synthesis of Yellow Fluorogenic Compound 11

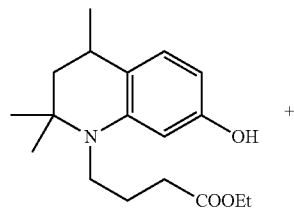

+

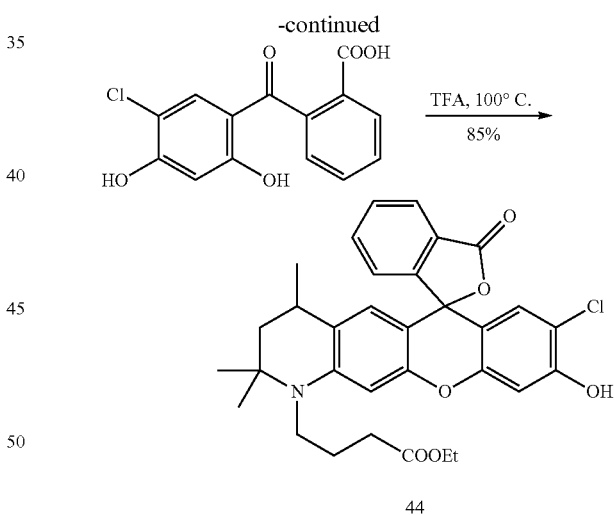

The suspension of the starting materials in TFA was heated to 100° C. for 4 hr in a sealed-tube. The resulting red solution was then concentrated in vacuum and azeotroped with toluene three times to provide the crude product of 44, which was purified by silica gel column chromatography to give the pure product. $^1$H NMR (400 MHz, CDCl$_3$) δ 8.15 (d, J=6.9 Hz, 1H), 7.68-7.61 (m, 2H), 7.22-7.18 (m, 1H), 6.86 (s, 1H), 6.79 (s, 0.5×1H), 6.77 (s, 0.5×1H), 6.56 (s, 1H), 6.48 (s, 1H), 4.22 (br, 1H), 4.20 (q, J=7.0 Hz, 2H), 3.55-3.43 (m, 1H), 3.30-3.17 (m, 1H), 2.80-2.60 (m, 1H), 2.45 (t, J=6.5 Hz, 2H), 2.05-1.88 (m, 2H), 1.69 (d, J=12.9 Hz, 1H), 1.49 (dt, J=20.1, 12.9 Hz, 1H), 1.35 (s, 3H), 1.31 (t, J=7.0 Hz, 3H), 1.21 (s, 3H), 1.07 (d, J=6.3 Hz, 0.5×3H), 0.99 (d, J=6.3 Hz, 0.5×3H).

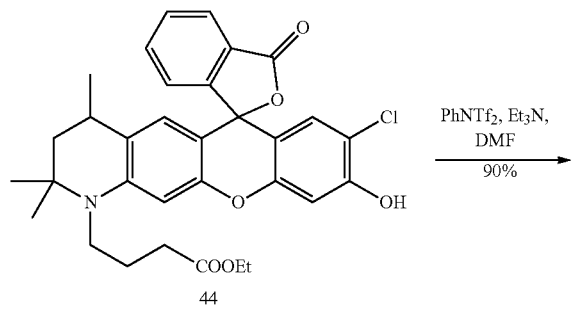

Hz, 0.5×1H), 6.90 (s, 1H), 6.44 (s, 0.5×1H), 6.43 (s, 0.5×1H), 6.40 (s, 1H), 4.22 (t, J=7.1 Hz, 2H), 3.52-3.36 (m, 1H), 3.25-3.10 (m, 1H), 2.78-2.57 (m, 1H), 2.44 (t, J=6.8 Hz, 2H), 2.05-1.96 (m, 2H), 1.74-1.64 (m, 1H), 1.45 (dd, J=24.7, 12.6 Hz, 1H), 1.35-1.30 (m, 6H), 1.17 (s, 3H), 1.06 (d, J=6.6 Hz, 0.5×3H), 0.96 (d, J=6.6 Hz, 0.5×3H); $^{13}$C NMR (101 MHz, CDCl$_3$) δ 173.20, 173.18, 169.11, 169.08, 152.27, 152.05, 151.06, 150.99, 150.69, 150.57, 147.57, 147.37, 145.89, 145.85, 135.43, 135.36, 130.28, 130.23, 130.15, 130.11, 129.69, 126.85, 126.61, 126.54, 126.11, 125.35, 124.68, 124.11, 123.99, 121.43, 121.36, 120.91, 118.67 (q, $J_{C-F}$=318.92 Hz), 112.13, 103.61, 103.60, 97.79, 97.75, 82.73, 82.58, 60.70, 55.19, 55.05, 46.38, 46.29, 44.71, 44.51, 31.67, 31.65, 29.49, 29.36, 26.91, 26.75, 25.74, 25.29, 23.52, 23.36, 19.68, 19.55, 14.34; $^{19}$F NMR (376 MHz, CDCl$_3$) δ −73.17.

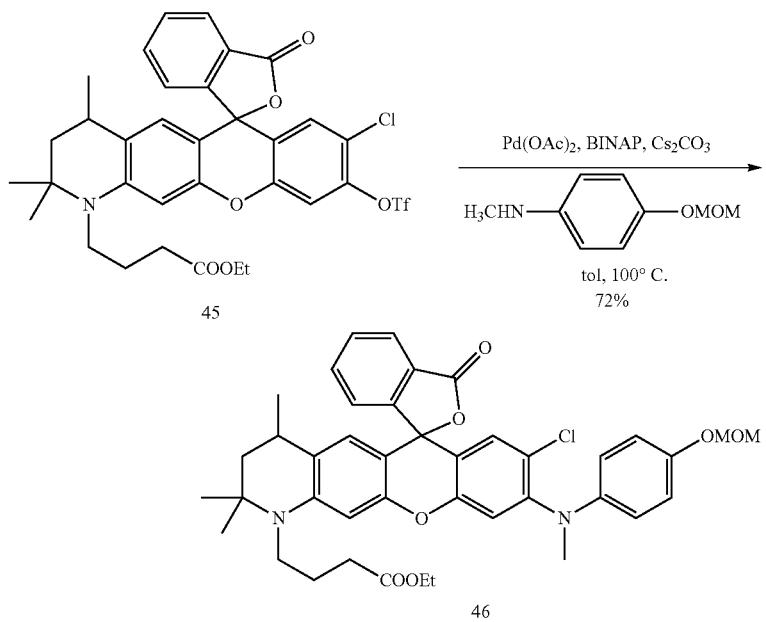

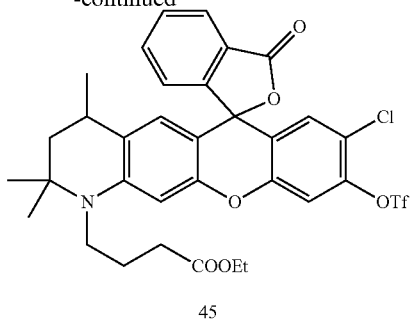

To a solution of 44 in DMF were added Et$_3$N and N-phenyl-bis(trifluoromethanesulfonimide) under argon at room temperature. The mixture was stirred overnight and then diluted with ethyl acetate. The organic solution was washed with HCl solution, water, and dried over anhydrous sodium sulfate, and then concentrated in vacuo. The residue was purified by silica gel column chromatography to give the product 45 (95% yield). $^1$H NMR (400 MHz, CDCl$_3$) δ 8.06 (d, J=7.2 Hz, 1H), 7.77-7.63 (m, 2H), 7.33 (s, 0.5×1H), 7.32 (s, 0.5×1H), 7.23 (d, J=7.2 Hz, 0.5×1H), 7.21 (d, J=7.2

An oven-dried Schlenk tube was charged with Pd(OAc)$_2$, BINAP and Cs$_2$CO$_3$, and flushed with Ar gas for 5 min. A solution of 45 and 4-(methoxymethoxy)-N-methylaniline in toluene was added, and the resulting mixture was first stirred under Ar at room temperature for 30 min and then at 100° C. for 20 h. The reaction mixture was allowed to cool to room temperature, diluted with CH$_2$Cl$_2$ and filtered through a pad of Celite. The filter cake was washed with CH$_2$Cl$_2$. The filtrate was then concentrated and the residue was purified by silica gel column chromatography to give the product 46 (72% yield). $^1$H NMR (400 MHz, CDCl$_3$) δ 8.04 (d, J=7.5 Hz, 1H), 7.72-7.62 (m, 2H), 7.26 (d, J=7.5 Hz, 1H), 7.11 (s, 1H), 6.94 (d, J=7.7 Hz, 2H), 6.76 (s, 1H), 6.73 (d, J=7.7 Hz, 2H), 6.38 (s, 2H), 5.11 (s, 2H), 4.19 (q, J=6.9 Hz, 2H), 3.47 (s, 3H), 3.45-3.35 (m, 1H), 3.24 (s, 3H), 3.20-3.10 (m, 1H), 2.78-2.58 (m, 1H), 2.40 (t, J=6.5 Hz, 2H), 2.05-1.80 (m, 2H), 1.67 (d, J=12.7 Hz, 1H), 1.45 (dd, J=25.7, 12.7 Hz, 1H), 1.34-1.25 (m, 6H), 1.16 (s, 3H), 1.05 (d, J=6.1 Hz, 1.5×3H), 0.95 (d, J=6.1 Hz, 1.5×3H); $^{13}$C NMR (101 MHz, CDCl$_3$) δ 173.14, 173.11, 169.37, 152.47, 152.31, 151.33, 151.28, 151.22, 151.06, 150.97, 148.22, 148.16, 147.22, 147.00, 143.75, 134.98, 134.92, 129.79, 129.74, 129.66, 127.19, 127.02, 125.76, 125.37, 125.27, 125.05, 124.74, 124.11, 124.00, 118.27, 118.23, 117.24, 116.93, 116.84, 115.05, 115.02, 104.29, 97.76, 97.71, 95.13, 83.93, 83.76, 60.56, 55.85, 55.02, 54.86, 46.45, 46.36, 44.59, 44.36, 40.54, 40.52, 31.61, 31.59, 29.45, 29.30, 26.82, 26.64, 25.66, 25.14, 23.51, 23.32, 19.68, 19.48, 14.26.

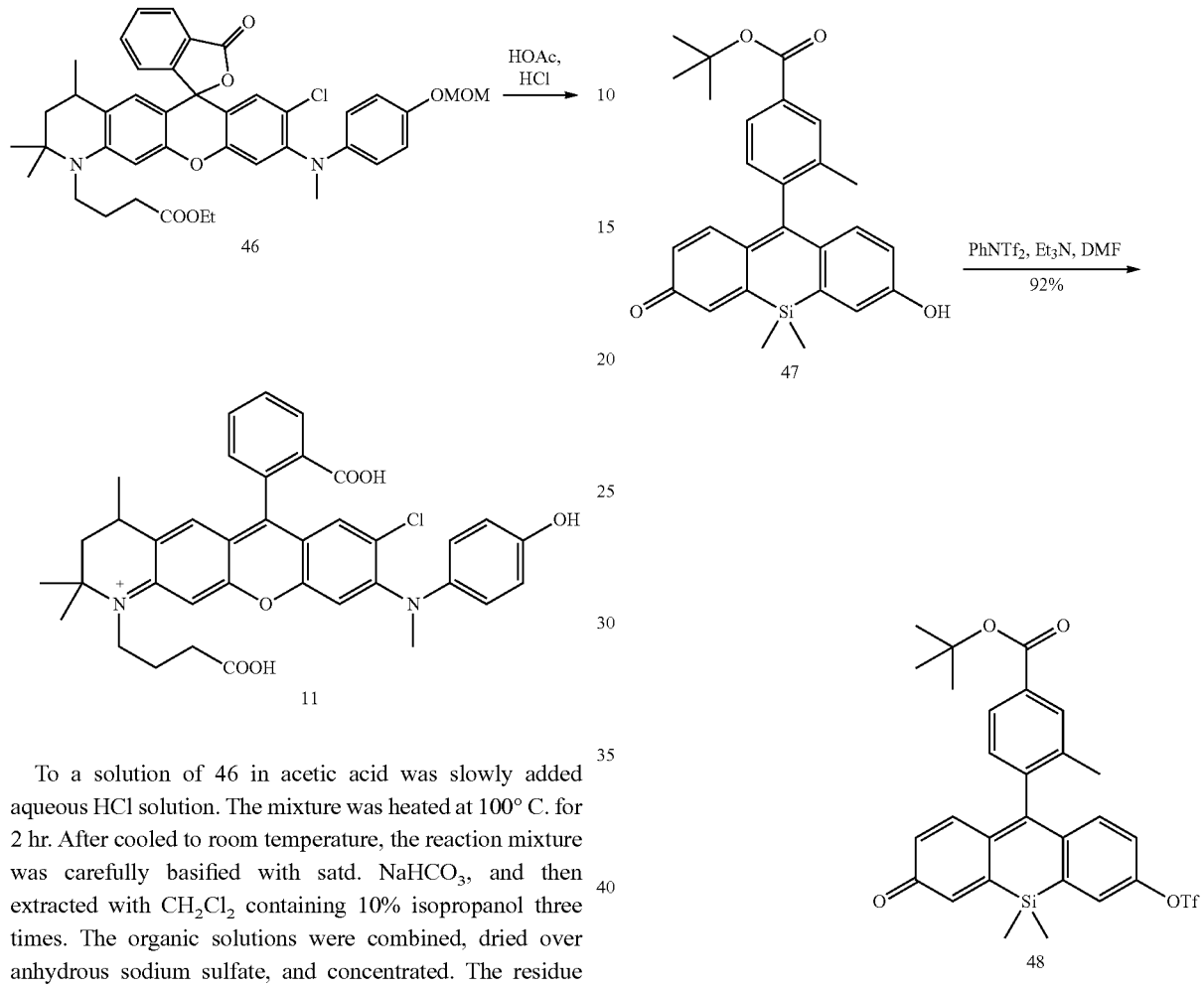

To a solution of 46 in acetic acid was slowly added aqueous HCl solution. The mixture was heated at 100° C. for 2 hr. After cooled to room temperature, the reaction mixture was carefully basified with satd. NaHCO$_3$, and then extracted with CH$_2$Cl$_2$ containing 10% isopropanol three times. The organic solutions were combined, dried over anhydrous sodium sulfate, and concentrated. The residue was purified with silica gel column chromatography to give the product 11. $^1$H NMR (400 MHz, CD$_3$OD) δ 8.38-8.33 (m, 1H), 7.89 (t, J=7.4 Hz, 1H), 7.83 (t, J=7.4 Hz, 1H), 7.49 (s, 0.5×1H), 7.48 (s, 0.5×1H), 7.45 (d, J=7.4 Hz, 1H), 7.31 (s, 1H), 7.10 (s, 0.5×1H), 7.06 (s, 0.5×1H), 7.02-6.92 (m, 3H), 6.76 (d, J=8.7 Hz, 2H), 3.89-3.77 (m, 1H), 3.74-3.62 (m, 1H), 3.53 (s, 0.5×3H), 3.52 (s, 0.5×3H), 2.97-2.85 (m, 1H), 2.60-2.56 (m, 2H), 2.10-2.00 (m, 2H), 1.96 (dd, J=13.6, 4.0 Hz, 1H), 1.61 (td, J=13.6, 5.0 Hz, 1H), 1.54 (s, 3H), 1.43 (s, 0.5×3H), 1.42 (s, 0.5×3H), 1.13 (d, J=3.4 Hz, 0.5×3H), 1.12 (d, J=3.4 Hz, 0.5×3H); $^{13}$C NMR (101 MHz, CD$_3$OD) δ 176.56, 168.26, 168.21, 159.26, 159.17, 157.60, 157.57, 156.92, 156.89, 156.07, 155.93, 155.37, 155.33, 141.29, 135.10, 134.91, 134.78, 134.76, 134.13, 134.10, 132.51, 132.41, 132.23, 131.88, 131.71, 131.56, 131.33, 126.85, 126.82, 126.73, 125.88, 117.56, 117.49, 117.14, 117.05, 117.00, 107.62, 107.60, 98.46, 98.41, 60.51, 60.48, 47.26, 45.27, 45.25, 44.68, 44.67, 31.33, 29.19, 29.16, 28.03, 25.98, 23.94, 19.07, 18.97.

Example 3

Synthesis of Red Fluorogenic Compound 22

To a solution of 47 in DMF were added Et$_3$N and N-phenyl-bis(trifluoromethanesulfonimide) under Ar at room temperature. The mixture was stirred overnight and then diluted with ethyl acetate. The organic solution was washed with HCl solution, water, and dried over anhydrous sodium sulfate, and then concentrated in vacuo. The residue was purified by silica gel column chromatography to give the product 48 (92% yield). $^1$H NMR (400 MHz, CDCl$_3$) δ 7.96 (s, 1H), 7.92 (d, J=7.9 Hz, 1H), 7.50 (d, J=2.8 Hz, 1H), 7.17 (d, J=7.9 Hz, 1H), 7.08 (dd, J=9.0, 2.8 Hz, 1H), 6.90-6.87 (m, 2H), 6.84 (d, J=2.1 Hz, 1H), 6.21 (dd, J=10.2, 2.1 Hz, 1H), 2.09 (s, 3H), 1.59 (s, 9H), 0.52 (s, 3H), 0.50 (s, 3H); $^{13}$C NMR (101 MHz, CDCl$_3$) δ 184.13, 165.18, 151.50, 149.68, 145.80, 142.75, 141.29, 140.70, 140.30, 138.15, 136.47, 134.31, 132.49, 131.45, 130.89, 129.45, 129.33, 129.03, 127.25, 126.59, 123.02, 122.76, 118.67 (q, J$_{C-F}$=322.1 Hz), 81.45, 28.14, 19.50, −1.48, −1.74; $^{19}$F NMR (376 MHz, CDCl$_3$) δ −72.82.

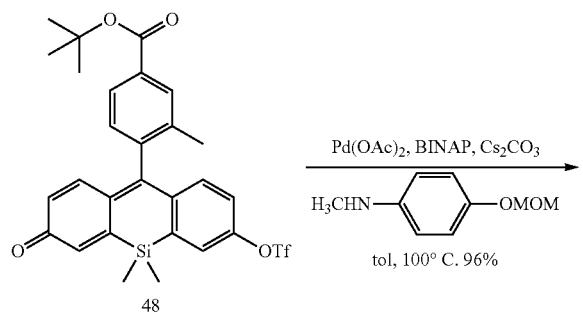

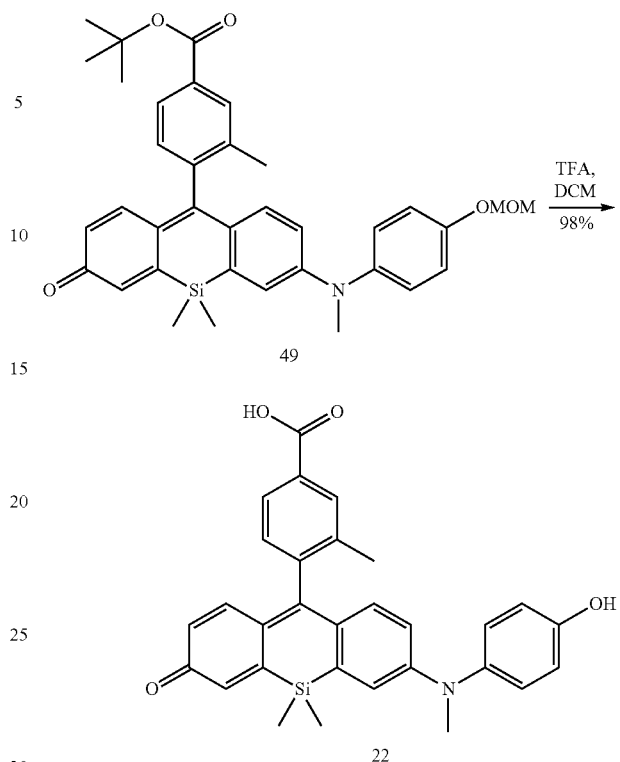

An oven-dried Schlenk tube was charged with Pd(OAc)$_2$, BINAP and Cs$_2$CO$_3$, and flushed with Ar gas for 5 min. A solution of 48 and 4-(methoxymethoxy)-N-methylaniline in toluene was added, and the resulting mixture was first stirred under Ar at room temperature for 30 min and then at 100° C. for 20 h. The reaction mixture was allowed to cool to room temperature, diluted with CH$_2$Cl$_2$ and filtered through a pad of Celite. The filter cake was washed with CH$_2$Cl$_2$. The filtrate was then concentrated and the residue was purified by silica gel column chromatography to give the product 49 (96% yield). $^1$H NMR (400 MHz, CDCl$_3$) δ 7.94 (s, 1H), 7.91 (d, J=7.9 Hz, 1H), 7.17 (d, J=7.8 Hz, 1H), 7.13 (d, J=8.9 Hz, 2H), 7.08 (d, J=8.9 Hz, 2H), 6.99 (d, J=2.7 Hz, 1H), 6.85 (d, J=2.0 Hz, 1H), 6.84 (d, J=10.0 Hz, 1H), 6.63 (d, J=9.2 Hz, 1H), 6.44 (dd, J=9.2, 2.7 Hz, 1H), 6.22 (dd, J=10.0, 2.0 Hz, 1H), 5.19 (s, 2H), 3.50 (s, 3H), 3.37 (s, 3H), 2.13 (s, 3H), 1.63 (s, 9H), 0.45 (s, 3H), 0.44 (s, 3H); $^{13}$C NMR (101 MHz, CDCl$_3$) δ 184.20, 165.54, 156.25, 155.65, 150.09, 146.82, 144.26, 141.14, 140.68, 140.30, 136.51, 136.23, 134.97, 131.79, 130.99, 129.43, 128.80, 127.90, 127.02, 126.76, 126.66, 119.14, 117.62, 114.32, 94.61, 81.29, 56.16, 40.35, 28.26, 19.48, −0.97, −1.21.

To a solution of 49 in CH$_2$Cl$_2$ was added TFA slowly at room temperature. The mixture was stirred for 2 hr and then concentrated in vacuo. The residue was purified by silica gel column chromatography to give the product 22 in 98% yield. $^1$H NMR (400 MHz, CD$_3$OD) δ 8.07 (s, 1H), 8.03 (d, J=7.9 Hz, 1H), 7.36 (d, J=2.2 Hz, 1H), 7.30-7.27 (m, 2H), 7.22 (d, J=8.8 Hz, 2H), 7.16 (d, J=9.9 Hz, 1H), 7.05 (d, J=9.1 Hz, 1H), 6.96 (d, J=8.8 Hz, 2H), 6.78 (dd, J=9.9, 2.2 Hz, 1H), 6.75 (dd, J=9.1, 2.6 Hz, 1H), 3.74 (s, 3H), 2.11 (s, 3H), 0.53 (s, 3H), 0.51 (s, 3H); $^{13}$C NMR (101 MHz, CD$_3$OD) δ 170.30, 169.09, 167.89, 159.75, 157.82, 152.92, 147.96, 144.45, 144.35, 141.90, 137.61, 136.37, 132.87, 132.59, 131.45, 130.50, 130.08, 128.26, 128.14, 126.12, 125.77, 120.01, 118.52, 117.96, 43.17, 19.50, −1.64, −1.89.

Example 4

Synthesis of Far Red Fluorogenic Compounds 25 and 27

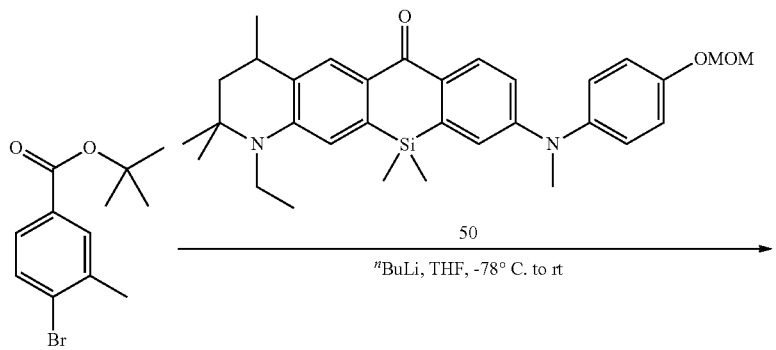

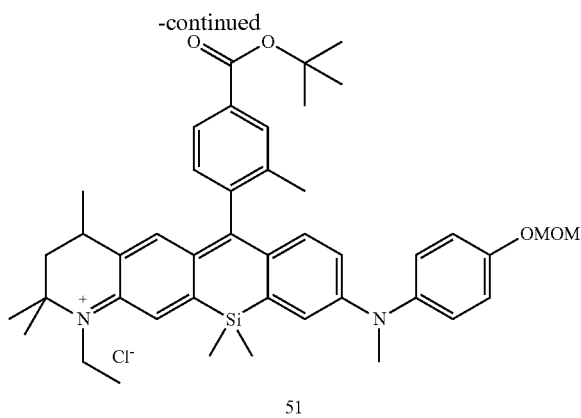

51

To a solution of t-butyl 4-bromo-3-methylbenzoate (585 mg, 2.16 mmol) in dry THF (10 mL) at −78° C., was added n-BuLi (1.46 mL, 2.38 mmol) dropwise under argon atmosphere. Then HMPA (73 μL, 0.431 mmol) was added after 30 min. And a solution of 50 (226 mg, 0.431 mmol) in dry THF (2 mL) was added 5 min later. The resulting mixture was stirred at −78° C. to room temperature for 12 h. The reaction was quenched with 3N HCl for 10 min and extracted with DCM for 3 times. The extracts was dried over anhydrous sodium sulfate, concentrated and purified by silica gel column chromatography to give the product 51 (307 mg, 96% yield). $^1$H NMR (400 MHz, CDCl$_3$) δ 7.84 (s, 1H), 7.81 (d, J=7.8 Hz, 1H), 7.07-7.03 (m, 4H), 7.01-6.99 (m, 3H), 6.75 (s, 1H), 6.72 (d, J=9.5 Hz, 1H), 6.38 (dd, J=9.5, 2.6 Hz, 1H), 5.08 (s, 2H), 3.80-3.72 (m, 2H), 3.52 (s, 3H), 3.37 (s, 3H), 3.31-3.28 (m, 1H), 2.57-2.50 (m, 1H), 1.99 (s, 3H), 1.73 (dd, J=13.6, 4.3 Hz, 1H), 1.51 (s, 9H), 1.48-1.43 (m, 2H), 1.40 (s, 3H), 1.31-1.26 (m, 6H), 1.03-1.01 (m, 3H), 0.83-0.81 (m, 3H), 0.46 (d, J=2.2 Hz, 3H), 0.45 (d, J=2.4 Hz, 3H); $^{13}$C NMR (101 MHz, CDCl$_3$) δ 167.11, 164.99, 156.49, 153.20, 153.16, 151.91, 151.86, 148.19, 148.06, 146.14, 146.34, 142.61, 139.48, 139.39, 138.02, 136.53, 136.43, 135.92, 135.77, 132.17, 132.14, 130.91, 130.70, 130.54, 130.47, 128.91, 128.76, 127.81, 127.78, 127.46, 127.01, 126.90, 126.49, 126.32, 122.31, 121.12, 121.06, 117.61, 115.02, 94.29, 81.39, 59.12, 59.03, 56.00, 44.30, 41.36, 41.16, 29.43, 28.67, 27.98, 26.23, 26.17, 26.11, 26.06, 19.35, 19.28, 18.53, 18.33, 14.81, −0.85, −1.13, −1.43, −1.76.

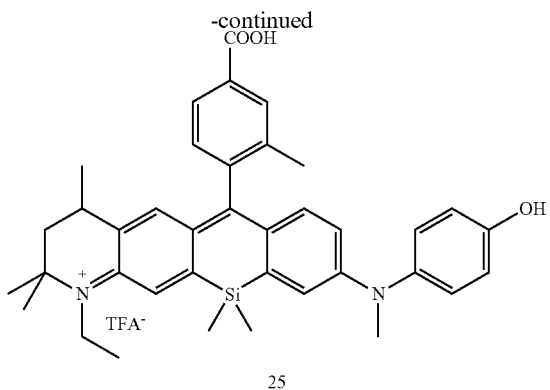

25

To a solution of 51 (306 mg, 2.16 mmol) in DCM at 0° C. was added TFA dropwise. The resulting mixture was stirred at room temperature for 3 h. The reaction mixture was then concentrated and azeotroped with toluene for 3 times, and purified by silica gel column chromatography to give the product 25 (236 mg, 80% yield). $^1$H NMR (400 MHz, CDCl$_3$) δ 8.06 (s, 1H), 7.97 (d, J=7.9 Hz, 1H), 7.30 (s, 1H), 7.21-7.19 (m, 2H), 7.11-7.08 (m, 2H), 6.92-6.87 (m, 4H), 6.58 (dd, J=9.5, 2.4 Hz, 1H), 3.92 (br, 1H), 3.90 (br, 1H), 3.52 (s, 3H), 2.75 (br, 1H), 2.09 (s, 3H), 1.87 (dd, J=13.5, 4.2 Hz, 1H), 1.50 (s, 3H), 1.54-1.48 (m, 1H), 1.40-1.37 (m, 6H), 0.90 (m, 6H), 0.53 (d, J=2.9 Hz, 3H), 0.51 (t, J=3.8 Hz, 3H); $^{13}$C NMR (101 MHz, CDCl$_3$) δ 168.98, 168.13, 168.09, 158.63, 155.21, 155.18, 153.41, 153.35, 149.09, 148.98, 147.65, 147.56, 144.76, 140.81, 140.75, 137.73, 137.55, 137.31, 132.51, 132.45, 132.30, 132.26, 130.59, 130.35, 128.82, 128.75, 128.27, 128.18, 127.95, 123.75, 122.85, 122.80, 117.86, 116.09, 60.52, 60.44, 45.55, 41.78, 41.68, 28.91, 28.86, 27.47, 27.43, 26.25, 19.51, 19.47, 18.83, 18.66, 15.15, −1.13, −1.37, −1.63, −1.89.

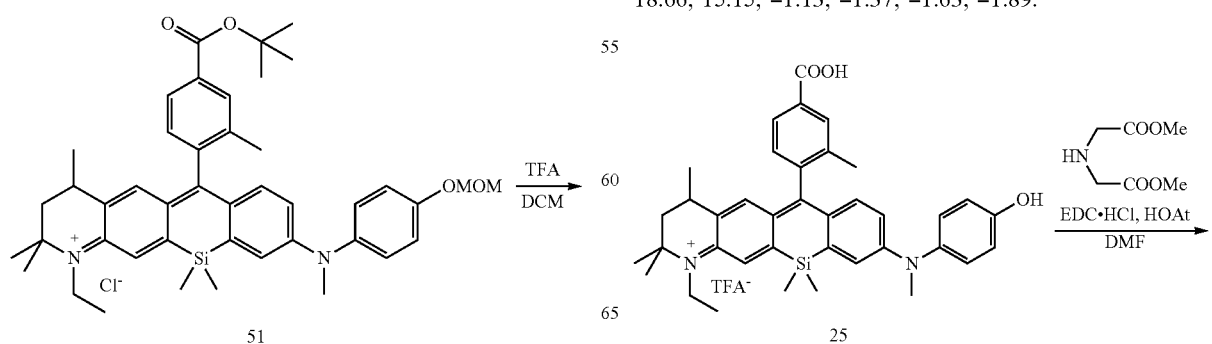

-continued

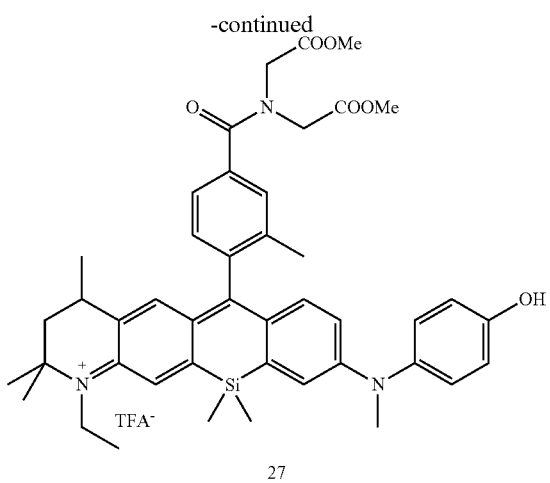

27

Example 5

Synthesis of Mitochondrial-Targeting Fluorogenic Compound 25

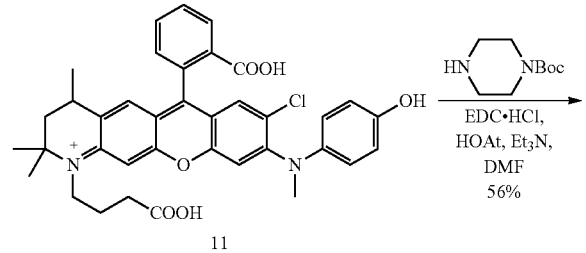

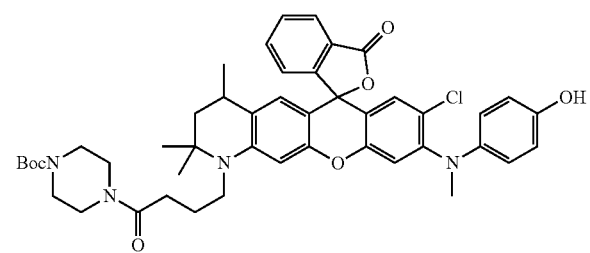

52

To a solution of 25 (116 mg, 0.162 mmol) and dimethyl 3,3'-iminodipropanoate (52 mg, 0.324 mmol) in anhydrous DMF (2 mL) at room temperature was added 1-hydroxy-7-azabenzotriazole (HOAt) (27 mg, 0.194 mmol), and N-(3-dimethylaminopropyl)-N'-ethylcarbodiimide hydrochloride (EDC.HCl) (44 mg, 0.227 mmol) successively under argon atmosphere. The reaction mixture was stirred overnight and then diluted with ethyl acetate. The organic layer was washed with saturated NaHCO$_3$, H$_2$O and brine. The extracts was dried over anhydrous sodium sulfate, concentrated and purified by silica gel column chromatography to give the product 27 (122 mg, 88% yield). $^1$H NMR (400 MHz, CDCl$_3$) δ 10.25 (br, 1H), 7.49 (d, J=10.2 Hz, 1H), 7.42 (dd, J=8.1, 3.9 Hz, 1H), 7.31 (d, J=8.4 Hz, 1H), 7.16 (dd, J=7.2, 5.7 Hz, 1H), 7.07-7.05 (m, 2H), 6.99-6.97 (m, 3H), 6.81 (d, J=6.9 Hz, 1H), 6.61 (d, J=8.4 Hz, 1H), 4.45 (s, 2H), 4.40 (s, 2H), 3.85-3.65 (m, 1H), 3.82 (s, 3H), 3.79 (s, 3H), 3.55 (s, 3H), 3.70-3.50 (m, 1H), 2.10-2.09 (m, 3H), 1.85 (dd, J=13.5, 3.8 Hz, 1H), 1.61-1.58 (m, 1H), 1.56 (s, 3H), 1.43-1.38 (m, 6H), 0.94 (t, J=5.4 Hz, 3H), 0.50 (s, 6H); $^{13}$C NMR (101 MHz, CDCl$_3$) δ 171.57, 169.52, 169.32, 166.83, 158.61, 154.05, 154.02, 151.45, 151.41, 147.59, 147.46, 146.59, 140.82, 140.54, 136.74, 136.22, 136.17, 135.14, 135.12, 134.66, 130.33, 130.22, 129.27, 128.88, 128.57, 127.64, 127.58, 127.10, 126.98, 126.62, 124.15, 123.74, 122.41, 121.58, 117.85, 114.84, 58.84, 58.78, 52.69, 52.36, 51.68, 47.56, 44.55, 41.65, 40.84, 28.88, 26.36, 26.31, 26.25, 19.51, 19.40, 18.56, 18.35, 14.84, −0.81, −1.04, −1.39, −1.65.

To a solution of 11 in DMF were added triethylamine, 1-hydroxy-7-azabenzotriazole (HOAt), N-(3-dimethylaminopropyl)-N'-ethylcarbodiimide hydrochloride (EDC.HCl), and N-methylpiperazine successively under Ar. The reaction mixture was stirred overnight and then diluted with ethyl acetate. The organic layer was washed with saturated NaHCO$_3$ solution followed by 0.1 N HCl and brine. The extracts was dried over anhydrous sodium sulfate, concentrated and purified by silica gel column chromatography to give the product 52 (56% yield). $^1$H NMR (500 MHz, CDCl$_3$) δ 8.04 (d, J=7.6 Hz, 1H), 7.71 (t, J=7.4 Hz, 1H), 7.64 (t, J=7.4 Hz, 1H), 7.24 (d, J=7.6 Hz, 1H), 7.02 (s, 1H), 6.81-6.72 (m, 5H), 6.38 (s, 2H), 3.67-3.62 (m, 3H), 3.46-3.42 (m, 7H), 3.23 (s, 3H), 2.71-2.62 (m, 1H), 2.42 (s, 2H), 2.17-2.04 (m, 3H), 1.68-1.64 (m, 10H), 1.31 (s, 3H), 1.25 (s, 3H), 1.05 (d, J=6.6 Hz, 0.5×3H), 0.95 (d, J=6.6 Hz, 0.5×3H).

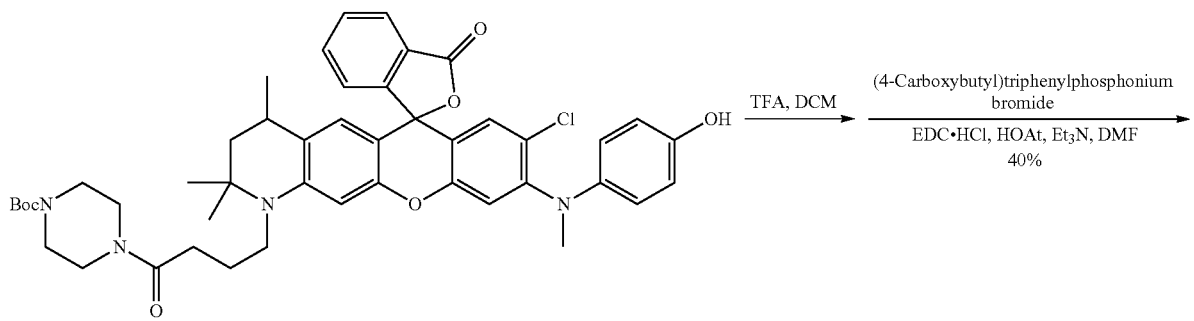

52

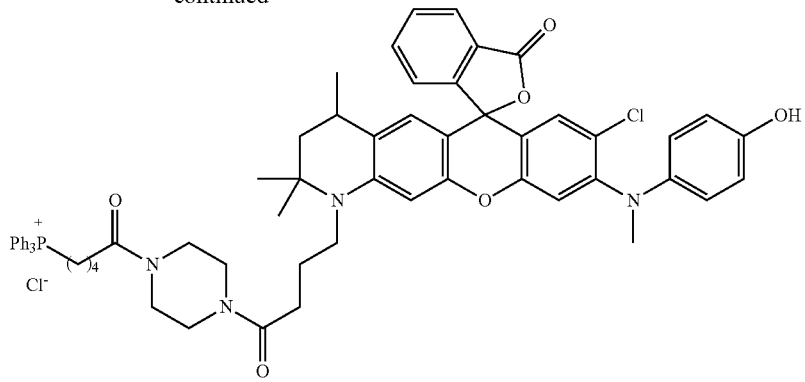

32

To a solution of 52 in CH$_2$Cl$_2$ was added TFA slowly at room temperature. The mixture was stirred for 2 hr and then concentrated in vacuo. The residue was redissolved in anhydrous DMF. To this solution were added triethylamine, 1-hydroxy-7-azabenzotriazole (HOAt), N-(3-dimethylaminopropyl)-N'-ethylcarbodiimide hydrochloride (EDC.HCl), and (4-Carboxybutyl)triphenylphosphonium bromide successively under Ar. The reaction mixture was stirred overnight and then diluted with ethyl acetate. The organic layer was washed with saturated NaHCO$_3$ solution followed by 0.1 N HCl and brine. The extracts was dried over anhydrous sodium sulfate, concentrated and purified by silica gel column chromatography to give the product 32 (40% yield). $^1$H NMR (500 MHz, CD$_3$OD) δ 8.32 (d, J=7.3 Hz, 1H), 7.90-7.86 (m, 5H), 7.82-7.75 (m, 12H), 7.49-7.48 (m, 1H), 7.44-7.41 (m, 2H), 7.07-7.02 (m, 1H), 6.96-6.93 (m, 3H), 6.75 (d, J=8.6 Hz, 2H), 3.68-3.67 (m, 1H), 3.63-3.56 (m, 9H), 3.50-3.43 (m, 5H), 2.89-2.88 (m, 1H), 2.67 (t, J=6.7 Hz, 2H), 2.51 (t, J=6.7 Hz, 2H), 2.11-2.02 (m, 2H), 1.85 (dd, J=14.5, 5.3 Hz, 1H), 1.76-1.73 (m, 2H), 1.63-1.60 (m, 2H), 1.58-1.56 (m, 1H), 1.54 (s, 3H), 1.42-1.41 (m, 3H), 1.27-1.10 (m, 3H).

Example 6

Sensitive and Specific Detection of Peroxynitrite with Green Fluorogenic Compound 2

This Example shows that green fluorogenic Compound 2 sensitively and selectively detects peroxynitrite. Specifically, Compound 2 is dissolved in 0.1 M phosphate buffer at pH 7.4 to form a 1 µM solution, with excitation and emission spectra at 510 nm and 530 nm, respectively. The 1 µM solution of Compound 2 is treated with peroxynitrite at various concentrations. FIG. 1A shows that the florescence intensity of Compound 2 increases with increasing concentration of peroxynitrite.

Figure 1B:
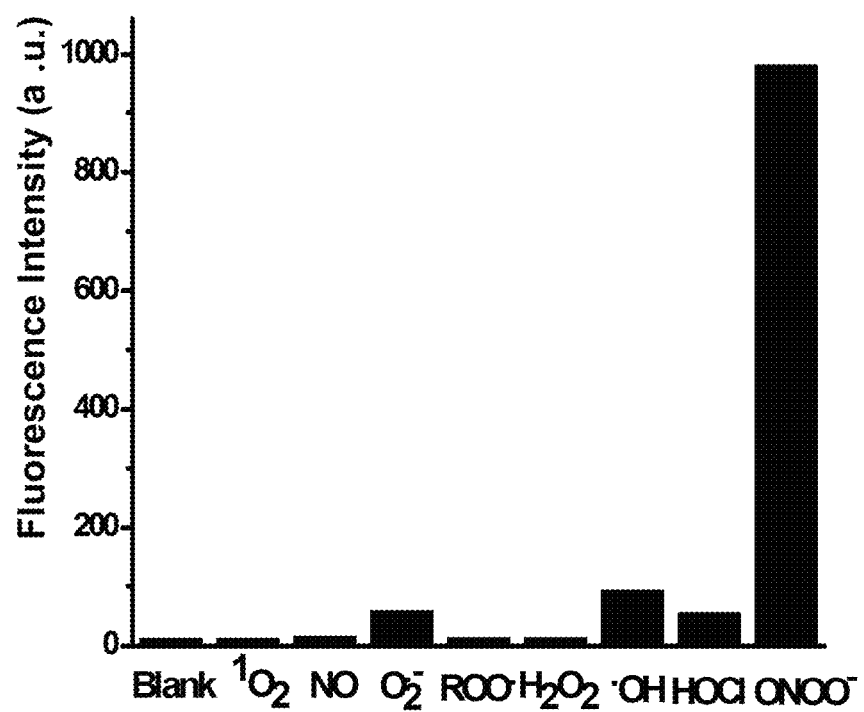
FIG. 1B shows increases in fluorescence intensity of Compound 2 after treatment with different reactive oxygen species (ROS) and reactive nitrogen species (RNS). The spectra were acquired by dissolving Compound 2 in 0.1 M phosphate buffer at pH 7.4 to form a 1 μM solution, with excitation and emission spectra at 510 nm and 530 nm, respectively. The concentration of highly reactive oxygen species hydroxyl radical (.OH), hypochlorous acid ($^-OCl$), and peroxynitrite ($ONOO^-$) is 1 μM. The concentration of $^1O_2$, $O_2.^-$, NO, ROO. and $H_2O_2$ is 10 μM.

The reactivity of Compound 2 is compared toward different reactive oxygen species (ROS) and reactive nitrogen species (RNS). Specifically, the 1 µM solution of compound 2 is treated with various ROS and RNS. The concentration of highly reactive oxygen species (hydroxyl radical (.OH), hypochlorous acid ($^-$OCl), and peroxynitrite (ONOO$^-$)) is 1 µM. The concentration of $^1$O$_2$, O$_2$.$^-$, NO, ROO. and H$_2$O$_2$ is 10 µM. FIG. 1B shows that treatment with peroxynitrite results in a much higher increase in fluorescence intensity of Compound 2 than treatment with other ROS and RNS.

Example 7

Sensitive and Specific Detection of Peroxynitrite with Yellow Fluorogenic Compound 11

Figure 2A:
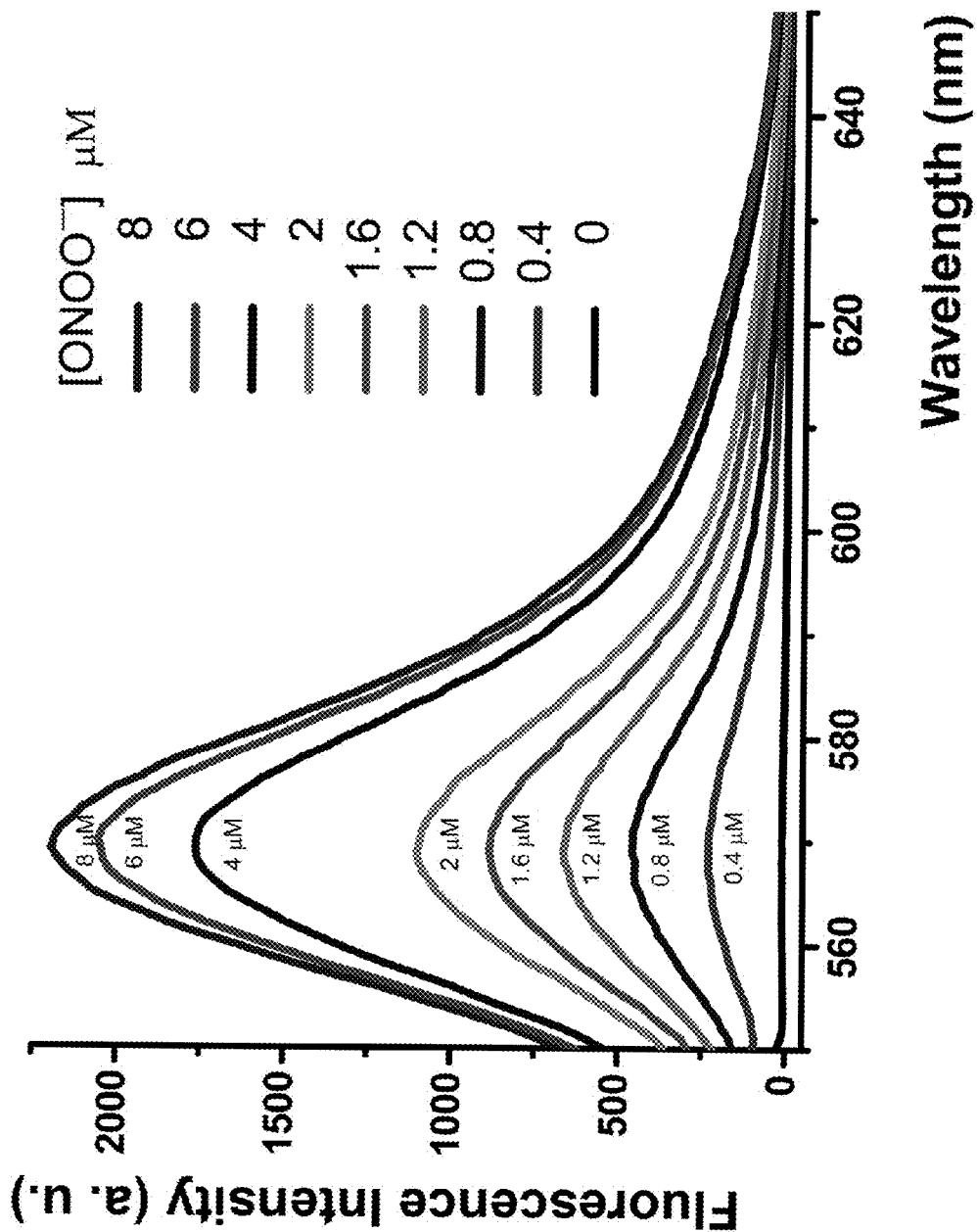
FIG. 2A depicts fluorescence spectra showing fluorescence intensities of Compound 11 after treatment with different amounts of peroxynitrite.

This Example shows that yellow fluorogenic Compound 11 sensitively and selectively detects peroxynitrite. Specifically, Compound 11 is dissolved in 0.1 M phosphate buffer at pH 7.4 to form a 2 µM solution, with excitation and emission spectra at 547 nm and 570 nm, respectively. The 2 µM solution of Compound 11 is treated with peroxynitrite at various concentrations. FIG. 2A shows that the florescence intensity of Compound 11 increases with increasing concentration of peroxynitrite.

Figure 2B:
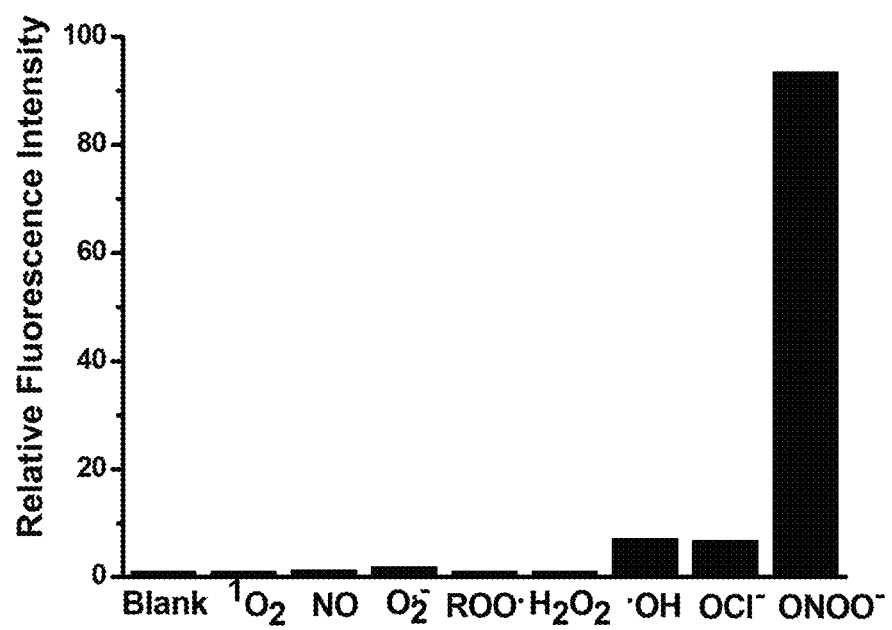
FIG. 2B shows increases in fluorescence intensity of Compound 11 after treatment with different ROS and RNS. The spectra were acquired by dissolving Compound 7 in 0.1M phosphate buffer at pH 7.4 to form a 2 μM solution, with excitation and emission at 547 nm and 570 nm, respectively. The concentration of highly reactive oxygen species hydroxyl radical (.OH), hypochlorous acid ($^-OCl$), and peroxynitrite ($ONOO^-$) is 2 μM. The concentration of $^1O_2$, $O_2.^-$, NO, ROO. and $H_2O_2$ is 20 μM.

The reactivity of Compound 11 is compared with different reactive oxygen species (ROS) and reactive nitrogen species (RNS). Specifically, the 2 µM solution of compound 11 is treated with various ROS and RNS. The concentration of highly reactive oxygen species (hydroxyl radical (.OH), hypochlorous acid ($^-$OCl), and peroxynitrite (ONOO$^-$)) is 2 µM. The concentration of $^1$O$_2$, O$_2$.$^-$, NO, ROO. and H$_2$O$_2$ is 20 µM. FIG. 2B shows that treatment with peroxynitrite results in a much higher increase in fluorescence intensity of Compound 11 than treatment with other ROS and RNS.

Example 8

Sensitive and Specific Detection of Peroxynitrite with Red Fluorogenic Compound 22

Figure 3A:
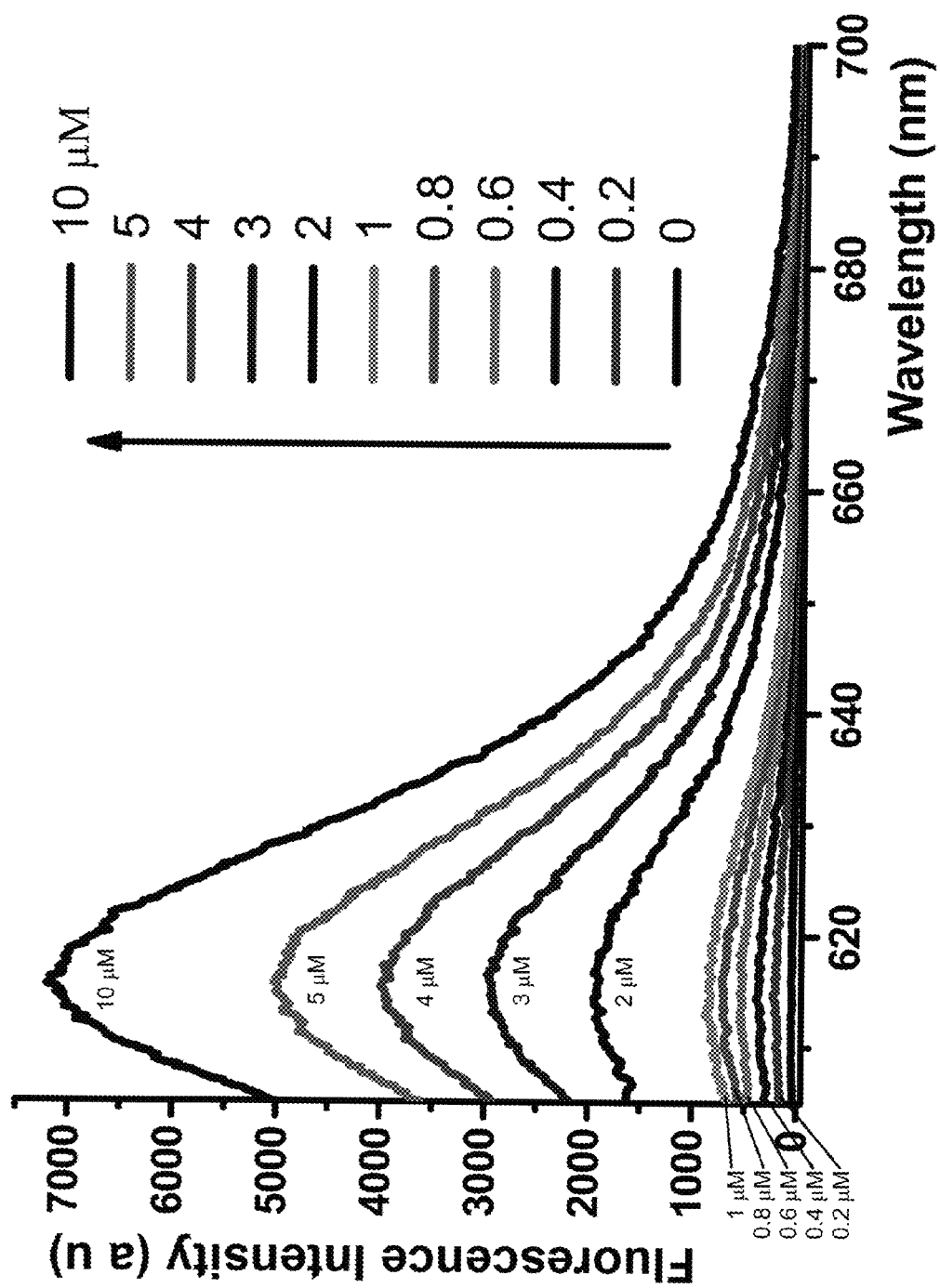
FIG. 3A depicts fluorescence spectra showing fluorescence intensities of Compound 22 after treatment with different amounts of peroxynitrite.

This Example shows that red fluorogenic Compound 22 sensitively and selectively detects peroxynitrite. Specifically, Compound 22 is dissolved in 0.1 M phosphate buffer at pH 7.4 to form a 5 µM solution, with excitation and emission spectra at 600 nm and 617 nm, respectively. The 5 µM solution of Compound 22 is treated with peroxynitrite at various concentrations. FIG. 3A shows that the florescence intensity of Compound 22 increases with increasing concentration of peroxynitrite.

Figure 3B:
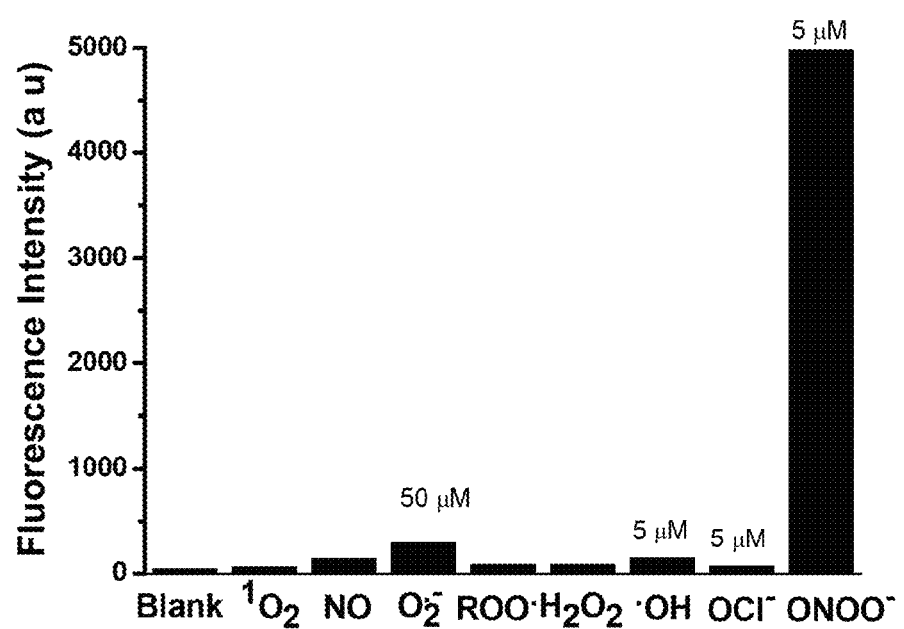
FIG. 3B shows increases in fluorescence intensity of Compound 22 after treatment with different ROS and RNS. The spectra were acquired by dissolving Compound 22 in 0.1M phosphate buffer at pH 7.4 to form a 5 μM solution, with excitation at 600 nm and emission at 617 nm, respectively. The concentration of highly reactive oxygen species hydroxyl radical (.OH), hypochlorous acid ($^-OCl$), and peroxynitrite ($ONOO^-$) is 5 μM. The concentration of $^1O_2$, $O_2.^-$, NO, ROO. and $H_2O_2$ is 50 μM.

The reactivity of Compound 22 is compared with different reactive oxygen species (ROS) and reactive nitrogen species (RNS). Specifically, the 5 µM solution of compound 22 is treated with various ROS and RNS. The concentration of highly reactive oxygen species (hydroxyl radical (.OH), hypochlorous acid ($^-$OCl), and peroxynitrite (ONOO$^-$)) is 5 µM. The concentration of $^1$O$_2$, O$_2$.$^-$, NO, ROO. and H$_2$O$_2$ is 50 µM. FIG. 3B shows that treatment with peroxynitrite results in a much higher increase in fluorescence intensity of Compound 22 than treatment with other ROS and RNS.

Example 9

Sensitive and Specific Detection of Peroxynitrite with Deep Red Fluorogenic Compound 25

Figure 4A:
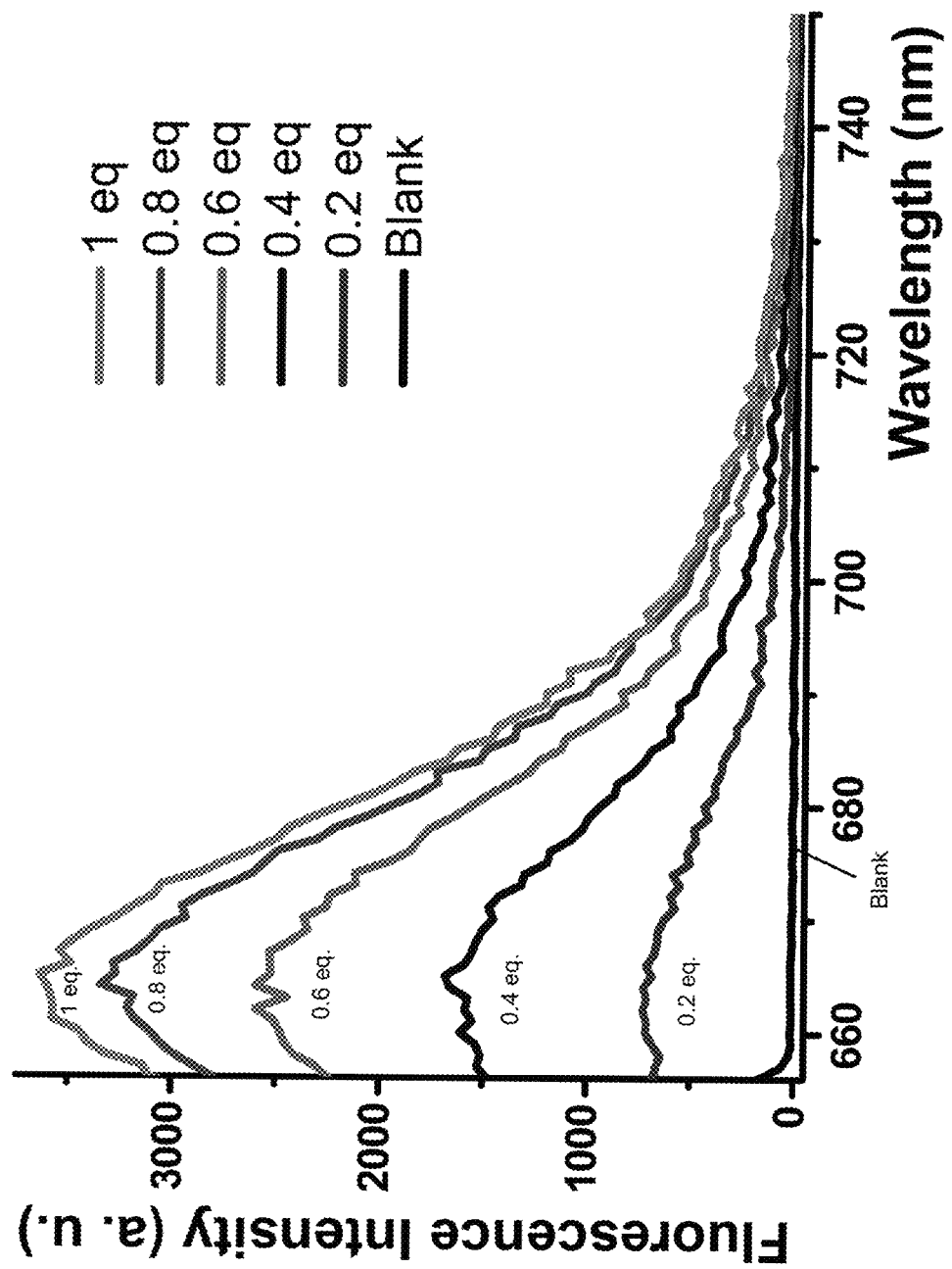
FIG. 4A depicts fluorescence spectra showing fluorescence intensities of Compound 25 after treatment with different amounts of peroxynitrite.

This Example shows that deep red fluorogenic Compound 25 sensitively and selectively detects peroxynitrite. Specifically, Compound 25 is dissolved in 0.1 M phosphate buffer at pH 7.4 to form a 5 µM solution, with excitation and emission spectra at 650 nm and 665 nm, respectively. The 5 µM solution of Compound 25 is treated with peroxynitrite at various concentrations. FIG. 4A shows that the florescence intensity of Compound 25 increases with increasing concentration of peroxynitrite.

Figure 4B:
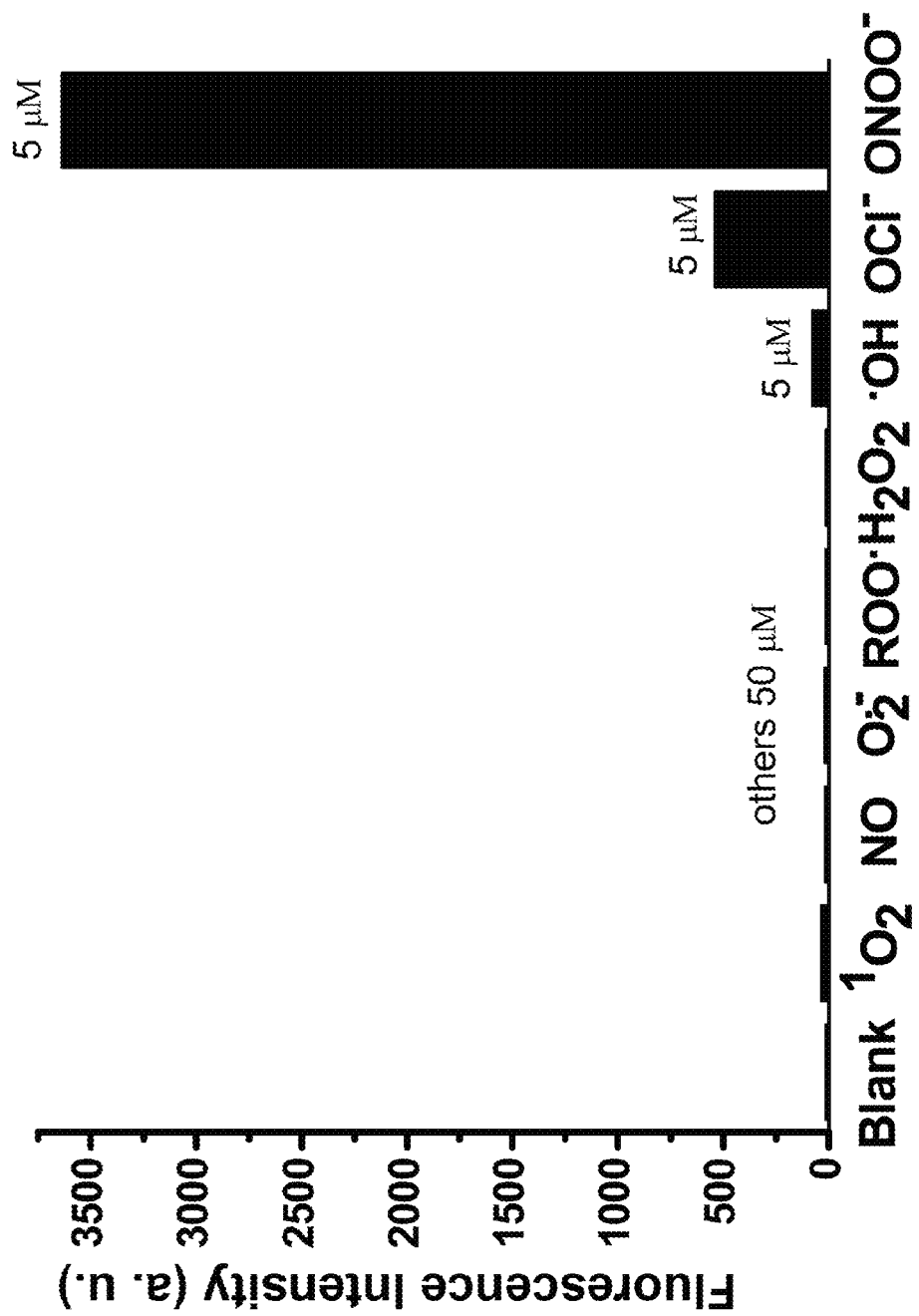
FIG. 4B shows increases in fluorescence intensity of Compound 25 after treatment with different ROS and RNS. The spectra were acquired by dissolving Compound 25 in 0.1M phosphate buffer at pH 7.4 to form a 5 μM solution, with excitation at 650 nm and emission at 665 nm, respectively. The concentration of highly reactive oxygen species hydroxyl radical (.OH), hypochlorous acid ($^-OCl$), and peroxynitrite ($ONOO^-$) is 5 μM. The concentration of $^1O_2$, $O_2.^-$, NO, ROO. and $H_2O_2$ is 50 μM.

The reactivity of Compound 25 is compared with different reactive oxygen species (ROS) and reactive nitrogen species (RNS). Specifically, the 5 µM solution of compound 25 is treated with various ROS and RNS. The concentration of highly reactive oxygen species (hydroxyl radical (.OH), hypochlorous acid (‾OCl), and peroxynitrite (ONOO‾)) is 5 µM. The concentration of $^1O_2$, $O_2.^-$, NO, ROO. and $H_2O_2$ is 50 µM. FIG. 4B shows that treatment with peroxynitrite results in a much higher increase in fluorescence intensity of Compound 25 than treatment with other ROS and RNS.

Example 10

Sensitive and Specific Detection of Peroxynitrite with Mitochondrial-Targeting Fluorogenic Compound 30

Figure 5A:
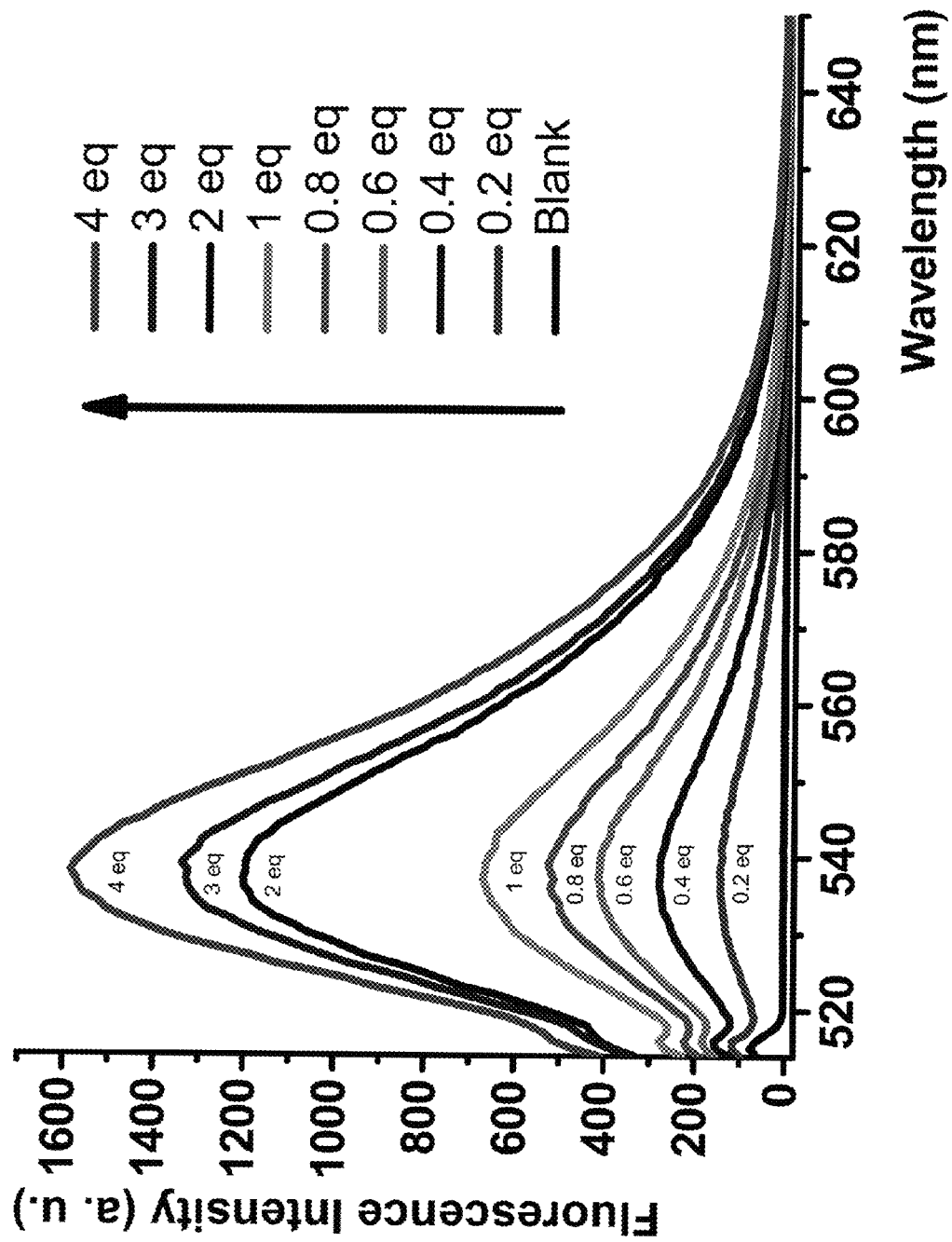
FIG. 5A depicts fluorescence spectra showing fluorescence intensities of Compound 30 after treatment with different amounts of peroxynitrite.

This Example shows that mitochondrial-targeting fluorogenic Compound 30 sensitively and selectively detects peroxynitrite. Specifically, Compound 30 is dissolved in 0.1 M phosphate buffer at pH 7.4 to form a 1 µM solution and excited at 515 nm. The 1 µM solution of Compound 30 is treated with peroxynitrite at various concentrations. FIG. 5A shows that the florescence intensity of Compound 30 increases with increasing concentration of peroxynitrite.

Figure 5B:
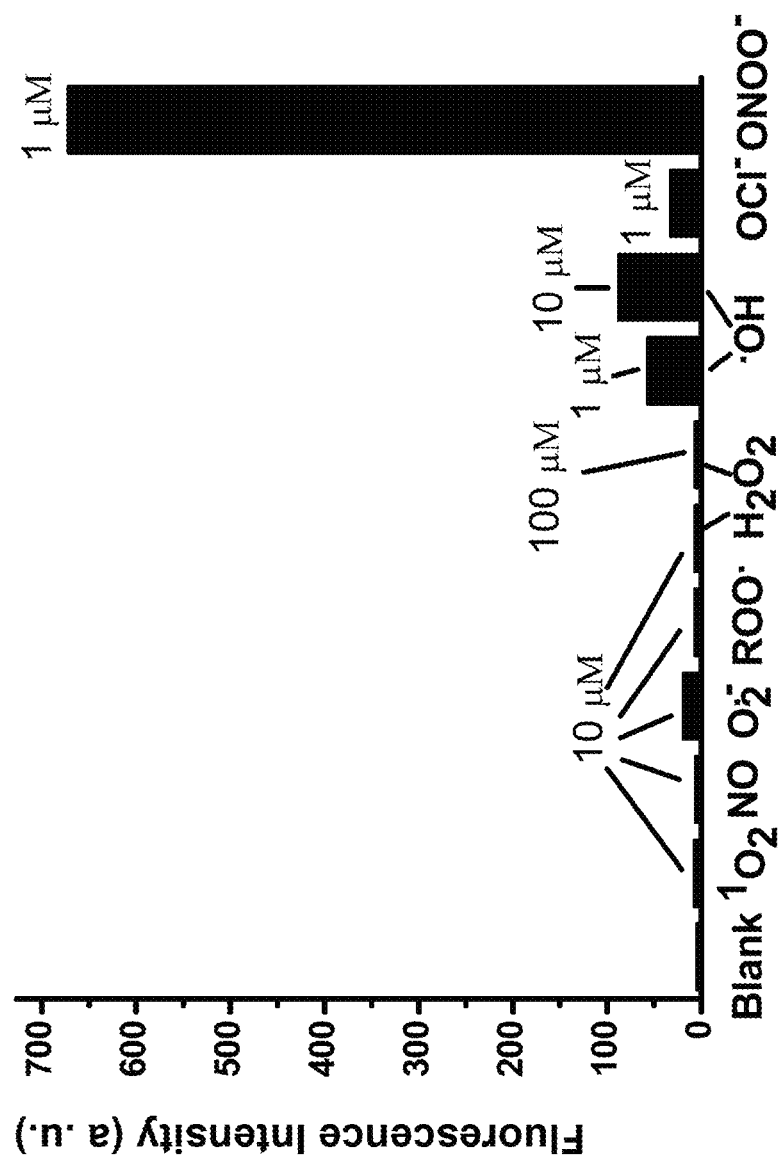
FIG. 5B shows increases in fluorescence intensity of Compound 30 at the emission maximum of 540 nm after treatment with different ROS and RNS. The spectra were acquired by dissolving Compound 30 in 0.1 M phosphate buffer at pH 7.4 and exciting at 515 nm. The concentration of highly reactive oxygen species hypochlorous acid ($^-OCl$) and peroxynitrite ($ONOO^-$) is 1 µM. The concentration of hydroxyl radical (.OH) is 1 µM or 10 µM. The concentration of $^1O_2$, $O_2.^-$, NO, ROO. and $H_2O_2$ is 10 µM or 100 µM. (see figure for exact concentrations of certain ROS and RNS)
Figure 6:
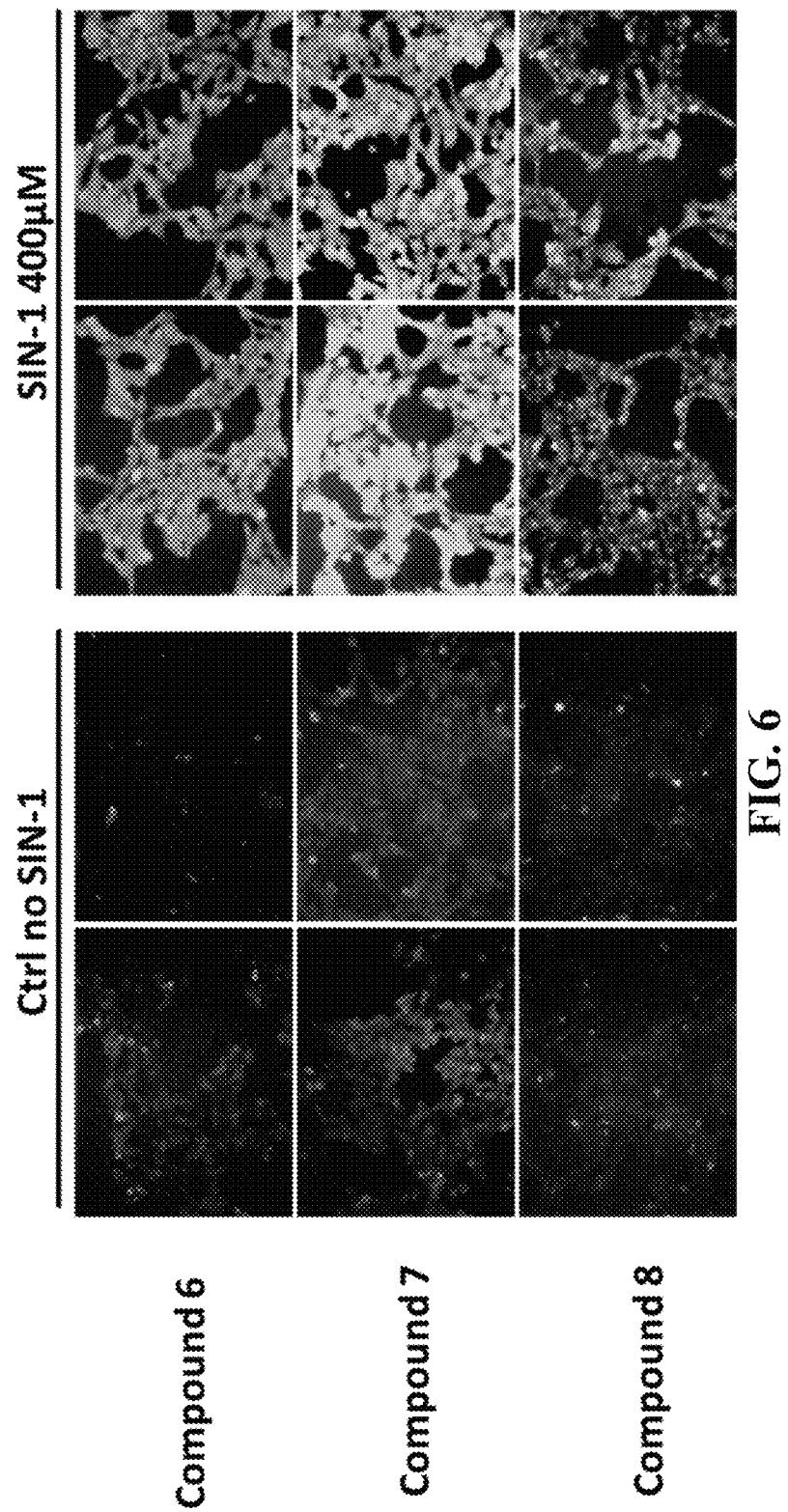
FIG. 6 shows fluorescent microscopy results of SH-SY5Y cells upon treatment with or without SIN-1, a peroxynitrite generator, using Compounds 6, 7, and 8. SH-SY5Y cells were co-stained with different compounds with or without SIN-1 for 1 h, and then washed quickly with PBS for 3 times and maintained in non-phenol red medium. Left: no SIN-1 treatment; Right: with SIN-1 treatment.
Figure 7:
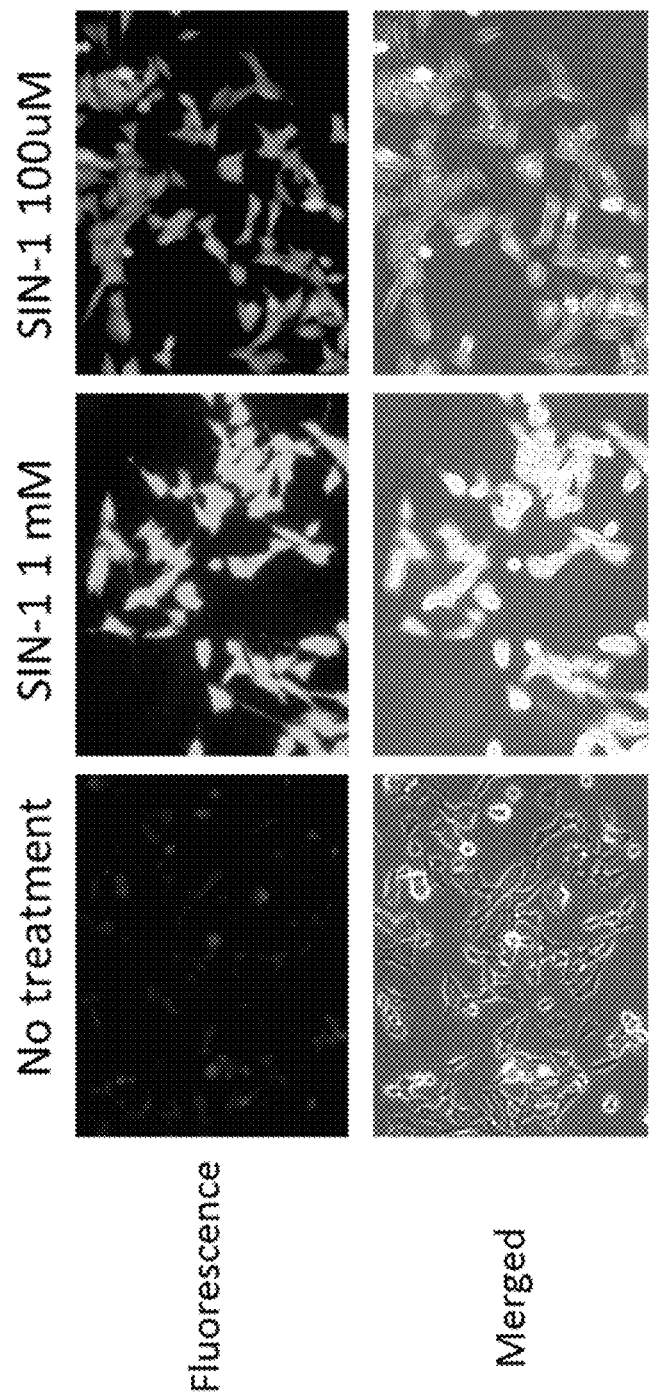
FIG. 7 shows fluorescent microscopy results of SH-SY5Y cells upon treatment with or without SIN-1, a peroxynitrite generator, using Compounds 14. SH-SY5Y cells were co-stained with different compounds with or without SIN-1 for 1 h, and then washed quickly with PBS for 3 times and maintained in non-phenol red medium. Left: no SIN-1 treatment; Middle: with 1 mM SIN-1 treatment; Right: with 100 µM SIN-1 treatment.
Figure 8:
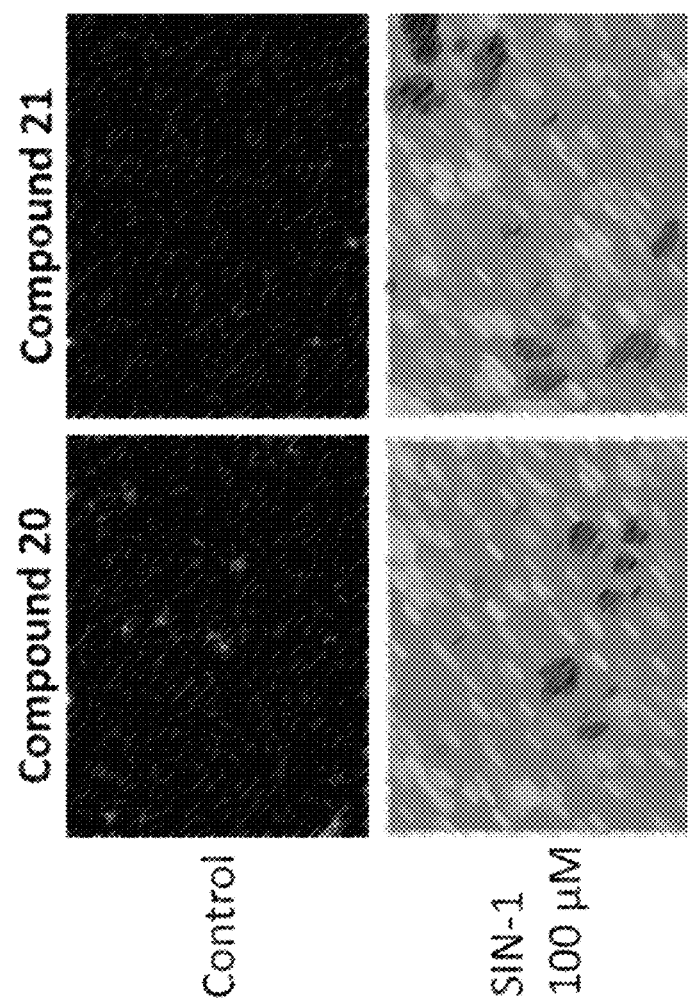
FIG. 8 shows fluorescent microscopy results of C17.2 cells upon treatment with SIN-1, a peroxynitrite generator, using Compounds 20 and 21. The cells were incubated with Compound 20 or 21 at a concentration of 1 µM, and then treated with (Lower) or without (Upper) SIN-1.
Figure 9:
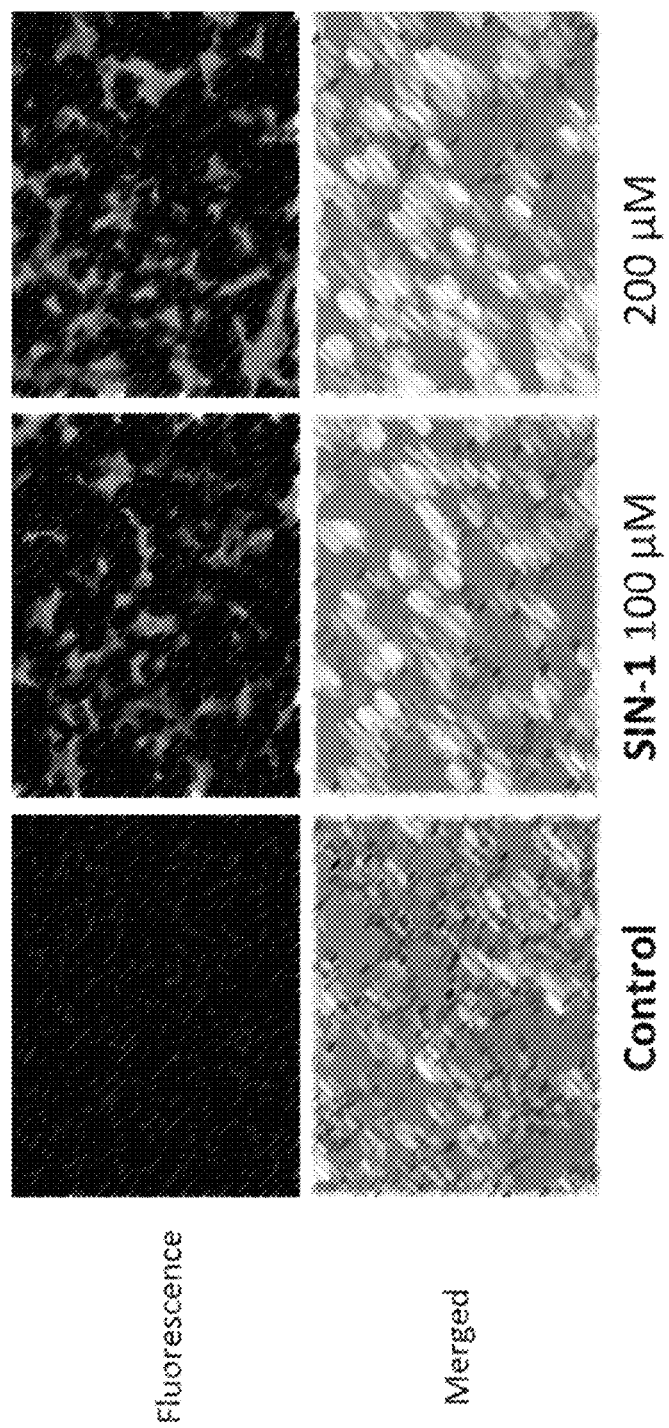
FIG. 9 shows fluorescent microscopy results of SH-SY5Y cells upon treatment with or without SIN-1, a peroxynitrite generator, using Compounds 24. SH-SY5Y cells were co-stained with different compounds with or without SIN-1 for 1 h, and then washed quickly with PBS for 3 times and maintained in non-phenol red medium. Left: no SIN-1 treatment; Middle: with 100 µM SIN-1 treatment; Right: with 200 µM SIN-1 treatment.
Figure 10:
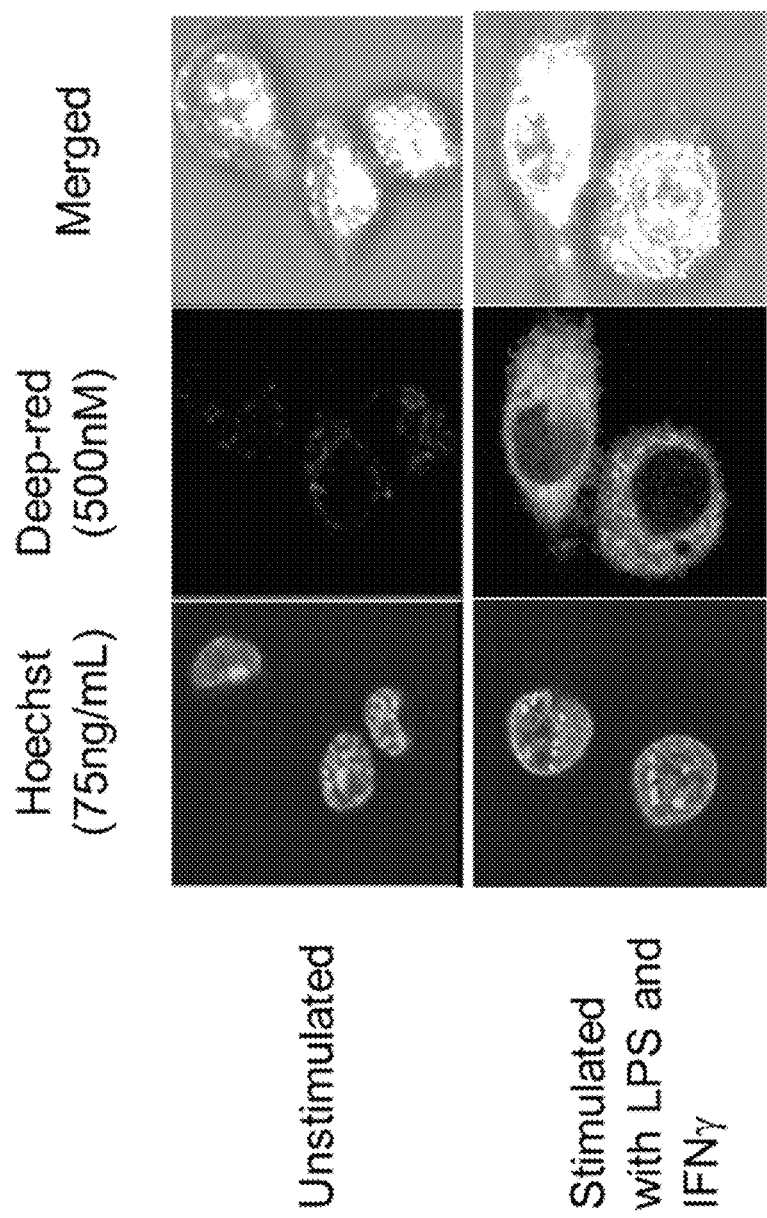
FIG. 10 shows fluorescent microscopy results of Raw 264.7 macrophages under the stimulation conditions. The macrophage cells were incubated with Compound 27 at a concentration of 500 nM. Upper: Control; Lower: The macrophages were stimulated with LPS and IFN-γ for 14 hr. Left: Nuclear staining with Hoechst; Middle: Compound 27; Right: Merged.
Figure 11:
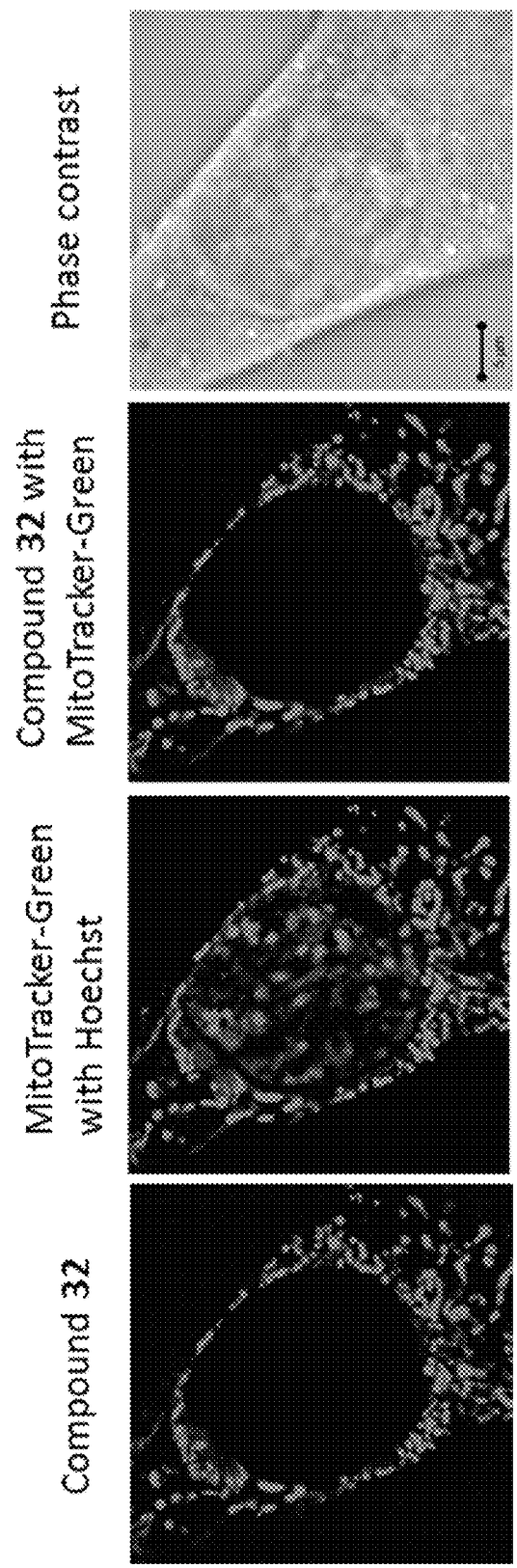
FIG. 11 shows fluorescent microscopy results of C17.2 cells upon treated with SIN-1, a peroxynitrite generator, using Compounds 32. The cells were incubated with Compound 32 at a concentration of 5 µM. The colocalization of red signal from Compound 32 and green signal from Mitotracker-Green indicates Compound 32 selectively localizes to mitochondria of cells.

The reactivity of Compound 30 is compared with different reactive oxygen species (ROS) and reactive nitrogen species (RNS). Specifically, the 1 µM solution of compound 30 is treated with various ROS and RNS. FIG. 5B shows that treatment with peroxynitrite results in a much higher increase in fluorescence intensity of Compound 22 than treatment with other ROS and RNS.

Example 11

Application of Fluorogenic Compounds in Cell Assay

Human SH-SY5Y neuroblastoma cells (ATCC, USA) were maintained in high glucose Dulbecco's Modified Eagle Medium (DMEM, Hyclone) supplemented with 10% fetal bovine serum (FBS, Gibco), 1% penicillin/streptomycin (PS, Gibco) and 1% L-glutamine (Gibco). Mouse C17.2 neural progenitor cells (ATCC, USA) were maintained in high glucose Dulbecco's Modified Eagle Medium supplemented with 8% fetal bovine serum (Gibco), 4% horse serum (Gibco), 1% penicillin/streptomycin and 1% L-glutamine. Mouse RAW264.7 macrophage cells (ATCC, USA) were maintained in high glucose Dulbecco's Modified Eagle Medium (DMEM, Hyclone) supplemented with 10% fetal bovine serum (Gibco), 1% penicillin/streptomycin (Gibco) and 1% L-glutamine.

Generally, cells were grown to confluence prior to experiment. Cells were incubated with Compounds) 6, 7, 8, 14, 20, 21, 24, 27, and 32, respectively for 1 hr, and then washed three times with PBS buffer. Only very weak fluorescence was observed in the absence of stimulants, such as SIN-1 or LPS (lipopolysaccharide)/IFN-γ (Interferon-γ). The fluorescence of compounds was strongly induced after treatment with stimulants, such as SIN-1 or LPS/IFN-γ. The results, as shown in FIGS. 6-11, demonstrate that the compounds of the present invention can be used for the detection of peroxynitrite in living cells.

Example 12

Screening Peroxynitrite Scavengers by Compound 14 Based Platform

SH-SY5Y cells were seeded at a density of $5 \times 10^4$ cells per well onto 96-well plates and incubated at 37° C. under 5% $CO_2$ atmosphere in DMEM medium supplemented with 10% FBS, 1% PS plus 1% L-glutamine. Cells were subjected to serum free medium containing 20 µM Compound 14 in the next day. Cells were then treated with or without different concentration of drug candidates (10 µM, 100 µM) for 10 min, followed by adding SIN-1 to final concentration of 1 mM for 2 h.

The plates were then subjected to spectrofluorometer (Lambda55, PerkinElmer) at an excitation wavelength of 543 nm and emission wavelength of 567 nm. The group in which the cells were treated with neither drug candidates nor SIN-1 was considered as "Ctrl" group; the group in which the cells were treated with SIN-1 but without drug candidates was considered as "Ctrl+SIN-1" group; and the group in which the cells were treated with both drug candidates and SIN-1 was considered as "drug+SIN-1" group.

Figure 12:
FIG. 12 shows a representative figure of screening drugs for scavenging peroxynitrite with Compound 14. SH-SY5Y cells were seeded in 96 well black plates and incubated with Compound 14. The cells were then treated with SIN-1 in the presence of different drug candidates. The fluorescence intensity for each well was recorded and used to determine the scavenging activity of the drug candidate.

The scavenging activity of drug candidates was calculated by $\{[(A_{ctrl+SIN-1}-A_{ctrl})-(A_{drug+SIN-1}-A_{ctrl})]/(A_{ctrl+SIN-1}-A_{ctrl})\}*100\%$. A representative figure of the screening results using Compound 14 based platform is shown in FIG. 12.

Example 13

Application of Compound 14 for Detecting Peroxynitrite in Brain Slices Ex Vivo

SD rats were decapitated and the skulls were quickly opened. After removal of the frontal and occipital poles (including the cerebellum), the isolated brain was immediately placed into ice-cold ACSF (Artificial cerebrospinal fluid) saturated with oxygen. After dissection of the rat brain, the specimens were placed into ACSF (saturated with 95% $O_2$ to 5% $CO_2$). The specimens were sliced in 300 µm thick sections on a NVSL/NVSLM1 tissue slicer (World Precision Instruments Inc., USA). Slices were collected and placed in 6-well culture dishes and maintained with 1 ml culture medium consisting of 50% minimum essential medium, 24% horse serum and 25% HBSS, 1% penicillin-streptomycin (all from Invitrogen) and supplemented with 36 mM glucose, and 25 mM Hepes (Sigma, St. Louis, Mo., USA) (pH 7.2). After 1 day in culture, culture medium was replaced with fresh medium containing no antibiotics. After 5 days culture, slices were pre-staining with 10 µM Compound 14 for 30 min and then washed out with new medium. Slides were then treated with or without SIN-1 (200 µM) and FeTMPyP (50 μM), a peroxynitrite decomposer, and monitored by fluorescence microscopy.

Figure 13:
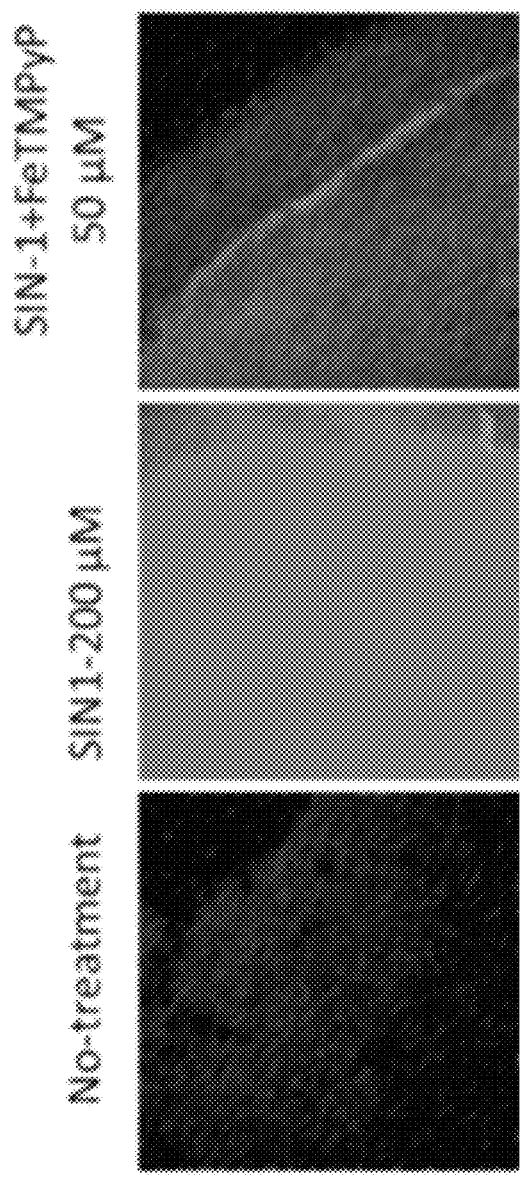
FIG. 13 shows fluorescent microscopy results of ex vivo rats brain slices upon treatment with SIN-1, a peroxynitrite generator, using Compounds 14.

The results, as shown in FIG. 13, demonstrate that Compound 14 reacts with peroxynitrite to give strong yellow fluorescence signals in ex vivo experimental systems.

Example 14

Application of Compound 14 for Detecting Endogenous Peroxynitrite Formation in Ischemic Brain Tissues C57 mice (8 weeks) were fasted for 6 hour before experiments. After fasting, the ethanol group mice were given 50% (vol/vol) ethanol at a total accumulative dosage of 5 g/kg body weight by 3 equally divided gavages in 20 minute intervals. After 6 hours of fasting, the ethanol group mice were given 50% (vol/vol) ethanol at a total accumulative dosage of 5 g/kg body weight by 3 equally divided gavages in 20 minute intervals. Sham mice group received the same volume of water.

After 3 h treated with ethanol, mice were anesthetized and live in situ reperfusion with Compound 14 (1 μM, 2 ml/min, total 25 ml). Fresh liver sample sectioned into 15 μM cryosection slices. After washed with PBS for 5 min and then incubated with DAPI for 10 min, the sections were monitored by epifluorescence microscopy.

Figure 14:
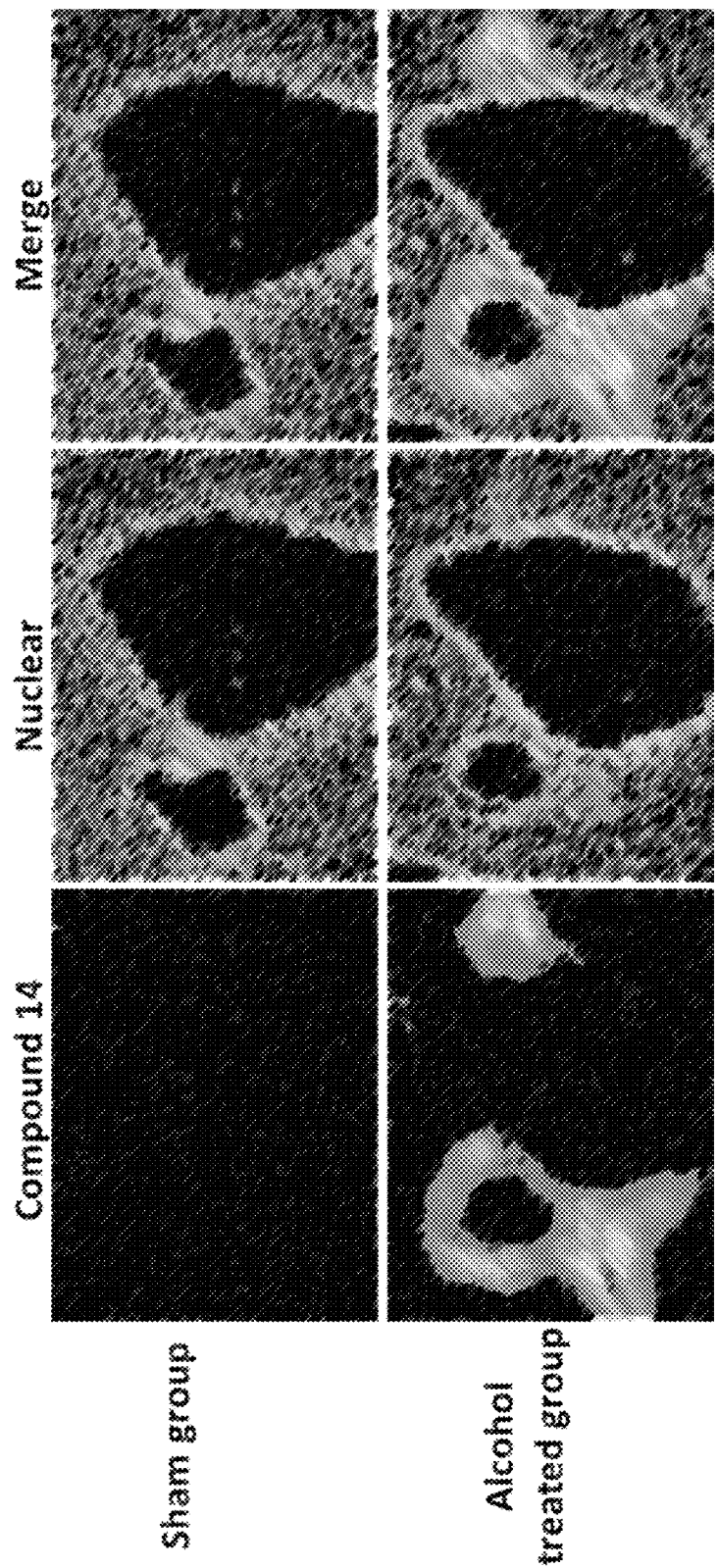
FIG. 14 shows fluorescent microscopy results of liver sample sections from ethanol treated or non-treated mice (Ethanol group or Sham group, respectively) using Compounds 14.

As shown in FIG. 14, strong fluorescence signal from Compound 14 was observed in samples from alcohol treated mice, indicating that peroxynitrite was produced in acute alcohol induced injury of liver.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

We claim:

1. A compound of formula (I) or (II):

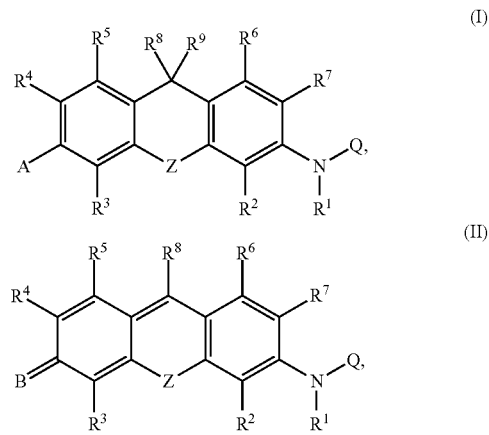

or a tautomer thereof;

wherein N is a nitrogen atom, and is linked to Q and $R^1$ through single covalent bonds;

$R^1$ is H, alkyl, halogenated alkyl, alkenyl, alkynyl, alkoxyalkyl, heteroalkyl, cycloalkyl, cycloalkenyl, cycloalkynyl, heterocyclyl, aminoalkyl, arylalkyl, alkyloxy, carboxyalkyl, alkylamino, alkoxyamino, alkylamido, alkoxyamido, or acyl;

each of $R^2$, $R^3$, $R^4$, $R^5$, $R^6$ and $R^7$ is independently H, F, Br, I, CN, alkyl, halogenated alkyl, heteroalkyl, alkenyl, alkynyl, aralkyl, aryl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thiol, thioalkyl, alkoxy, alkylthio, alkoxyalkyl, aryloxy, arylalkoxy, acyloxy, nitro, carbamoyl, trifluoromethyl, phenoxy, benzyloxy, phosphonic acid, phosphate ester, sulfonic acid (—$SO_3H$), sulfonate ester, sulfonamide, —C(=O)—$P^1$ or —C(=O)-M-$P^2$;

each of $P^1$ and $P^2$ is independently hydrogen, halo, alkoxy, hydroxy, thiol, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, alkyltriphenylphosphonium, or heterocyclyl having from 3 to 7 ring atoms; M is alkylene, alkenylene, alkynylene, arylene, aralkylene or alkarylene;

A is $NR^{11}R^{12}$ and B is $N^+R^{11}R^{12}$ with a biologically compatible counterion selected from chloride, bromide, iodide, sulfate, alkanesulfonate, arylsulfonate, phosphate, perchlorate, tetrafluoroborate, tetraphenylboride, nitrate and anions of aromatic or aliphatic carboxylic acids;

wherein: $R^{11}$ in combination with $R^4$ or $R^{12}$ in combination with $R^3$, but not both, forms a 5- or 6-membered ring that is saturated or unsaturated, or further fused with an aryl or heteroaryl ring, and is optionally substituted by one or more alkyls, carboxylic acids, sulfonic acids (—$SO_3H$), or their salts, ester or amide derivatives the other of $R^{11}$ or $R^{12}$ is H, alkyl, halogenated alkyl, alkenyl, alkynyl, alkoxyalkyl, heteroalkyl, cycloalkyl, cycloalkenyl, cycloalkynyl, heterocyclyl, aminoalkyl, arylalkyl, alkyloxy, acyl, carboxyalkyl, sulfoalkyl, a salt of carboxyalkyl, a salt of sulfoalkyl, or an ester or amide of carboxyalkyl or sulfoalkyl; or $R^{11}$ in combination with $R^{12}$ forms a piperazine, which is optionally substituted by alkyl, carboxylic acid, a salt of carboxylic acid, or a carboxylic acid ester of an alcohol;

Z is O;

$R^8$ has the formula

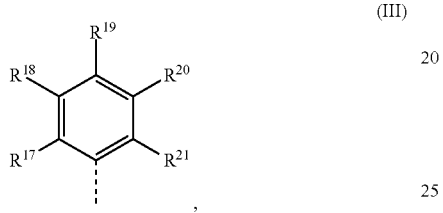

(III)

wherein each of $R^{17}$, $R^{18}$, $R^{19}$, $R^{20}$ and $R^{21}$ is independently H, F, Cl, Br, I, CN, nitro, a carboxylic acid, a salt of carboxylic acid, sulfonate ester (—$SO_3R^{15}$), hydroxy, azide, alkyl, alkenyl, alkynyl, heteroalkyl, cycloalkyl, cycloalkenyl, cycloalkynyl, aryl, alkylaryl, arylalkyl, heterocyclyl, alkoxy, alkoxyalkyl, alkoxyalkoxy, acyl, alkylcarbonylalkyl, halogenated alkylcarbonylalkyl, trifluoromethylcarbonylalkyl, aminoalkyl, carboxyalkyl, thiol, alkylthio, amino, alkylamino, dialkylamino, alkoxycarbonyl, alkoxycarbonylalkyl, aminocarbonyl, alkylaminocarbonyl, dialkylaminocarbonyl, or arylcarboxamido, the alkyl or aryl of which is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—$SO_3H$), sulfonate ester (—$SO_3R^{15}$), or sulfonamide (—$SO_2NR^{15}R^{16}$) or $R^{17}$ and $R^{18}$ together, $R^{18}$ and $R^{19}$ together, $R^{19}$ and $R^{20}$ together, or $R^{20}$ and $R^{21}$ together form a 5- or 6-membered cycloalkyl, heterocyclyl, aryl or heteroaryl ring fused with the phenyl ring of formula (III) that is optionally further substituted by one or more F, Cl, Br, I, a carboxylic acid, a salt of carboxylic acid, a carboxylic acid ester of an alcohol, amino, alkylamino, dialkylamino, alkoxy, thiol, alkylthio, alkyltriphenylphosphonium, sulfonic acid (—$SO_3H$), sulfonate ester (—$SO_3R^{15}$), or sulfonamide (—$SO_2NR^{15}R^{16}$), and wherein at least one of $R^{17}$, $R^{18}$, $R^{19}$, $R^{20}$ and $R^{21}$ is not H or alkyl, wherein each of $R^{15}$ and $R^{16}$ represents a saturated or unsaturated, cyclic or acyclic alkyl that is optionally substituted by one or more F, Cl, Br, I, a carboxylic acid, a salt of carboxylic acid, a carboxylic acid ester of an alcohol, amino, alkylamino, dialkylamino, alkoxy, or alkyltriphenylphosphonium;

$R^9$ is H, hydroxy, CN or alkoxy; or $R^9$ in combination with $R^{17}$ or $R^{21}$ forms a 5- or 6-membered spirolactone, spirosultone, spirolactam or spirosultam ring that is optionally and independently substituted by H, F or $CH_3$; and Q is a substituted phenyl represented by formula (IV):

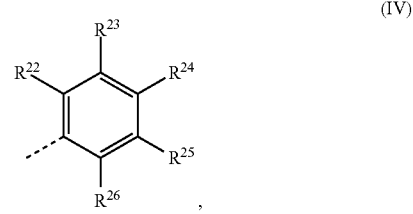

(IV)

wherein each of $R^{22}$, $R^{23}$, $R^{24}$, $R^{25}$, and $R^{26}$ is independently H, hydroxy, alkyl, alkenyl, alkynyl, heteroalkyl, cycloalkyl, cycloalkenyl, cycloalkynyl, aryl, alkylaryl, arylalkyl, heterocyclyl, alkoxy, alkoxyalkyl, alkoxyalkoxy, acyl, alkylcarbonylalkyl, halogenated alkylcarbonylalkyl, trifluoromethylcarbonylalkyl, aminoalkyl, carboxyalkyl, thiol, alkylthio, amino, alkylamino, dialkylamino, alkoxycarbonyl, alkoxycarbonylalkyl, aminocarbonyl, alkylaminocarbonyl, dialkylaminocarbonyl, or arylcarboxamido, wherein at least one of $R^{22}$, $R^{23}$, $R^{24}$, $R^{25}$, and $R^{26}$ is not H, wherein any of the alkyl or aryl of which is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—$SO_3H$), sulfonate ester (—$SO_3R^{15}$), or sulfonamide (—$SO_2NR^{15}R^{16}$); or wherein $R^{22}$ and $R^{23}$ together, $R^{23}$ and $R^{24}$ together, $R^{24}$ and $R^{25}$ together, or $R^{25}$ and $R^{26}$ together form a 5- or 6-membered cycloalkyl, heterocyclyl, aryl or heteroaryl ring fused with the phenyl ring of formula (IV) that is optionally further substituted by one or more F, Cl, Br, I, a carboxylic acid, a salt of carboxylic acid, a carboxylic acid ester of an alcohol, amino, alkylamino, dialkylamino, alkoxy, thiol, alkylthio, alkyltriphenylphosphonium, sulfonic acid (—$SO_3H$), sulfonate ester (—$SO_3R^{15}$), or sulfonamide (—$SO_2NR^{15}R^{16}$) and the remainder of $R^{22}$, $R^{23}$, $R^{24}$, $R^{25}$, and $R^{26}$ are as previously defined; or wherein one of $R^{22}$, $R^{24}$, or $R^{26}$ is $OR^{27}$, $CH_2CH_2COR^{28}$, or $NR^{29}R^{30}$; wherein $R^{27}$ is hydrogen or a group selected from alkyl, alkoxyalkyl, alkanoyl, and polyether; $R^{28}$ is an electron-withdrawing group selected from halogen-substituted lower alkyl, or (C=O)—O—$W_1$, wherein $W_1$ is a group selected from alkyl, alkenyl, alkynyl, cycloalkyl, cycloalkenyl, cycloalkynyl, aryl, alkaryl or arylalkyl, $R^{29}$ and $R^{30}$ are independently hydrogen, alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether and the remainder of $R^{22}$, $R^{23}$, $R^{24}$, $R^{25}$, and $R^{26}$ are as previously defined.

2. The compound of claim 1, wherein the compound has one of formulae 11-19:

-continued
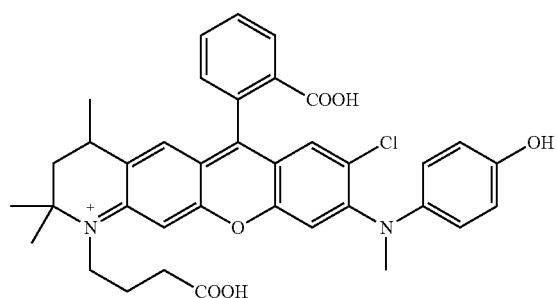
11
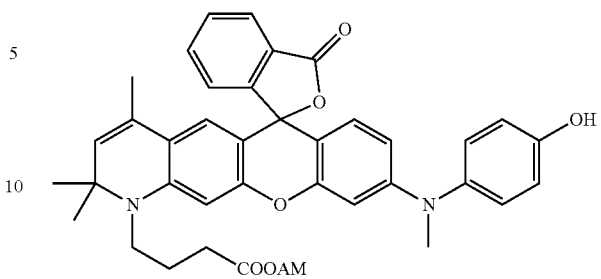
16
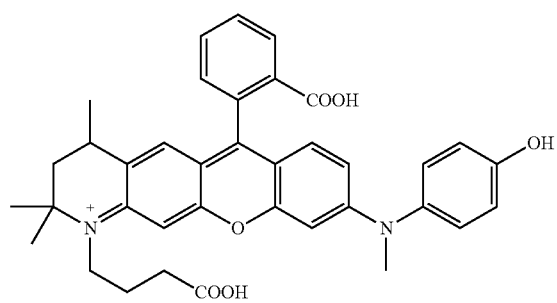
12
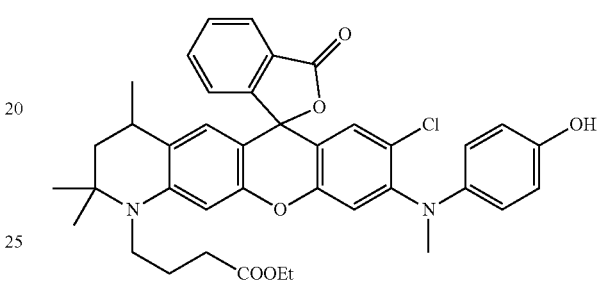
17
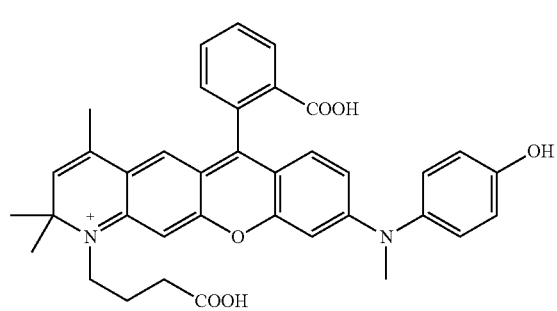
13
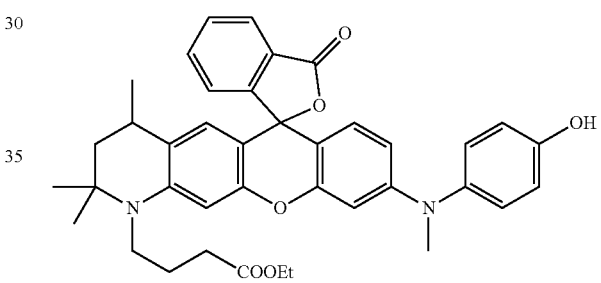
18
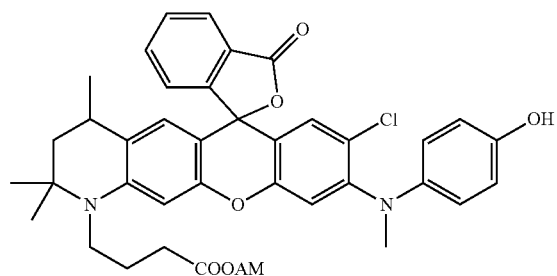
14
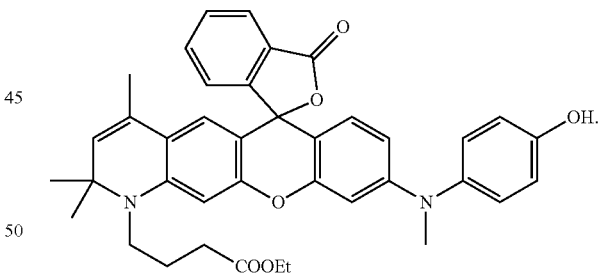
19
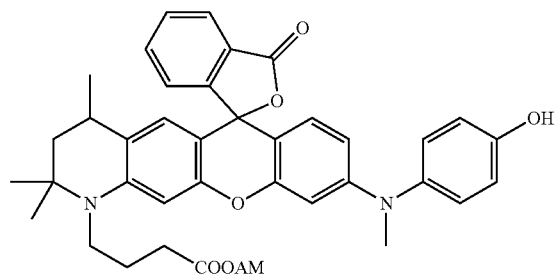
15
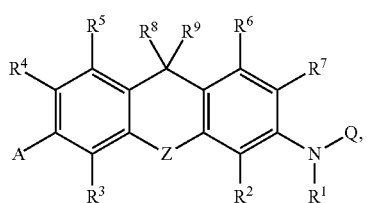
AM = CH$_2$OCOCH$_3$
3. A compound of formula (I) or (II):
(I)

-continued

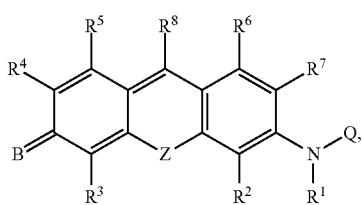

(II)

or a tautomer thereof;
wherein N is a nitrogen atom, and is linked to Q and $R^1$ through single covalent bonds;
$R^1$ is H, alkyl, halogenated alkyl, alkenyl, alkynyl, alkoxyalkyl, heteroalkyl, cycloalkyl, cycloalkenyl, cycloalkynyl, heterocyclyl, aminoalkyl, arylalkyl, alkyloxy, carboxyalkyl, alkylamino, alkoxyamino, alkylamido, alkoxyamido, or acyl;
each of $R^2$, $R^3$, $R^4$, $R^5$, $R^6$ and $R^7$ is independently H, F, Cl, Br, I, CN, alkyl, halogenated alkyl, heteroalkyl, alkenyl, alkynyl, aralkyl, aryl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thiol, thioalkyl, alkoxy, alkylthio, alkoxyalkyl, aryloxy, arylalkoxy, acyloxy, nitro, carbamoyl, trifluoromethyl, phenoxy, benzyloxy, phosphonic acid, phosphate ester, sulfonic acid (—$SO_3H$), sulfonate ester, sulfonamide, —C(=O)—$P^1$ or —C(=O)-M-$P^2$;
each of $P^1$ and $P^2$ is independently hydrogen, halo, alkoxy, hydroxy, thiol, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, alkyltriphenylphosphonium, or heterocyclyl having from 3 to 7 ring atoms; M is alkylene, alkenylene, alkynylene, arylene, aralkylene or alkarylene;
A is $OR^{10}$ or $NR^{11}R^{12}$ and B is O or $N^+R^{11}R^{12}$ with a biologically compatible counterion selected from chloride, bromide, iodide, sulfate, alkanesulfonate, arylsulfonate, phosphate, perchlorate, tetrafluoroborate, tetraphenylboride, nitrate and anions of aromatic or aliphatic carboxylic acids;
wherein $R^{10}$ is H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, carboxyalkyl, alkoxycarbonyl, acyl or aminocarbonyl;
wherein $R^{11}$ in combination with $R^{12}$ forms a piperazine, which is optionally substituted by alkyl, carboxylic acid, a salt of carboxylic acid, or a carboxylic acid ester of an alcohol; or $R^{11}$ in combination with $R^4$, and/or $R^{12}$ in combination with $R^3$, or both, form a 5- or 6-membered ring that is saturated or unsaturated, or further fused with an aryl or heteroaryl ring, and is optionally substituted by one or more alkyls, carboxylic acids, sulfonic acids (—$SO_3H$), or their salts, ester or amide derivatives and $R^{11}$ or $R^{12}$ not combined in the 5- or 6-membered ring is H, alkyl, halogenated alkyl, alkenyl, alkynyl, alkoxyalkyl, heteroalkyl, cycloalkyl, cycloalkenyl, cycloalkynyl, heterocyclyl, aminoalkyl, arylalkyl, alkyloxy, acyl, carboxyalkyl, sulfoalkyl, a salt of carboxyalkyl, a salt of sulfoalkyl, or an ester or amide of carboxyalkyl or sulfoalkyl;
Z is O or $SiR^{13}R^{14}$;
wherein each of $R^{13}$ and $R^{14}$ is independently H, alkyl, halogenated alkyl, heteroalkyl, alkenyl, alkynyl, aralkyl, aryl, alkaryl, heterocyclyl, cycloalkyl, cycloalkenyl, cycloalkynyl, hydroxyalkyl, aminoalkyl, hydroxy, thiol, thioalkyl, alkoxy, alkylthio, alkoxyalkyl, aryloxy, arylalkoxy, acyloxy, carbamoyl, trifluoromethyl, phenoxy, benzyloxy, phosphonic acid, phosphate ester, sulfonic acid (—$SO_3H$), sulfonate ester, sulfonamide, carboxylic acid, carboxylic ester, or carboxylic amide; or $R^{13}$ in combination with $R^{14}$ forms a saturated 5- or 6-membered heterocycle that is optionally substituted by alkyl, carboxylic acid, a salt of carboxylic acid, or a carboxylic acid ester of an alcohol;
$R^8$ has the formula

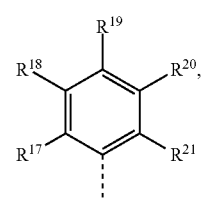

(III)

wherein at least one of $R^{18}$, $R^{19}$, and $R^{20}$ is F, Cl, Br, I, CN, nitro, a carboxylic acid, a salt of carboxylic acid, sulfonate ester (—$SO_3R^{15}$), hydroxy, azide, thiol, alkylthio, alkylaminocarbonyl, dialkylaminocarbonyl, or arylcarboxamido the alkyl or aryl of which is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—$SO_3H$), sulfonate ester (—$SO_3R^{15}$), or sulfonamide (—$SO_2NR^{15}R^{16}$, and the remaining $R^{17}$, $R^{18}$, $R^{19}$, $R^{20}$ and $R^{21}$ are independently H, F, Cl, Br, I, CN, nitro, a carboxylic acid, a salt of carboxylic acid, sulfonate ester (—$SO_3R^{15}$), azide, alkyl, alkenyl, alkynyl, heteroalkyl, cycloalkyl, cycloalkenyl, cycloalkynyl, aryl, alkylaryl, arylalkyl, heterocyclyl, hydroxyl, alkoxy, alkoxyalkyl, alkoxyalkoxy, acyl, alkylcarbonylalkyl, halogenated alkylcarbonylalkyl, trifluoromethylcarbonylalkyl, aminoalkyl, carboxyalkyl, thiol, alkylthio, amino, alkylamino, dialkylamino, alkoxycarbonyl, alkoxycarbonylalkyl, aminocarbonyl, alkylaminocarbonyl, dialkylaminocarbonyl, or arylcarboxamido the alkyl or aryl of which is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—$SO_3H$), sulfonate ester (—$SO_3R^{15}$), or sulfonamide (—$SO_2NR^{15}R^{16}$) or $R^{17}$ and $R^{18}$ together, $R^{18}$ and $R^{19}$ together, $R^{19}$ and $R^{20}$ together, or $R^{20}$ and $R^{21}$ together form a 5- or 6-membered cycloalkyl, heterocyclyl, aryl or heteroaryl ring fused with the phenyl ring of formula (III) that is optionally further substituted by one or more F, Cl, Br, I, a carboxylic acid, a salt of carboxylic acid, a carboxylic acid ester of an alcohol, amino, alkylamino, dialkylamino, alkoxy, thiol, alkylthio, alkyltriphenylphosphonium, sulfonic acid (—$SO_3H$), sulfonate ester (—$SO_3R^{15}$), or sulfonamide (—$SO_2NR^{15}R^{16}$), and wherein at least one of $R^{17}$, $R^{18}$, $R^{19}$, $R^{20}$ and $R^{21}$ is not H or alkyl, wherein each of $R^{15}$ and $R^{16}$ represents a saturated or unsaturated, cyclic or acyclic alkyl that is optionally substituted by one or more F, Cl, Br, I, a carboxylic acid, a salt of carboxylic acid, a carboxylic acid ester of an alcohol, amino, alkylamino, dialkylamino, alkoxy, or alkyltriphenylphosphonium;

$R^9$ is H, hydroxy, CN or alkoxy; or $R^9$ in combination with $R^{17}$ or $R^{21}$ forms a 5- or 6-membered spirolactone, spirosultone, spirolactam or spirosultam ring that is optionally and independently substituted by H, F or $CH_3$; and Q is a substituted phenyl represented by formula (IV):

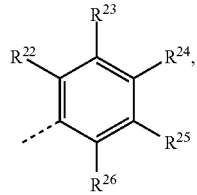

(IV)

wherein each of $R^{22}$, $R^{23}$, $R^{24}$, $R^{25}$, and $R^{26}$ is independently H, hydroxy, alkyl, alkenyl, alkynyl, heteroalkyl, cycloalkyl, cycloalkenyl, cycloalkynyl, aryl, alkylaryl, arylalkyl, heterocyclyl, alkoxy, alkoxyalkyl, alkoxyalkoxy, acyl, alkylcarbonylalkyl, halogenated alkylcarbonylalkyl, trifluoromethylcarbonylalkyl, aminoalkyl, carboxyalkyl, thiol, alkylthio, amino, alkylamino, dialkylamino, alkoxycarbonyl, alkoxycarbonylalkyl, aminocarbonyl, alkylaminocarbonyl, dialkylaminocarbonyl, or arylcarboxamido, wherein any of the alkyl or aryl of which is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—$SO_3H$), sulfonate ester (—$SO_3R^{15}$), or sulfonamide (—$SO_2NR^{15}R^{16}$), wherein at least one of $R^{22}$, $R^{23}$, $R^{24}$, $R^{25}$, and $R^{26}$ is not H; or wherein $R^{22}$ and $R^{23}$ together, $R^{23}$ and $R^{24}$ together, $R^{24}$ and $R^{25}$ together, or $R^{25}$ and $R^{26}$ together form a 5- or 6-membered cycloalkyl, heterocyclyl, aryl or heteroaryl ring fused with the phenyl ring of formula (IV) that is optionally further substituted by one or more F, Cl, Br, I, a carboxylic acid, a salt of carboxylic acid, a carboxylic acid ester of an alcohol, amino, alkylamino, dialkylamino, alkoxy, thiol, alkylthio, alkyltriphenylphosphonium, sulfonic acid (—$SO_3H$), sulfonate ester (—$SO_3R^{15}$), or sulfonamide (—$SO_2NR^{15}R^{16}$) and the remainder of $R^{22}$, $R^{23}$, $R^{24}$, $R^{25}$, and $R^{26}$ are as previously defined; or wherein one of $R^{22}$, $R^{24}$, or $R^{26}$ is $OR^{27}$, $CH_2CH_2COR^{28}$, or $NR^{29}R^{30}$; wherein $R^{27}$ is hydrogen or a group selected from alkyl, alkoxyalkyl, alkanoyl, and polyether; $R^{28}$ is an electron-withdrawing group selected from halogen-substituted lower alkyl, or (C=O)—O—$W_1$, wherein $W_1$ is a group selected from alkyl, alkenyl, alkynyl, cycloalkyl, cycloalkenyl, cycloalkynyl, aryl, alkaryl or arylalkyl, $R^{29}$ and $R^{30}$ are independently hydrogen, alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether and the remainder of $R^{22}$, $R^{23}$, $R^{24}$, $R^{25}$, and $R^{26}$ are as previously defined.

4. The compound of claim 3, wherein the compound has one of formulae 2-10:

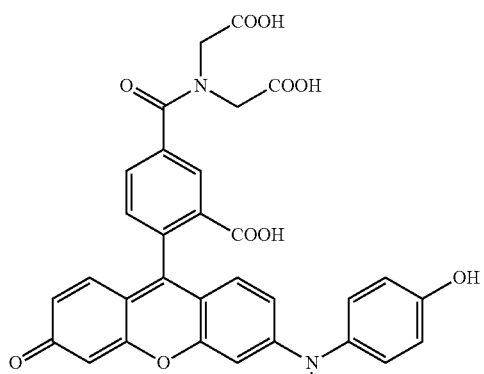

2

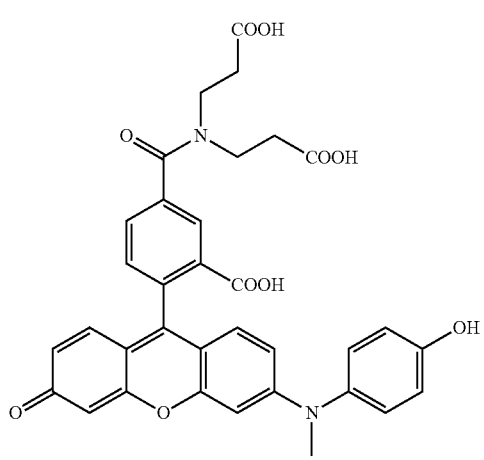

3

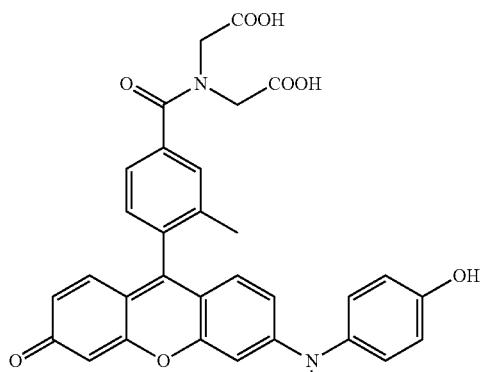

4

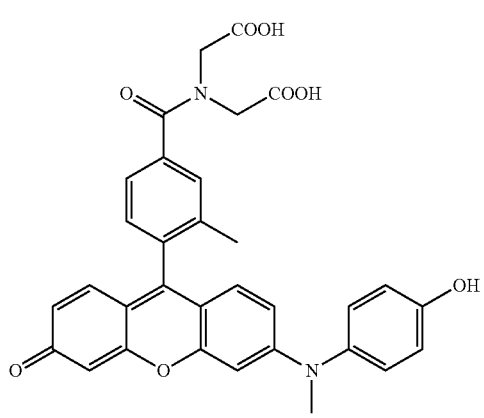

4

77
-continued
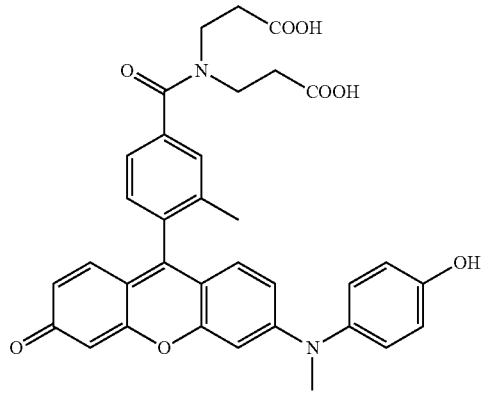
78
-continued
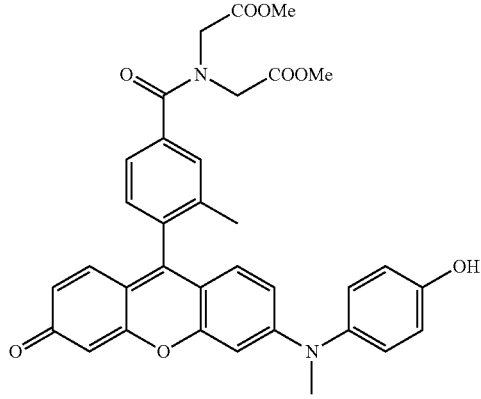
5. A fluorogenic probe composition comprising the compound of claim 1 or 3 and a carrier.
6. The fluorogenic probe composition of claim 5, wherein the fluorogenic probe composition further comprises a solvent, an acid, a base, a buffer solution, or a combination thereof.
* * * * *

UNITED STATES PATENT AND TRADEMARK OFFICE
CERTIFICATE OF CORRECTION

PATENT NO. : 9,651,528 B2
APPLICATION NO. : 13/754499
DATED : May 16, 2017
INVENTOR(S) : Dan Yang et al.

It is certified that error appears in the above-identified patent and that said Letters Patent is hereby corrected as shown below:

In the Specification

Column 1,
Line 1, [no heading] should read --DESCRIPTION--.

Column 2,
Line 9, "$(O_2\cdot^-)$" should read --$(O_2\cdot^-)$--.
Line 17, "$CO_3^-$. and $NO_2$." should read --$CO_3^-\cdot$ and $NO_2\cdot$)--.
Lines 26-27, "inflammatory bowel disease," should read --inflammatory bowel disease--.

Column 5,

Lines 15-21, " 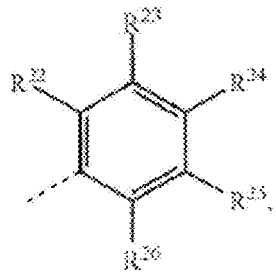 " should read
-- 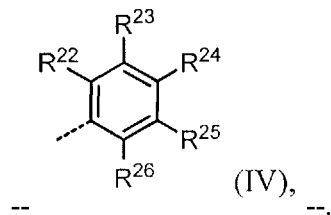 (IV), --.

Column 6,
Line 22, "(.OH)," should read --(•OH),--.
Line 24, "$O_2\cdot^-$, NO, ROO." should read --$O_2\cdot^-$, NO, ROO•--.

Signed and Sealed this
Sixth Day of March, 2018

Andrei Iancu
*Director of the United States Patent and Trademark Office*

Line 33, "(.OH)," should read --(•OH),--.
Line 35, "O₂.⁻, NO, ROO." should read --O₂•⁻, NO, ROO•--.
Line 44, "(.OH)," should read --(•OH),--.
Line 46, "O₂.⁻, NO, ROO." should read --O₂•⁻, NO, ROO•--.
Line 56, "(.OH)," should read --(•OH),--.
Line 58, "O₂.⁻, NO, ROO." should read --O₂•⁻, NO, ROO•--.

Column 7,
Line 2, "(.OH)" should read --(•OH)--.
Line 3, "O₂.⁻, NO, ROO." should read --O₂•⁻, NO, ROO•--.
Line 15, "Compounds 14." should read --Compound 14.--.
Line 28, "Compounds 24." should read --Compound 24.--.
Line 43, "Compounds 32." should read --Compound 32.--.
Line 57, "Compounds 14." should read --Compound 14.--.
Lines 60-61, "Compounds 14." should read --Compound 14.--.

Column 10,
Line 60, "Orgeon," should read --Oregon,--.

Column 11,
Line 12, "O₂.⁻, ROO., .OH," should read --O₂•⁻, ROO•, •OH,--.
Line 17, "(NO.), nitrogen dioxide (NO₂.)," should read --(NO•), nitrogen dioxide (NO₂•),--.

Columns 21-22,

Lines 26-45, " 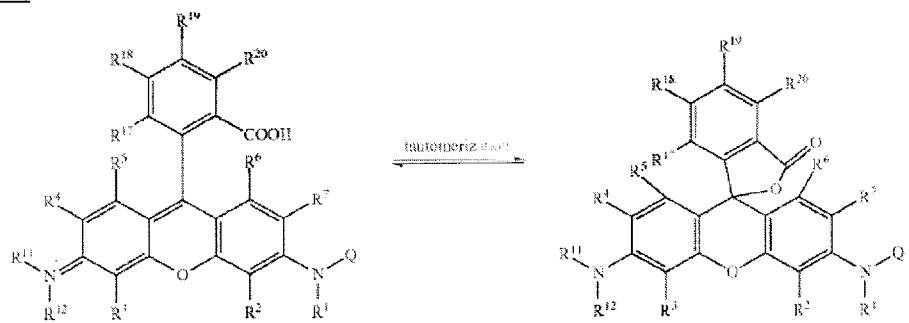 " should read

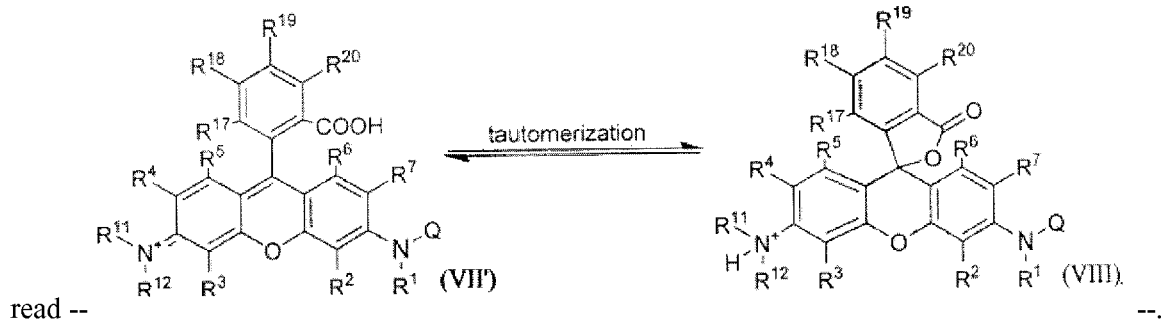

read -- --.

Column 28,
Lines 64-65, "derivatives 24 are" should read --derivative 24 is--.

CERTIFICATE OF CORRECTION (continued)
U.S. Pat. No. 9,651,528 B2

Column 29,

Lines 8-21, " 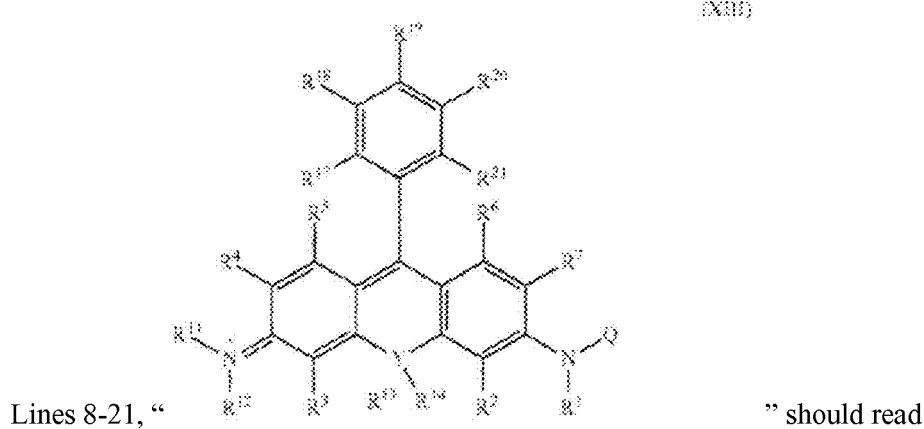 " should read

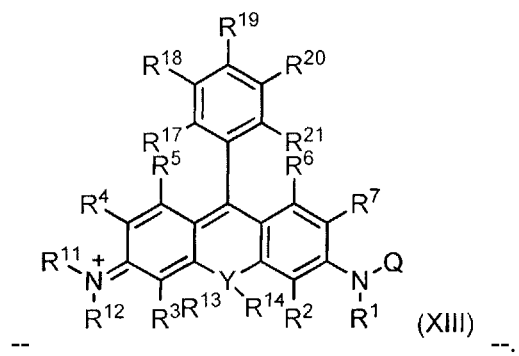

-- --.

Columns 29-30,

Lines 33-49, " 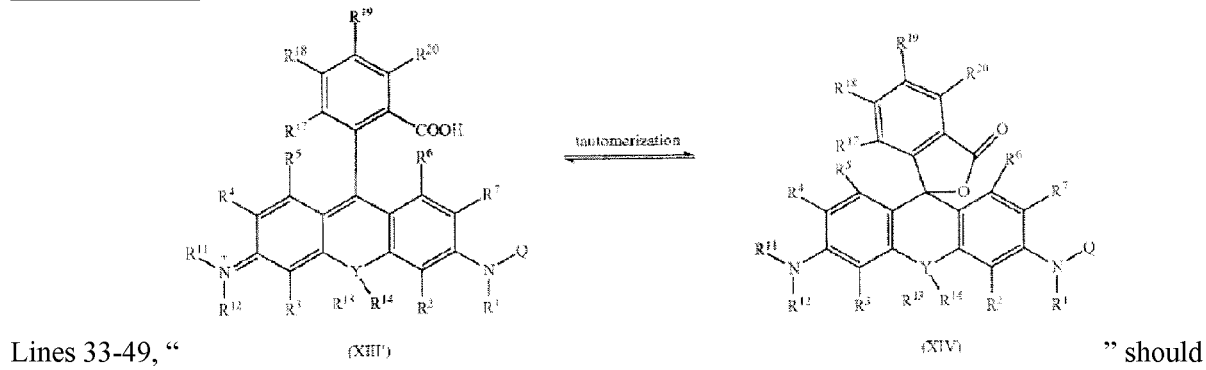 " should read -- 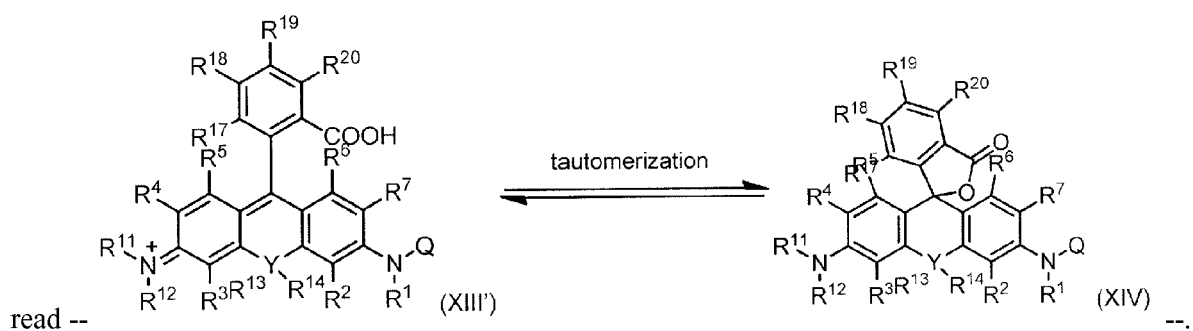 --.

Column 42,
Line 27, "536.0389." should read --536.0389;--.
Line 58, "momol)" should read --mmol)--.

Column 47,
Line 5, "(EDC.HCl)" should read --(EDC·HCl)--.

Column 48,
Line 13, "596.1431." should read --596.1431;--.

Column 49,
Line 35, "534.0960." should read --534.0960;--.

Column 50,
Line 2, "momol)" should read --mmol)--.

Column 51,
Line 38, "(EDC.HCl)" should read --(EDC·HCl)--.

Column 53,
Line 65, "$^{11}$H" should read --$^1$H--.

Column 62,
Line 35, "(EDC.HCl)," should read --(EDC·HCl),--.
Line 41, "extracts was" should read --extract was--.

Column 63,
Line 25, "(EDC.HCl)," should read --(EDC·HCl),--.
Line 62, "(.OH)," should read --(•OH),--.
Line 64, "$O_2._$, NO, ROO." should read --$O_2^{•-}$, NO, ROO•--.

Column 64,
Line 39, "(.OH)," should read --(•OH),--.
Line 41, "$O_2._$, NO, ROO." should read --$O_2^{•-}$, NO, ROO•--.
Line 64, "(.OH)," should read --(•OH),--.
Line 66, "$O_2._$, NO, ROO." should read --$O_2^{•-}$, NO, ROO•--.

Column 65,
Line 23, "(.OH)," should read --(•OH),--.
Line 25, "$O_2._$, NO, ROO." should read --$O_2^{•-}$, NO, ROO•--.

Column 67,
Line 13, "for 6 hour" should read --for 6 hours--.

CERTIFICATE OF CORRECTION (continued)
U.S. Pat. No. 9,651,528 B2

In the Claims

Column 74,
Line 52, "(—SO$_2$NR$^{15}$R$^{16}$) or" should read --(-SO$_2$NR$^{15}$R$^{16}$); or--.

Column 76,

Lines 35-67, " 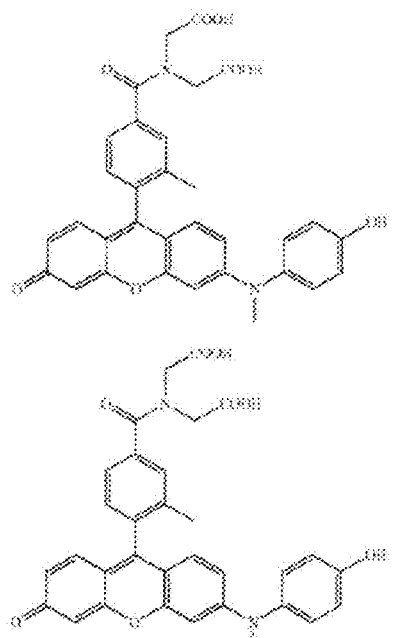 " should read
-- 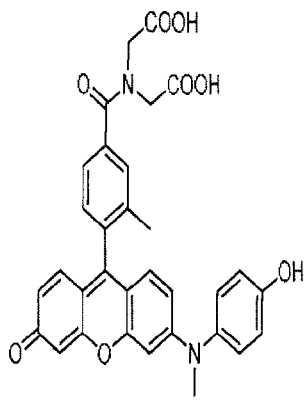 --.